US009796979B2

(12) United States Patent
Feinstein et al.

(10) Patent No.: US 9,796,979 B2
(45) Date of Patent: Oct. 24, 2017

(54) OLIGONUCLEOTIDE MODULATORS OF THE TOLL-LIKE RECEPTOR PATHWAY

(71) Applicant: QUARK PHARMACEUTICALS, INC., Fremont, CA (US)

(72) Inventors: Elena Feinstein, Rehovot (IL); Svetlana Adamsky, Gedera (IL); Sharon Avkin-Nachum, Nes Zionna (IL); Hagar Kalinski, Rishon-Le-Zion (IL); Igor Mett, Rehovot (IL)

(73) Assignee: Quark Pharmaceuticals Inc.

( * ) Notice: Subject to any disclaimer, the term of this patent is extended or adjusted under 35 U.S.C. 154(b) by 0 days.

(21) Appl. No.: 15/222,695

(22) Filed: Jul. 28, 2016

(65) Prior Publication Data

US 2016/0333356 A1    Nov. 17, 2016

Related U.S. Application Data

(63) Continuation-in-part of application No. 14/002,901, filed as application No. PCT/US2012/027174 on Mar. 1, 2012, now Pat. No. 9,487,778.

(60) Provisional application No. 61/448,707, filed on Mar. 3, 2011.

(51) Int. Cl.
*C12N 15/113*    (2010.01)

(52) U.S. Cl.
CPC ...... *C12N 15/1138* (2013.01); *C12N 2310/14* (2013.01); *C12N 2310/317* (2013.01); *C12N 2310/3183* (2013.01); *C12N 2310/32* (2013.01); *C12N 2320/51* (2013.01)

(58) Field of Classification Search
CPC .......................... C12N 15/113; C12N 15/1138
See application file for complete search history.

(56) References Cited

U.S. PATENT DOCUMENTS

| | | |
|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,666,828 A | 5/1987 | Gusella |
| 4,683,202 A | 7/1987 | Mullis |
| 4,801,531 A | 1/1989 | Frossard |
| 4,959,217 A | 9/1990 | Sanders et al. |
| 5,167,616 A | 12/1992 | Haak et al. |
| 5,169,383 A | 12/1992 | Gyory et al. |
| 5,192,659 A | 3/1993 | Simons |
| 5,225,182 A | 7/1993 | Sharma |
| 5,272,057 A | 12/1993 | Smulson et al. |
| 5,580,859 A | 12/1996 | Felgner et al. |
| 5,589,466 A | 12/1996 | Felgner et al. |
| 5,593,972 A | 1/1997 | Weiner et al. |
| 5,898,031 A | 4/1999 | Crooke |
| 6,107,094 A | 8/2000 | Crooke |
| 6,121,426 A | 9/2000 | Vogel et al. |
| 6,693,187 B1 | 2/2004 | Dellinger |
| 7,067,641 B2 | 6/2006 | Dellinger |
| 8,796,239 B2 | 8/2014 | Avkin-Nachum |
| 9,487,778 B2 | 11/2016 | Feinstein et al. |
| 2004/0019001 A1 | 1/2004 | McSwiggen |
| 2004/0063654 A1 | 4/2004 | Davis et al. |
| 2005/0004064 A1 | 1/2005 | Tei et al. |
| 2006/0058255 A1 | 3/2006 | Chen et al. |
| 2008/0293655 A1 | 11/2008 | Aygun et al. |
| 2009/0162365 A1 | 6/2009 | Feinstein et al. |
| 2010/0292301 A1 | 11/2010 | Feinstein et al. |
| 2011/0112168 A1 | 5/2011 | Feinstein et al. |
| 2014/0329878 A1 | 11/2014 | Feinstein et al. |

FOREIGN PATENT DOCUMENTS

| | | |
|---|---|---|
| WO | 93/23569 A1 | 11/1993 |
| WO | 98/39352 A1 | 9/1998 |
| WO | 99/14226 A2 | 3/1999 |
| WO | 99/32619 A1 | 7/1999 |
| WO | 00/44914 A1 | 8/2000 |
| WO | 00/47599 A1 | 8/2000 |
| WO | 00/49035 A1 | 8/2000 |
| WO | 0044895 A1 | 8/2000 |
| WO | 00/63364 A2 | 10/2000 |
| WO | 01/29058 A1 | 4/2001 |
| WO | 01/36641 A2 | 5/2001 |
| WO | 01/36646 A1 | 5/2001 |
| WO | 0175164 A2 | 10/2001 |
| WO | 02/44321 A2 | 6/2002 |
| WO | 2004/015107 A2 | 2/2004 |

(Continued)

OTHER PUBLICATIONS

Siddall, P.J., et al., Pain report and the relationship of pain to physical factors in the first 6 months following spinal cord injury. Pain. May 1999;81(1-2):187-197.
Siddall, P.J., et al., A longitudinal study of the prevalence and characteristics of pain in the first 5 years following spinal cord injury. Pain. Jun. 2003;103(3):249-257.
Simeoni et al., Insight into the mechanism of the peptide-based gene delivery system MPG: implications for delivery of siRNA into mammalian cells. Nucleic Acids Res. Jun. 1, 2003;31(11):2717-2724.
Sioud and Leirdal, Potential Design Rules and Enzymatic Synthesis of siRNAs. Methods Mol Biol. 2004;252:457-469.
Song et al., Antibody mediated in vivo delivery of small interfering RNAs via cell-surface receptors. Nat Biotechnol. Jun. 2005;23(6):709-17.
Sorensen et al., Gene Silencing by Systemic Delivery of Synthetic siRNAs in Adult Mice. J Mol Bioi. Apr. 4, 2003;327 (4):761-766.
Sved et al., Relationship between surgery and pain following spinal cord injury. Spinal Cord. Aug. 1997;35 (8):526-530.

(Continued)

*Primary Examiner* — Jon E Angell
(74) *Attorney, Agent, or Firm* — Nutter McClennen & Fish LLP; Konstantin Linnik

(57) ABSTRACT

Disclosed herein are double stranded nucleic acid molecules and pharmaceutical compositions comprising same useful in the treatment of, inter alia, acute and chronic inflammation, neuropathic pain, primary graft dysfunction (PGD) after lung transplantation in a subject in need thereof. The compounds are preferably chemically synthesized and modified dsRNA compounds, which down regulate or inhibit expression of Toll like receptor 4.

10 Claims, 3 Drawing Sheets

(56) References Cited

FOREIGN PATENT DOCUMENTS

| | | |
|---|---|---|
| WO | 2004/041924 A2 | 5/2004 |
| WO | 2004/083430 A2 | 9/2004 |
| WO | 2004/093778 A2 | 11/2004 |
| WO | 2006/047842 A2 | 5/2006 |
| WO | 2007/041218 A2 | 4/2007 |
| WO | 2007/091269 A2 | 8/2007 |
| WO | 2008/132723 A2 | 11/2008 |
| WO | 2009/000929 A2 | 12/2008 |
| WO | 2009/015107 A1 | 1/2009 |
| WO | 2010/053971 A1 | 5/2010 |
| WO | 2010/144336 A2 | 12/2010 |
| WO | 2011/066475 A1 | 6/2011 |
| WO | 2011/084193 A1 | 7/2011 |
| WO | 2011/085056 A1 | 7/2011 |

OTHER PUBLICATIONS

Takei et al., 5'-,3'-Inverted Thymidine-modified Antisense Oligodeoxynucleotide Targeting Midkine. Its Design and Application for Cancer Therapy. J Bioi Chem. Jun. 28, 2002;277(26):23800-23806.

Testoni et al., A New Method of "In-Cell Reverse Transcriptase-Polymerase Chain Reaction" for the Detection of BCRIABL Transcript in Chronic Myeloid Leukemia Patients. Blood. May 1, 1996;87(9):3822-3827.

Tolentino et al., Intravitreal Injection of Vascular Endothelial Growth Factor Small Interfering RNA Inhibits Growth and Leakage in a Nonhuman Primate, Laser-Induced Model of Choroidal Neovascularization. Retina. Feb. 2004;24 (1):132-138.

Ui-Tei et al., Guidelines for the selection of highly effective siRNA sequences for mammalian and chick RNA interference. Nucleic Acids Res. Feb. 9, 2004;32(3):936-948.

Ui-Tei et al., Essential Notes Regarding the Design of Functional siRNAs for Efficient Mammalian RNAi. J Biomed Biotechnol. 2006;2006(4):65052.

Ui-Tei et al., Functional dissection of siRNA sequence by systematic DNA substitution: modified siRNA with a DNA seed arm is a powerful tool for mammalian gene silencing with significantly reduced off-target effect. Nucleic Acids Res. Apr. 2008;36(7):2136-2151.

Weiss et al., Perflubron Enhances Adenovirus-Mediated Gene Expression in Lungs of Transgenic Mice with Chronic Alveolar Filling. Hum Gene Ther. Sep. 20, 1999;10(14):2287-2293.

Wincott and Usman, A Practical Method for the Production of RNA and Ribozymes. Methods Mol Bioi. 1997;74:59-68.

Wincott et al., Synthesis, deprotection, analysis and purification of RNA and ribozymes. Nucleic Acids Res. Jul. 25, 1995;23(14):2677-2684.

Xia et al., siRNA-mediated gene silencing in vitro and in vivo. Nat Biotechnol. Oct. 2002;20(10):1006-1010.

Ajuwon, et al., Stimulation with Peptidoglycan induces interleukin 6 and TLR2 expression and a concomitant downregulation of expression of adiponectin receptors 1 and 2 in 3T3-L1 adipocytes. J Inflamm (Lond). Apr. 6, 2009;6:8. doi: 10.1186/1476-9255-6-8.

Singaporean Search Report for Application No. 201306622-0, mailed Jul. 21, 2015 (7 pages).

Allart et al., 1,5-Anhydro-2-Deoxy-D-Altritol Oligonucleotides as Conformationally Restricted Analogues of Rna. Nucleosides & Nucleotides 1998;17:1523-1526.

Ambros, The functions of animal microRNAs. Nature. Sep. 16, 2004;431(7006):350-355.

Barik, Silence of the transcripts: RNA interference in medicine. J Mol Med (Berl). Oct. 2005;83(10):764-773.

Bartel, MicroRNAs: genomics, biogenesis, mechanism, and function. Cell. Jan. 23, 2004;116(2)281-297.

Bellon et al., Amino-Linked Ribozymes: Post-Synthetic Conjugation of Half-Ribozymes. Nucleosides & Nucleotides 1997; 16:951-954.

Bellon et al., Post-synthetically Ligated Ribozymes: An Alternative Approach to Iterative Solid-Phase Synthesis. Bioconjug Chem. Mar.-Apr. 1997;8(2):204-212.

Bernstein et al., Role for a bidentate ribonuclease in the initiation step of RNA interference. Nature. Jan. 18, 2001;409(6818):363-366.

Bernstein et al., The rest is silence. RNA. Nov. 2001;7(11):1509-21.

Braasch et al., RNA Interference in Mammalian Cells by Chemically-Modified RNA. Biochemistry. Jul. 8, 2003;42 (26):7967-7975.

Caplen et al. Specific inhibition of gene expression by small double-stranded RNAs in invertebrate and vertebrate systems. Proc Natl Acad Sci U S A. Aug. 14, 2001;98(17):9742-9747.

Caruthers et. al., Chemical Synthesis of Deoxyoligonucleotides by the Phosphoramidite Method. Methods Enzymol. 1987;154:287-313.

Chakraborty, Potentiality of Small Interfering Rnas (siRNA) as Recent Therapeutic Targets for Gene-Silencing. Curr Drug Targets. Mar. 2007;8(3):469-482.

Chalk et al., Improved and automated prediction of effective siRNA. Biochem Biophys Res Commun. Jun. 18, 2004;319(1 ):264-274.

Chiu and Rana, siRNA function in RNAi: a chemical modification analysis. RNA. Sep. 2003;9(9):1034-1048.

Czaudema et al.. Structural variations and stabilising modifications of synthetic siRNAs in mammalian cells. Nucleic Acids Res. Jun. 1, 2003;31 (11 ):2705-2716.

Densmore et al., Aerosol Delivery of Robust Polyethyleneimine—DNA Complexes for Gene Therapy and Genetic Immunization. Mol Ther. Feb. 2000;1(2):180-188.

Durgan et al., Inhalable siRNA: Potential as a Therapeutic Agent in the Lungs. Mol Pharm. Jul.-Aug. 2008;5(4):559-566.

Eckstein, Nucleoside Phosphorothioates. Annu Rev Biochem. 1985;54:367-402.

Elbashir et al., Duplexes of 21-nucleotide RNAs mediate RNA interference in cultured mammalian cells. Nature. May 24, 2001;411 (6836):494-498.

Elbashir et al., RNA interference is mediated by 21-and 22-nucleotide RNAs. Genes Dev. Jan. 15, 2001;15 (2):188-200.

Elmen et al., Locked nucleic acid (LNA) mediated improvements in siRNA stability and functionality. Nucleic Acids Res. Jan. 14, 2005;33(1):439-447.

Fire et al, Potent and specific genetic interference by double-stranded RNA in Caenorhabditis elegans. Nature. Feb. 19, 1998;391(6669):806-811.

Fisher et al., Inhibition of MDR1 expression with altritol-modified siRNAs. Nucleic Acids Res. 2007;35(4)1064-1074.

Gautam et al., Transgene Expression in Mouse Airway Epithelium by Aerosol Gene Therapy with PEI-DNA Complexes. Mol Ther. Apr. 2001;3(4):551-556.

Gerhart et al., Health and psychosocial issues of individuals with incomplete and resolving spinal cord injuries. Paraplegia. Apr. 1992;30(4):282-287.

Gil and Esteban, Induction of apoptosis by the dsRNA-dependent protein kinase (PKR): Mechanism of action. Apoptosis. Apr. 2000;5(2):107-114.

Grimm and Kay, Therapeutic application of RNAi: Is mRNA targeting finally ready for prime time? J Clin Invest. Dec. 2007;117(12):3633-3641.

Herdewijn et al., Properties of Oligonucleotides with Six Membered Carbohydrate Mimics and a 1,4-Relationship between the Base Moiety and the Hydroxymethyl Group. Nucleosides & Nucleotides 1999;18:1371-1376.

International Search Report and Written Opinion issued in PCT/US2012/027174 on Aug. 21, 2012.

Jensen et al., Unlocked nucleic acid (UNA) and UNA derivatives: Thermal denaturation studies. Nucleic Acids Symp Ser (Oxf). 2008;(52):133-134.

Kim and Chung, An experimental model for peripheral neuropathy produced by segmental spinal nerve ligation in the rat. Pain. Sep. 1992;50(3):355-363.

Kim and Rossi, RNAi mechanisms and applications. Biotechniques. Apr. 2008;44(5):613-616.

(56) References Cited

OTHER PUBLICATIONS

Krupnick et al., Orthotopic Mouse Lung Transplantation as Experimental Methodology to Study Transplant and Tumor Biology. Nat Protoc. 2009;4(1):86-93.

Lee et al., The nuclear RNase III Drosha initiates microRNA processing. Nature. Sep. 25, 2003;425(6956):415-419.

Lee and Christie, Primary Graft Dysfunction. Proc Am Thorac Soc. Jan. 15, 2009;6(1):39-46.

Levenkova et al., Gene specific siRNA selector. Bioinformatics. Feb. 12, 2004;20(3):430-432.

Lewis et al., Efficient delivery of siRNA for inhibition of gene expression in postnatal mice. Nat Genet. Sep. 2002;32(1):107-108.

Li et al., The dendritic cell mannose receptor mediates allergen internalization and maturation involving notch 1 signalling. Clin Exp Immunol. Nov. 2010;162(2):251-261.

McManus and Sharp, Gene Silencing in Mammals by Small Interfering RNAs. Nat Rev Genet. Oct. 2002;3(10):737-747.

Nishikura, A Short Primer on RNAi: RNA-Directed RNA Polymerase Acts as a Key Catalyst. Cell. Nov. 16, 2001;107(4):415-418.

Okazaki et al., A Mouse Model of Orthotopic Vascularized Aerated Lung Transplantation. Am J Transplant. Jun. 2007;7(6):1672-1679.

Paddison and Hannon, siRNAs and shRNAs: Skeleton keys to the human genome. Curr Opin Mol Ther. Jun. 2003;5(3):217-224.

Perez-Perez et al., Synthesis and Antiviral Activity of 2-Deoxy-1,5-Anhydro-D-Mannitol Nucleosides Containing a Pyrimidine Base Moiety. Bioorg. and Medicinal Chem Letters 1996;6:1457-1460.

Reich et al., Small interfering RNA (siRNA) targeting VEGF effectively inhibits ocular neovascularization in a mouse model. Mol Vis. May 30, 2003;9:210-216.

Scaringe et al., Chemical synthesis of biologically active oligoribonucleotides using beta-cyanoethyl protected ribonucleoside phosphoramidites. Nucleic Acids Res. Sep. 25, 1990;18(18):5433-5441.

Shabarova et al., Chemical ligation of DNA: the first non-enzymatic assembly of a biologically active gene. Nucleic Acids Res. Aug. 11, 1991;19(15):4247-4251.

Shahiwala and Misra, A Preliminary Pharmacokinetic Study of Liposomal Leuprolide Dry Powder Inhaler: A Technical Note. AAPS PharmSciTech. Oct. 24, 2005;6(3):E482-6.

Shen et al., Gene silencing by adenovirus-delivered siRNA. FEBS Lett. Mar. 27, 2003;539(1-3):111-114.

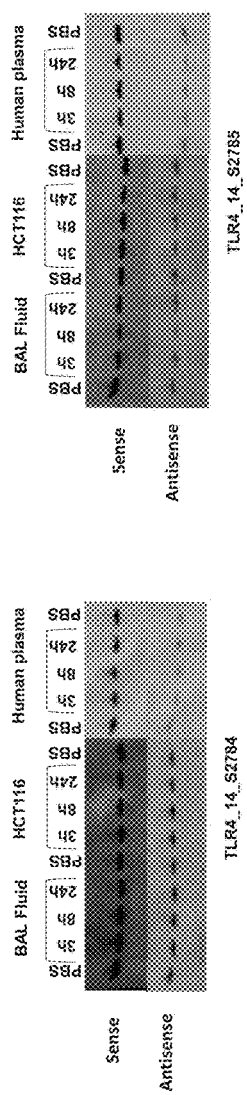

OLIGONUCLEOTIDE MODULATORS OF THE TOLL-LIKE RECEPTOR PATHWAY

RELATED APPLICATIONS

This application claims priority to U.S. Provisional Application No. 61/448,707 filed Mar. 3, 2011; is a National Stage Entry of International Application No. PCT/US2012/027174 filed Mar. 1, 2012; and is a Continuation In Part of U.S. application Ser. No. 14/002,901 filed Oct. 3, 2013, the disclosures of which are all incorporated herein by reference in their entirety.

SEQUENCE LISTING

The instant application contains a Sequence Listing, which is entitled 233-PCT1_ST25.txt, created on Feb. 28, 2012 and 3,908 kb in size, and is hereby incorporated by reference in its entirety.

FIELD OF THE INVENTION

Provided herein are nucleic acid molecules, pharmaceutical compositions comprising same and methods of use thereof for the inhibition of mammalian target genes TLR2, TLR4, MYD88, TICAM1 and TIRAP in the Toll-like receptor (TLR) pathway. Specific compounds include unmodified and chemically modified dsRNA and siRNA oligonucleotides and compositions comprising same.

BACKGROUND OF THE INVENTION

Oligonucleotide sequences and nucleotide modifications useful in generating dsRNA have been described by the applicants of the present disclosure in, inter alia, US Patent Publication Nos. US 20080293655, US 20090162365, US 20100292301 and US 20110112168 and PCT Patent Publication Nos. WO 2011/066475, WO 2011/084193 and WO 2011/085056, hereby incorporated by reference in their entirety.

There remains a need for active and effective dsRNA therapeutic agents which exhibit enhanced knock down activity, increased stability and/or reduced off target effects useful in modulating the Toll-like receptor pathway.

SUMMARY OF THE INVENTION

Provided herein are compositions, methods and kits useful for modulating expression of target genes in the Toll-like receptor pathway. In various aspects provided are nucleic acid molecule inhibitors of a mammalian gene selected from the group consisting of TLR2, TLR4, MYD88, TICAM1 and TIRAP, having mRNA polynucleotide sequences set forth in SEQ ID NOS: 1-12 which include SEQ ID NO:1 (TLR2 mRNA); SEQ ID NO:2-4 (TLR4 mRNA), SEQ ID NO:5-9 (MYD88 mRNA), SEQ ID NO:10 (TICAM1 mRNA) or SEQ ID NO:11-12 (TIRAP mRNA).

In particular embodiments provided herein are novel double stranded nucleic acid molecules, in particular double-stranded RNA (dsRNA), that inhibit, down-regulate or reduce expression of a gene selected from the group consisting of TLR2, TLR4, MYD88, TICAM1 and TIRAP, and pharmaceutical compositions comprising one or more such oligonucleotides or a vector capable of expressing the oligonucleotide. Further provided herein are methods for treating inflammation and inflammatory diseases and graft rejection associated with organ transplantation, such as lung transplantation, in which expression of one or more of the TLR2, TLR4, MYD88, TICAM1 and TIRAP genes is associated with the etiology or progression of inflammation and graft rejection associated with organ transplantation.

In some aspects and embodiments the double stranded oligonucleotides are chemically modified dsRNA compounds. In some embodiments the dsRNA sense and antisense oligonucleotides are selected from sense oligonucleotides and corresponding antisense oligonucleotides set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP).

In some embodiments, provided herein is a nucleic acid molecule having the following double-stranded Structure:

$$\text{5' (N)x-Z 3' (antisense strand)} \quad (A1)$$
$$\text{3' Z'-(N')y-z" 5' (sense strand)}$$

wherein each N and N' is a nucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present independently comprises 1-5 consecutive nucleotides or non-nucleotide moieties or a combination thereof covalently attached at the 3' terminus of the strand in which it is present;

wherein z" may be present or absent, but if present is a capping moiety covalently attached at the 5' terminus of (N')y;

wherein each of x and y is independently an integer between 18 and 25;

wherein the sequence of (N')y is complementary to the sequence of (N)x and (N)x includes an antisense sequence to a target RNA set forth in any one of SEQ ID NOS:1-12.

In some embodiments the covalent bond joining each consecutive N or N' is a phosphodiester bond.

In some embodiments x=y and each of x and y is independently 19, 20, 21, 22 or 23. In various embodiments x=y=19.

In some embodiments the sense strand oligonucleotide and the antisense strand oligonucleotide are selected from the oligonucleotide pairs set forth in SEQ ID NOS:13-3060 to target TLR2; SEQ ID NOS:5847-8612 to target TLR4; SEQ ID NOS:12145-13924 to target MYD88; SEQ ID NOS:16333-16882 to target TICAM1; or SEQ ID NOS:18243-19046 to target TIRAP.

In certain preferred embodiments, the sense strand and the antisense strand of a double-stranded nucleic acid molecule (e.g., a siNA molecule) as disclosed herein include sequences corresponding to any one of the sense sequences and antisense sequences set forth in SEQ ID NOS:13-1448 or 1449-3060 (targeting TLR2); or SEQ ID NOS:5847-8320 or 8321-8612 (targeting TLR4); or SEQ ID NOS:12145-13108 or 13109-13924 (targeting MYD88); or SEQ ID NOS:16333-16866 or 16867-16882 (targeting TICAM1); or SEQ ID NOS:18243-19010 or 19011-19046 (targeting TIRAP).

In some embodiments the sense strand and the antisense strand of a double-stranded nucleic acid molecule are selected from the sequence pairs set forth in TLR2_25, TLR2_28, TLR2_42, TLR2_43 and TLR2_47. In some embodiments the sense strand and the antisense strand are selected from the sequence pairs set forth in TLR2_25 (SEQ ID NOS:20607 and 20614), TLR2_28 (SEQ ID NOS:20608 and 20615), TLR2_42 (SEQ ID NOS:20609 and 20616), TLR2_43 (SEQ ID NOS:20610 and 20617) and TLR2_47 (SEQ ID NOS:20611 and 20618).

In some embodiments the nucleic acid molecule (e.g., a siNA molecule) as disclosed herein include the sequence pair set forth in TLR2_25 (SEQ ID NOS:20607 and 20614). In some embodiments the nucleic acid molecule (e.g., a siNA molecule) as disclosed herein include the sense and antisense strands of the sequence pair set forth in TLR2_28 (SEQ ID NOS:20608 and 20615). In some embodiments the nucleic acid molecule (e.g., a siNA molecule) as disclosed herein includes the sequence pair set forth in TLR2_42 (SEQ ID NOS:20609 and 20616). In some embodiments the nucleic acid molecule (e.g., a siNA molecule) as disclosed herein includes the sense and the antisense strands of the sequence pair set forth in TLR2_43 (SEQ ID NOS:20610 and 20617). In some embodiments the nucleic acid molecule (e.g., a siNA molecule) as disclosed herein includes the sense and the antisense strands of the sequence pair set forth in TLR2_47 (SEQ ID NOS:20611 and 20618).

In some embodiments the sense strand and the antisense strand of a double-stranded nucleic acid molecule are selected from the sequence pairs set forth in TLR4_08, TLR4_10, TLR4_11, TLR4_14, TLR4_15, TLR4_28, TLR4_29, TLR4_31 and TLR4_33. In some embodiments the sense strand and the antisense strand are selected from the sequence pairs set forth in TLR4_08 (SEQ ID NOS: 20621 and 20630), TLR4_10 (SEQ ID NOS:20622 and 20631), TLR4_11 (SEQ ID NOS:20623 and 20632), TLR4_14 (SEQ ID NOS:20624 and 20633), TLR4_15 (SEQ ID NOS:20625 and 20634), TLR4_28 (SEQ ID NOS:20626 and 20635), TLR4_29 (SEQ ID NOS:20627 and 20636), TLR4_31 (SEQ ID NOS:20628 and 20637) and TLR4_33 (SEQ ID NOS:20629 and 20638).

In some embodiments the nucleic acid molecule (e.g., a siNA molecule) as disclosed herein includes the sequence pair set forth in TLR4_08 (SEQ ID NOS:20621 and 20630). In some embodiments the nucleic acid molecule (e.g., a siNA molecule) as disclosed herein includes the sense and the antisense strands of the sequence pair set forth in TLR4_10 (SEQ ID NOS:20622 and 20631). In some embodiments the nucleic acid molecule (e.g., a siNA molecule) as disclosed herein includes the sequence pair set forth in TLR4_11 (SEQ ID NOS:20623 and 20632). In some embodiments the nucleic acid molecule (e.g., a siNA molecule) as disclosed herein includes the sense and the antisense strands of the sequence pair set forth in TLR4_14 (SEQ ID NOS:20624 and 20633). In some embodiments the nucleic acid molecule (e.g., a siNA molecule) as disclosed herein includes the sense and the antisense strands of the sequence pair set forth in TLR4_15 (SEQ ID NOS:20625 and 20634). In some embodiments the nucleic acid molecule (e.g., a siNA molecule) as disclosed herein includes the sequence pair set forth in TLR4_28 (SEQ ID NOS:20626 and 20635). In some embodiments the nucleic acid molecule (e.g., a siNA molecule) as disclosed herein includes the sense and the antisense strands of the sequence pair set forth in TLR4_29 (SEQ ID NOS:20627 and 20636). In some embodiments the nucleic acid molecule (e.g., a siNA molecule) as disclosed herein includes the sequence pair set forth in TLR4_31 (SEQ ID NOS:20628 and 20637). In some embodiments the nucleic acid molecule (e.g., a siNA molecule) as disclosed herein include the sense and the antisense strands of the sequence pair set forth in TLR4_33 (SEQ ID NOS:20629 and 20638).

According to one aspect, the present invention provides a double stranded nucleic acid molecule comprising a sense strand and an antisense strand described as the sequence pair set forth as TLR4_14 (SEQ ID NOS: 20624 and 20633, respectively), also referred to herein as "the TLR4_14 double stranded nucleic acid molecule of the invention".

According to some embodiments, the present invention provides a double stranded nucleic acid molecule (such as, but not limited to, an siNA molecule, e.g. an siRNA molecule) comprising a sense strand and an antisense strand described as the sequence pair set forth in TLR4_14 (SEQ ID NOS:20624 and 20633, respectively). Each possibility represents a separate embodiment of the present invention.

According to some embodiments, the TLR4_14 double stranded nucleic acid molecule of the invention is a double stranded nucleic acid molecule having the following structure:

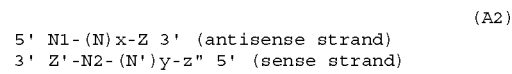

```
5'  N1-(N)x-Z        3'  (antisense strand)
3'  Z'-N2-(N')y-z"   5'  (sense strand)
``` wherein each N2, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 24;

wherein the sequence of (N')y is complementary to the sequence of (N)x and (N)x is complementary to a consecutive sequence in a target RNA set forth in any one of SEQ ID NO:2-4 (TLR4 mRNA);

wherein N1 is an unmodified or modified ribonucleotide covalently bound to (N)x and mismatched to the target RNA;

wherein z" may be present or absent, but if present is a capping moiety covalently attached at the 5' terminus of N2-(N')y;

wherein each of Z and Z' is independently present or absent, but if present is independently 1-5 consecutive nucleotides, consecutive non-nucleotide moieties or a combination thereof covalently attached at the 3' terminus of the strand in which it is present; and wherein the sequence of N1-(N)x is set forth in SEQ ID NO: 20633. According to some embodiments, at least one of N1, N2, N or N' comprises a modified nucleotide or an unconventional moiety. Each possibility represents a separate embodiment of the present invention.

According to some embodiments, N1-(N)x comprises at least one pyrimidine ribonucleotide and wherein at least one of the pyrimidine ribonucleotides in N1-(N)x comprises a 2' sugar modified pyrimidine ribonucleotide. According to some embodiments, the 2' sugar modified ribonucleotide comprises a 2'-OMe sugar modified ribonucleotide.

According to some embodiments, x=18, wherein the ribonucleotides in positions 1, 3, 5, 15 and 17 (5'>3') of N1-(N)x comprise 2'-OMe sugar modified ribonucleotides; and wherein the ribonucleotides in positions 2, 4, 6, 7, 8, 9, 10, 11, 12, 13, 14, 16, 18 and 19 (5'>3') of N1-(N)x comprise unmodified ribonucleotides.

According to some embodiments, at least one of the ribonucleotides in positions 5, 6, 7, 8, or 9 from the 5' terminus of the antisense strand is selected from the group consisting of: a threose nucleic acid (TNA) moiety, a 2'5' nucleotide, a mirror nucleotide, a UNA or a combination thereof. Each possibility represents a separate embodiment of the present invention. According to some embodiments, the ribonucleotide in position 7 of N1-(N)x (5'>3') comprises a 2'5' nucleotide.

According to some embodiments, N1-(N)x comprises a phosphate group on the 5' terminus of the antisense strand; and wherein Z is present and is a C3Pi-C3Pi non-nucleotide moiety covalently attached to the 3' terminus of N1-(N)x.

According to some embodiments, y=18, wherein the ribonucleotides in positions 1, 3, 6, 8, 10, 14 and 18 (5'>3') of N2-(N')y comprise 2'-OMe sugar modified ribonucleotides; and wherein the ribonucleotides in positions 2, 4, 5, 7, 9, 11, 12, 13, 15, 16, 17 and 19 (5'>3') of N2-(N')y comprise unmodified ribonucleotides.

According to other embodiments, y=18, wherein the ribonucleotides in positions 1, 2, 6, 8, 10, 12, 14 and 18 (5'>3') of N2-(N')y comprise 2'-OMe sugar modified ribonucleotides; and wherein the ribonucleotides in positions 3, 4, 5, 7, 9, 11, 13, 15, 16, 17 and 19 (5'>3') of N2-(N')y comprise unmodified ribonucleotides.

According to other embodiments, z" is present and is a C3 moiety covalently attached at the 5' terminus of N2-(N')y; and wherein Z' is present and is 1-5 consecutive nucleotide moieties, 1-5 consecutive non-nucleotide moieties or a combination thereof covalently attached to the 3' terminus of N2-(N')y. Each possibility represents a separate embodiment of the present invention.

According to some embodiments, both Z and Z' are present and each is independently 1-5 consecutive nucleotide moieties, 1-5 consecutive non-nucleotide moieties or a combination thereof covalently attached at the 3' terminus of the strand in which it is present. Each possibility represents a separate embodiment of the present invention.

According to some embodiments, the present invention provides a method for the treatment of a subject in need of treatment for a disease or disorder or symptom or condition associated with the expression of a target gene comprising administering to the subject an amount of the TLR4_14 double stranded nucleic acid molecule of the invention, in an amount effective to down regulate gene expression, wherein the gene encodes a RNA having a polynucleotide sequence as set forth in any one of SEQ ID NO:2-4 (TLR4 mRNA).

According to some embodiments, the disease or injury is selected from the group consisting of: chronic or acute aseptic inflammation, neuropathic pain, primary graft failure, ischemia-reperfusion injury, reperfusion injury, reperfusion edema, allograft dysfunction, pulmonary reimplantation response and primary graft dysfunction (PGD) in organ transplantation. Each possibility represents a separate embodiment of the present invention. According to some embodiments, the disease or injury comprises primary graft dysfunction (PGD) in organ transplantation. According to some embodiments, the organ transplantation comprises lung transplantation.

In some embodiments the sense strand and the antisense strand are selected from the sequence pair set forth in MYD88_11. In some embodiments the antisense strand and the sense strand are selected from the sequence pair set forth in MYD88_11 (SEQ ID NOS:12178 and 12660). In some embodiments the nucleic acid molecule (e.g., a siNA molecule) as disclosed herein includes the sequence pair set forth in MYD88_11 (SEQ ID NOS:12178 and 12660).

In some embodiments the sense strand and the antisense strand are selected from the sequence pair set forth in TICAM1_20. In some embodiments the sense strand and the antisense strand are the sequence pair set forth in TICAM1_20 (SEQ ID NOS:20644 and 20655). In some embodiments the nucleic acid molecule (e.g., a siNA molecule) as disclosed herein includes the sequence pair set forth in TICAM1_20 (SEQ ID NOS:20644 and 20655).

In some embodiments the sense strand and the antisense strand are selected from the sequence pair set forth in TIRAP_16. In some embodiments the antisense strand and the sense strand are selected from the sequence pair set forth in TIRAP_16 (SEQ ID NOS:20661 and 20673). In some embodiments the nucleic acid molecule (e.g., a siNA molecule) as disclosed herein includes the sequence pair set forth in TIRAP_16 (SEQ ID NOS:20661 and 20673).

In various embodiments the double-stranded molecule comprises a mismatch to the target mRNA at the 5' terminal nucleotide of the guide strand (antisense strand).

Accordingly provided are double-stranded nucleic acid molecules having the following Structure:

(A2)

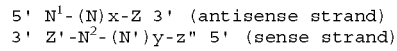

5'  $N^1$-(N)x-Z 3'  (antisense strand)
3'  Z'-$N^2$-(N')y-z" 5'  (sense strand)

wherein each $N^2$, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 24;

wherein the sequence of (N')y is complementary to the sequence of (N)x and (N)x is complementary to a consecutive sequence in a target RNA selected from TLR2, TLR4, MYD88, TICAM, and TIRAP;

wherein $N^1$ is covalently bound to (N)x and is mismatched to a target RNA or is a complementary DNA moiety to the target RNA;

wherein $N^1$ is a moiety selected from the group consisting of unmodified or modified nucleotides selected from uridine (rU), deoxyribouridine (dU), ribothymidine (rT), deoxyribothymidine (dT), adenosine (rA) and deoxyadenosine (dA);

wherein z" may be present or absent, but if present is a capping moiety covalently attached at the 5' terminus of $N^2$-(N')y; and wherein each of Z and Z' is independently present or absent, but if present is independently 1-5 consecutive nucleotides, consecutive non-nucleotide moieties or a combination thereof covalently attached at the 3' terminus of the strand in which it is present.

In some embodiments the sequence of (N')y is fully complementary to the sequence of (N)x. In various embodiments sequence of $N^2$-(N')y is complementary to the sequence of $N^1$-(N)x. In some embodiments (N)x comprises an antisense that is fully complementary to about 17 to about 24 consecutive nucleotides in a target RNA. In other embodiments (N)x comprises an antisense that is substantially complementary to about 17 to about 39 consecutive nucleotides in a target RNA.

In some embodiments $N^1$ and $N^2$ form at least one hydrogen bond. In some embodiments $N^1$ and $N^2$ form a Watson-Crick base pair. In some embodiments $N^1$ and $N^2$ form a non-Watson-Crick base pair. In some embodiments a base pair is formed between a ribonucleotide and a deoxyribonucleotide.

In some embodiments of Structure A2 x=y=18, x=y=19 or x=y=20. In preferred embodiments x=y=18.

In some embodiments $N^1$ is covalently bound to (N)x and is mismatched to the target RNA. In various embodiments N¹ is covalently bound to (N)x and is a DNA moiety complementary to the target RNA.

In some embodiments N¹ is covalently bound to (N)x and is a DNA moiety complementary to the target RNA.

In some embodiments N¹ is selected from adenosine, deoxyadenosine, deoxyuridine, ribothymidine or deoxythymidine, and the pairing nucleotide in the target RNA is adenosine. In preferred embodiments N¹ selected from adenosine, deoxyadenosine or deoxyuridine.

In some embodiments N¹ is selected from adenosine, deoxyadenosine, uridine, deoxyuridine, ribothymidine or deoxythymidine and the pairing nucleotide in the target RNA is cytidine. In preferred embodiments N¹ is selected from adenosine, deoxyadenosine, uridine or deoxyuridine.

In some embodiments N¹ is selected from an unmodified or modified adenosine, deoxyadenosine, uridine, deoxyuridine, ribothymidine or deoxythymidine and the pairing nucleotide in the target RNA is guanosine. In some embodiments N¹ comprises a 2'-OMe sugar modified adenosine, uridine or ribothymidine. In some embodiments N¹ comprises a 2' fluoro or 2' amino sugar modified adenosine, uridine or ribothymidine.

In preferred embodiments N¹ is selected from adenosine, deoxyadenosine, uridine or deoxyuridine. In some embodiments N¹ is selected from adenosine and deoxyadenosine and N² is uridine and N¹ and N² form a base pair. In some embodiments N¹ is selected from uridine or deoxyuridine and N² is adenosine and N¹ and N² form a base pair.

In some embodiments N¹ is selected from deoxyadenosine, deoxyuridine, ribothymidine or deoxythymidine and wherein the nucleotide in the pairing nucleotide in the target RNA is uridine. In preferred embodiments N¹ selected from deoxyadenosine or deoxyuridine.

In some embodiments N¹ is selected from uridine or deoxyuridine and N² is selected from adenosine or deoxyadenosine and N¹ and N² form a base pair.

In some embodiments N¹ is selected from adenosine or deoxyadenosine and N² is selected from uridine or deoxyuridine and N¹ and N² form a base pair. In other embodiments N¹ is deoxyuridine and N² is adenosine and N¹ and N² form a base pair. In some embodiments N¹ is adenosine and N² is uridine and N¹ and N² form a base pair.

In some embodiments the sense strand oligonucleotide and the antisense strand oligonucleotide are selected from the oligonucleotide pairs set forth in SEQ ID NOS:3061-5260 or 5261-5846 to target TLR2; SEQ ID NOS:8613-12040 or 12041-12144 to target TLR4; SEQ ID NOS:13925-15910 or 15911-16332 to target MYD88; SEQ ID NOS: 16883-18236 or 18237-18242 to target TICAM1 or SEQ ID NOS:19047-20590 or 20591-20606 to target TIRAP.

In some embodiments the sense strand and the antisense strand are selected from the sequence pairs set forth in TLR2_31 and TLR2_34. In some embodiments the sense strand and antisense strand are selected from the sequence pairs set forth in TLR2_31 (SEQ ID NOS:20612 and 20619) and TLR2_34 (SEQ ID NOS:20613 and 20620). In various embodiments N¹ in the antisense strand includes uridine or chemically modified uridine and N² in the sense strand includes riboadenine or a chemically modified riboadenine. In some embodiments the nucleic acid molecule (e.g., a siNA molecule) as disclosed herein includes the sequence pair set forth in TLR2_31 (SEQ ID NOS:20612 and 20619). In some embodiments the nucleic acid molecule (e.g., a siNA molecule) as disclosed herein includes the sense and the antisense strands of the sequence pair set forth in TLR2_34 (SEQ ID NOS:20613 and 20620).

In some embodiments the sense strand and the antisense strand are selected from the sequence pairs set forth in TICAM1_15, TICAM1_16, TICAM1_17, TICAM1_18, TICAM1_19, TICAM1_21, TICAM1_22, TICAM1_23, TICAM1_24, and TICAM1_25. In some embodiments the sense strand and the antisense strand are selected from the sequence pairs set forth in TICAM1_15 (SEQ ID NOS: 20639 and 20650), TICAM1_16 (SEQ ID NOS:20640 and 20651), TICAM1_17 (SEQ ID NOS:20641 and 20652), TICAM1_18 (SEQ ID NOS:20642 and 20653); TICAM1_19 (SEQ ID NOS:20643 and 20654); TICAM1_21 (SEQ ID NOS:20645 and 20656), TICAM1_22 (SEQ ID NOS:20646 and 20657), TICAM1_23 (SEQ ID NOS:20647 and 20658), TICAM1_24 (SEQ ID NOS:20448 and 20659) and TICAM1_25 (SEQ ID NOS:20649 and 20660).

In some embodiments the nucleic acid molecule (e.g., a siNA molecule) as disclosed herein includes the sequence pair set forth in TICAM1_15 (SEQ ID NOS:20639 and 20650). In some embodiments the nucleic acid molecule (e.g., a siNA molecule) as disclosed herein includes the sense and the antisense strands of the sequence pair set forth in TICAM1_16 (SEQ ID NOS:20640 and 20651). In some embodiments the nucleic acid molecule (e.g., a siNA molecule) as disclosed herein includes the sequence pair set forth in TICAM1_17 (SEQ ID NOS:20641 and 20652). In some embodiments the nucleic acid molecule (e.g., a siNA molecule) as disclosed herein includes the sense and the antisense strands of the sequence pair set forth in TICAM1_18 (SEQ ID NOS:20642 and 20653). In some embodiments the nucleic acid molecule (e.g., a siNA molecule) as disclosed herein includes the sequence pair set forth in TICAM1_19 (SEQ ID NOS:20643 and 20654). In some embodiments the nucleic acid molecule (e.g., a siNA molecule) as disclosed herein includes the sense and the antisense strands of the sequence pair set forth in TICAM1_21 (SEQ ID NOS:20645 and 20656). In some embodiments the nucleic acid molecule (e.g., a siNA molecule) as disclosed herein includes the sequence pair set forth in TICAM1_22 (SEQ ID NOS:20646 and 20657). In some embodiments the nucleic acid molecule (e.g., a siNA molecule) as disclosed herein includes the sense and the antisense strands of the sequence pair set forth in TICAM1_23 (SEQ ID NOS:20647 and 20658). In some embodiments the nucleic acid molecule (e.g., a siNA molecule) as disclosed herein includes the sequence pair set forth in TICAM1_24 (SEQ ID NOS:20448 and 20659). In some embodiments the nucleic acid molecule (e.g., a siNA molecule) as disclosed herein includes the sense and the antisense strands of the sequence pair set forth in TICAM1_25 (SEQ ID NOS:20649 and 20660).

In some embodiments the sense strand and the antisense strand are selected from the sequence pairs set forth in TIRAP_17, TIRAP_18, TIRAP_19, TIRAP_20, TIRAP_21, TIRAP_22, TIRAP_23, TIRAP_24, TIRAP_25, TIRAP_26 and TIRAP_27. In some embodiments the sense strand and the antisense strand are selected from the sequence pairs set forth in TIRAP_17 (SEQ ID NOS:20662 and 20674), TIRAP_18 (SEQ ID NOS:20663 and 20675); TIRAP_19 (SEQ ID NOS:20664 and 20676); TIRAP_20 (SEQ ID NOS:20665 and 20677), TIRAP_21 (SEQ ID NOS:20666 and 20678), TIRAP_22 (SEQ ID NOS:20667 and 20679), TIRAP_23 (SEQ ID NOS:20668 and 20680), TIRAP_24 (SEQ ID NOS:20669 and 20681), TIRAP_25 (SEQ ID NOS:20670 and 20682), TIRAP_26 (SEQ ID NOS:20671 and 20683) and TIRAP_27 (SEQ ID NOS:20672 and 20684).

In some embodiments the nucleic acid molecule (e.g., a siNA molecule) as disclosed herein includes the sequence pair set forth in TIRAP_17 (SEQ ID NOS:20662 and 20674). In some embodiments the nucleic acid molecule (e.g., a siNA molecule) as disclosed herein includes the sense and the antisense strands of the sequence pair set forth in TIRAP_18 (SEQ ID NOS:20663 and 20675). In some embodiments the nucleic acid molecule (e.g., a siNA molecule) as disclosed herein includes the sequence pair set forth in TIRAP_19 (SEQ ID NOS:20664 and 20676). In some embodiments the nucleic acid molecule (e.g., a siNA molecule) as disclosed herein includes the sense and the antisense strands of the sequence pair set forth in TIRAP_20 (SEQ ID NOS:20665 and 20677). In some embodiments the nucleic acid molecule (e.g., a siNA molecule) as disclosed herein includes the sequence pair set forth in TIRAP_21 (SEQ ID NOS:20666 and 20678). In some embodiments the nucleic acid molecule (e.g., a siNA molecule) as disclosed herein includes the sense and the antisense strands of the sequence pair set forth in TIRAP_22 (SEQ ID NOS:20667 and 20679). In some embodiments the nucleic acid molecule (e.g., a siNA molecule) as disclosed herein includes the sequence pair set forth in TIRAP_23 (SEQ ID NOS:20668 and 20680). In some embodiments the nucleic acid molecule (e.g., a siNA molecule) as disclosed herein includes the sense and the antisense strands of the sequence pair set forth in TIRAP_24 (SEQ ID NOS:20669 and 20681). In some embodiments the nucleic acid molecule (e.g., a siNA molecule) as disclosed herein includes the sequence pair set forth in TIRAP_25 (SEQ ID NOS:20670 and 20682). In some embodiments the nucleic acid molecule (e.g., a siNA molecule) as disclosed herein includes the sense and the antisense strands of the sequence pair set forth in TIRAP_26 (SEQ ID NOS:20671 and 20683). In some embodiments the nucleic acid molecule (e.g., a siNA molecule) as disclosed herein includes the sense and the antisense strands of the sequence pair set forth in TIRAP_27 (SEQ ID NOS:20672 and 20684).

In various embodiments the double stranded nucleic acid molecules are generated based on the SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP) or preferably oligonucleotide pairs set forth in Tables 1-5, infra, and include one or more of the following modifications according to Structure (A1) and Structure (A2):

a. (N)x=19 or $N^1$-(N)x=19 and in at least one of positions 5, 6, 7, 8, or 9 from the 5' terminus of (N)x or $N^1$-(N)x is selected from a threose nucleic acid (TNA) moiety, a 2'5' nucleotide, a mirror nucleotide, a UNA or an abasic moiety;

b. (N)x=19 or $N^1$-(N)x=19 at least one of the pyrimidine ribonucleotides in (N)x or $N^1$-(N)x comprises a 2' sugar modified ribonucleotide;

c. in (N)x or $N^{1-}$-(N)x, N in positions 11, 13, 15, 17 and 19 comprises 2'-OMe sugar modified ribonucleotides and N in positions 10, 12, 14, 16, and 18 comprises unmodified ribonucleotides;

d. in (N)x or $N^{1-}$-(N)x, N in positions 1, 3, 5, 9, 11, 13, 15, 17 and 19 comprises 2'-OMe sugar modified ribonucleotides and N in positions 2, 4, 6, 8, 10, 12, 14, 16, and 18 comprises unmodified ribonucleotides;

e. in (N)x or $N^{1-}$-(N)x, N in positions 2, 4, 6, 8, 11, 13, 15, 17 and 19 comprises 2'-OMe sugar modified ribonucleotides;

f. Z is covalently attached to the 3' terminus of (N)x or $N^1$-(N)x and includes a non-nucleotide moiety selected from the group consisting of C3OH, C3Pi, C3Pi-C3OH, and C3Pi-C3Pi;

g. N' in at least one of positions 7, 8, 9 or 10 from the 5' terminus of (N')y or $N^2$-(N')y is selected from a threose nucleic acid moiety, a 2'5' nucleotide and pseudoUridine;

h. N' comprises a threose nucleic acid (TNA) moiety or a 2'5' nucleotide in 4, 5, or 6 consecutive positions at the 3' terminal or 3' penultimate positions in (N')y or $N^2$-(N')y;

i. at least one of the pyrimidine ribonucleotides in (N')y or $N^2$-(N')y is a 2' sugar modified ribonucleotide;

j. z" is a cap moiety covalently attached to the 5' terminus of (N')y or $N^2$-(N')y and is selected from an inverted abasic deoxyribose moiety, and inverted abasic ribose moiety, an abasic deoxyribose moiety, an abasic ribose moiety, a C3 moiety as defined hereinbelow, L-DNA, L-RNA;

k. Z' is covalently attached to the 3' terminus of (N')y or $N^2$-(N')y and includes one of C3OH, C3Pi, C3Pi-C3OH, or C3Pi-C3Pi.

In preferred embodiments x=y=19.

In some embodiments the covalent bond joining each consecutive N or N' is a phosphodiester bond. In various embodiments all the covalent bonds are phosphodiester bonds In some embodiments of the double stranded nucleic acid molecules of Structure A1 and Structure A2, N in at least one of positions 5, 6, 7, 8, or 9 from the 5' terminus of the antisense strand [(N)x or $N^1$-(N)x] is selected from a threose nucleic acid (TNA) moiety, a 2'5' nucleotide, a mirror nucleotide, a UNA or a combination thereof. Without wishing to be bound by theory, a double stranded nucleic acid molecule having a threose nucleic acid (TNA) moiety, a 2'5' nucleotide, a mirror nucleotide at any one or more of the aforementioned positions confers to the double stranded molecule increased on-target activity and/or decreased off-target activity and or increased stability to nucleases.

In some embodiments the antisense strand [(N)x of Structure A1 or $N^1$-(N)x of Structure A2] comprises a TNA moiety in position 5, a TNA moiety in position 6, a TNA moiety in position 7, a TNA moiety in position 8, a TNA moiety in position 9, TNA moieties in positions 5-6, TNA moieties in positions 6-7, TNA moieties in positions 7-8, TNA moieties in positions 8-9, TNA moieties in positions 5-7, TNA moieties in positions 6-8, TNA moieties in positions 7-9, TNA moieties in positions 5-8, TNA moieties in positions 6-9 or TNA moieties in positions 5-9.

In some embodiments the antisense strand [(N)x of Structure A1 or $N^1$-(N)x of Structure A2] comprises a 2'-5' nucleotide in position 5, a 2'-5' nucleotide in position 6, a 2'-5' nucleotide in position 7, a 2'-5' nucleotide in position 8, a 2'-5' nucleotide in position 9, 2'-5' nucleotides in positions 5-6, 2'-5' nucleotides in positions 6-7, 2'-5' nucleotides in positions 7-8, 2'-5' nucleotide in positions 8-9, 2'-5' nucleotides in positions 5-7, 2'-5' nucleotides in positions 6-8, 2'-5' nucleotides in positions 7-9, 2'-5' nucleotides in positions 5-8, 2'-5' nucleotides in positions 6-9 or 2'-5' nucleotides in positions 5-9.

In some embodiments the antisense strand [(N)x of Structure A1 or $N^1$-(N)x of Structure A2] comprises a mirror nucleotide in position 5, a mirror nucleotide in position 6, a mirror nucleotide in position 7, a mirror nucleotide in position 8, a mirror nucleotide in position 9, mirror nucleotides in positions 5-6, mirror nucleotides in positions 6-7, mirror nucleotides in positions 7-8, mirror nucleotides in positions 8-9, mirror nucleotides in positions 5-7, mirror nucleotides in positions 6-8, mirror nucleotides in positions 7-9, mirror nucleotides in positions 5-8, mirror nucleotides in positions 6-9 or mirror nucleotides in positions 5-9. In some embodiments the mirror nucleotide comprises L-DNA or L-RNA.

In some embodiments of the double stranded nucleic acid molecules, N' in at least one of positions 9 or 10 from the 5' terminus of the sense strand [(N')y in Structure A1 or N²-(N')y in Structure A2] is selected from a threose nucleic acid (TNA) moiety, a 2'5' nucleotide, a pseudoUridine or a combination thereof. Without wishing to be bound to theory, a double stranded nucleic acid molecule having a threose nucleic acid (TNA) moiety, a 2'5' nucleotide, a pseudoUridine at any one or more of positions 9 or 10 in the sense (passenger) strand confers to the double stranded molecule increased on target activity and/or increased nuclease stability.

In some embodiments (N')y in Structure A1 or N²-(N')y in Structure A2 comprises a threose nucleic acid (TNA) moiety in position 9 and/or in position 10.

In some embodiments (N')y in Structure A1 or N²-(N')y in Structure A2 comprises a 2'5' nucleotide in position 9 and/or in position 10.

In some embodiments (N')y in Structure A1 or N²-(N')y in Structure A2 comprises a pseudoUridine in position 9 and/or in position 10.

In some embodiments of the double stranded nucleic acid molecules, N' comprises 4, 5, or 6 consecutive 2'5' nucleotides at the 3' terminal or penultimate position of the sense strand [(N')y in Structure A1 or N²-(N')y in Structure A2]. Without wishing to be bound to theory, a double stranded nucleic acid molecule having 4, 5, or 6 consecutive 2'5' nucleotides at the 3' terminal or penultimate position of the sense (passenger) strand confers increased nuclease stability to the duplex and or reduced off target effect of the sense (passenger) strand. In some embodiments the sense strand further comprises Z'. In some embodiments Z comprises a C3 moiety (for example C3Pi, C3-OH) or a 3' terminal phosphate (Pi).

In some embodiments of Structure A1 and A2 the sense strand comprises four consecutive 2'5' nucleotides at the 3' terminal or penultimate position. In some embodiments of Structure A1 x=y=19 and (N')y comprises 2'5' nucleotides in positions 15, 16, 17, and 18 or in positions 16, 17, 18, and 19. In some embodiments of Structure A2 x=y=18 and N2-(N')y comprises 2'5' nucleotides in positions 15, 16, 17, and 18 or in positions 16, 17, 18, and 19.

In some embodiments of Structures A1 and A2 the sense strand comprises five consecutive 2'5' nucleotides at the 3' terminal or penultimate position. In some embodiments of Structure A1 x=y=19 and (N')y comprises 2'5' nucleotides in positions 14, 15, 16, 17, and 18 or in positions 15, 16, 17, 18, and 19. In some embodiments of Structure A2 x=y=18 and N2-(N')y comprises 2'5' nucleotides in positions 14, 15, 16, 17, and 18 or in positions 15, 16, 17, 18 and N2.

In some embodiments of Structures A1 and A2 the sense strand comprises six consecutive 2'5' nucleotides at the 3' terminal or penultimate position. In some embodiments of Structure A1 x=y=19 and (N')y comprises 2'5' nucleotides in positions 13, 14, 15, 16, 17, and 18 or in positions 14, 15, 16, 17, 18, and 19. In some embodiments of Structure A2 x=y=18 and N2-(N')y comprises 2'5' nucleotides in positions 13, 14, 15, 16, 17, and 18 or in position 14, 15, 16, 17, 18, and N2.

In some embodiments x=y=19 and the double stranded nucleic acid molecule comprises N in at least one of positions 5, 6, 7, 8, or 9 from the 5' terminus of the antisense strand is selected from a threose nucleic acid moiety, a 2'5' nucleotide or a mirror nucleotide;

N' in at least one of positions 9 or 10 from the 5' terminus of the sense strand is selected from a threose nucleic acid moiety, a 2'5' nucleotide and a pseudoUridine; and At least one pyrimidine ribonucleotide in the antisense strand is a 2'-OMe sugar modified ribonucleotide.

In some embodiments the double stranded molecule comprises a 2'5' nucleotide in position 9 of the antisense strand and a 2'5' nucleotide in position 5 or 6 in the sense strand. In additional embodiments the antisense strand further includes 2'-OMe modified pyrimidine ribonucleotides.

In another embodiment x=y=19 and a double stranded nucleic acid molecule comprises N in at least one of positions 5, 6, 7, 8, or 9 from the 5' terminus of the antisense strand is selected from a threose nucleic acid moiety, a 2'5' nucleotide or a mirror nucleotide; and N' in 4, 5, or 6 consecutive positions starting at the 3' terminal or penultimate position of the sense strand comprises a 2'5' nucleotide.

In some embodiments the double stranded nucleic acid molecule is a double stranded oligonucleotide including dsRNA, siRNA, siNA or a miRNA. In some embodiments (N)x and (N')y comprise oligonucleotide pairs set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP) and preferably include one of the following pairs of sense and antisense strands set forth in TLR2_25 (SEQ ID NOS:20607 and 20614), TLR2_28 (SEQ ID NOS:20608 and 20615), TLR2_42 (SEQ ID NOS:20609 and 20616), TLR2_43 (SEQ ID NOS:20610 and 20617), TLR2_47 (SEQ ID NOS:20611 and 20618), TLR2_31 (SEQ ID NOS:20612 and 20619), TLR2_34 (SEQ ID NOS:20613 and 20620); or TLR4_08 (SEQ ID NOS:20621 and 20630), TLR4_10 (SEQ ID NOS:20622 and 20631), TLR4_11 (SEQ ID NOS: 20623 and 20632), TLR4_14 (SEQ ID NOS:20624 and 20633), TLR4_15 (SEQ ID NOS:20625 and 20634), TLR4_28 (SEQ ID NOS:20626 and 20635), TLR4_29 (SEQ ID NOS:20627 and 20636), TLR4_31 (SEQ ID NOS:20628 and 20637), TLR4_33 (SEQ ID NOS:20629 and 20638); or MYD88_11 (SEQ ID NOS:12178 and 12660); or TICAM1_20 (SEQ ID NOS:20644 and 20655), TICAM1_15 (SEQ ID NOS:20639 and 20650), TICAM1_16 (SEQ ID NOS:20640 and 20651), TICAM1_17 (SEQ ID NOS:20641 and 20652), TICAM1_18 (SEQ ID NOS:20642 and 20653); TICAM1_19 (SEQ ID NOS:20643 and 20654); TICAM1_21 (SEQ ID NOS:20645 and 20656), TICAM1_22 (SEQ ID NOS:20646 and 20657), TICAM1_23 (SEQ ID NOS:20647 and 20658), TICAM1_24 (SEQ ID NOS:20448 and 20659), TICAM1_25 (SEQ ID NOS:20649 and 20660); or TIRAP_16 (SEQ ID NOS:20661 and 20673), TIRAP_17 (SEQ ID NOS:20662 and 20674), TIRAP_18 (SEQ ID NOS:20663 and 20675); TIRAP_19 (SEQ ID NOS:20664 and 20676); TIRAP_20 (SEQ ID NOS:20665 and 20677), TIRAP_21 (SEQ ID NOS:20666 and 20678), TIRAP_22 (SEQ ID NOS:20667 and 20679), TIRAP_23 (SEQ ID NOS:20668 and 20680), TIRAP_24 (SEQ ID NOS:20669 and 20681), TIRAP_25 (SEQ ID NOS:20670 and 20682), TIRAP_26 (SEQ ID NOS:20671 and 20683) and TIRAP_27 (SEQ ID NOS:20672 and 20684).

In some embodiments the double stranded molecule comprises a phosphodiester bond. In various embodiments the double stranded molecule comprises ribonucleotides wherein x=y and wherein x is an integer selected from the group consisting of 19, 20, 21, 22, and 23. In some embodiments x=y=19.

In some embodiments (N)x of Structure 1 or N1-(N)x of Structure A2 comprise unmodified ribonucleotides.

In some embodiments (N)x of Structure 1 or N1-(N)x of Structure A2 comprise modified and unmodified ribonucleotides, each modified ribonucleotide a 2'-OMe sugar modified ribonucleotide, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide. In additional embodiments (N)x comprises modified ribonucleotides in alternating positions wherein each N at the 5' and 3' termini are 2'-OMe sugar modified ribonucleotides and the middle ribonucleotide is not modified, e.g. ribonucleotide in position 10 in a 19-mer strand.

In some embodiments (N)x of Structure 1 or N1-(N)x of Structure A2 consist of single alternating 2'-O methyl (2'-OMe) sugar modified and unmodified ribonucleotides, for example wherein the ribonucleotides at positions 1, 3, 5, 7, 9, 11, 13, 15, 17, and 19 are 2'-OMe sugar modified ribonucleotides. In other embodiments the ribonucleotides at positions 2, 4, 6, 8, 11, 13, 15, 17, and 19 are 2'-OMe sugar modified ribonucleotides and the remaining ribonucleotides are unmodified.

In some embodiments (N')y in Structure A1 or N2-(N')y in Structure A2 comprise at least one unconventional moiety selected from a mirror nucleotide, or a nucleotide joined to an adjacent nucleotide by a 2'-5' internucleotide phosphate bond.

In one embodiment of the above Structure, the compound comprises at least one mirror nucleotide at one or both termini in (N')y in Structure A1 or N2-(N')y in Structure A2. In various embodiments the compound comprises two consecutive mirror nucleotides, one at the 3' penultimate position and one at the 3' terminus in (N')y in Structure A1 or N2-(N')y in Structure A2. In one preferred embodiment x=y=19 and (N')y in Structure A1 or N2-(N')y in Structure A2 comprise an L-deoxyribonucleotide at position 18.

In some embodiments the mirror nucleotide is selected from an L-ribonucleotide and an L-deoxyribonucleotide. In various embodiments the mirror nucleotide is an L-deoxyribonucleotide. In some embodiments y=19 and (N')y in Structure A1 or N2-(N')y in Structure A2 consists of unmodified ribonucleotides at positions 1-17 and 19 and one L-DNA at the 3' penultimate position (position 18). In other embodiments y=19 and (N')y consists of unmodified ribonucleotides at position 1-16 and 19 and two consecutive L-DNA at the 3' penultimate position (positions 17 and 18). In some embodiments (N')y in Structure A1 or N2-(N')y in Structure A2 further include Z', for example C3OH and or z", for example and inverted abasic moiety or an amino moiety.

In another embodiment of the above structure, (N')y in Structure A1 or N2-(N')y in Structure A2 comprises at least two consecutive nucleotide joined together to the next nucleotide by a 2'-5' phosphodiester bond at one or both termini. In certain preferred embodiments in (N')y in Structure A1 or N2-(N')y in Structure A2 the 3' penultimate nucleotide is linked to the 3' terminal nucleotide with a 2'-5' phosphodiester bridge.

In certain preferred embodiments double stranded RNA molecule is a blunt-ended (i.e. z", Z and Z' are absent), double stranded oligonucleotide structure, x=y=19, wherein (N')y in Structure A1 or N2-(N')y in Structure A2 comprises unmodified ribonucleotides in which three consecutive nucleotides at the 3' terminus are joined together by two 2'-5' phosphodiester bonds; and an antisense strand (AS) of alternating unmodified and 2'-OMe sugar-modified ribonucleotides.

In one embodiment the double stranded nucleic acid molecule comprises an antisense strand and a sense strand selected from pairs of oligonucleotides set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the antisense strand includes at least one 2'-OMe sugar modified pyrimidine ribonucleotide; a TNA, 2'-5' ribonucleotide a mirror nucleotide, a UNA or an abasic moiety in at least one of positions 1, 5, 6, or 7 (5'>3'); and a 3' terminal non-nucleotide moiety covalently attached to the 3' terminus; and the sense strand includes at least one 2'5' ribonucleotide or 2'-OMe modified ribonucleotide, and a non-nucleotide moiety covalently attached at the 3' terminus and a cap moiety covalently attached at the 5' terminus.

In one embodiment the double stranded nucleic acid molecule comprises an antisense strand and a sense strand selected from pairs of oligonucleotides in set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the antisense strand includes at least one 2'-OMe sugar modified pyrimidine ribonucleotide, a TNA or 2'-5' ribonucleotide in position 7, and a nucleotide or non-nucleotide moiety covalently attached at the 3' terminus; and the sense strand includes 4-5 consecutive 2'5' ribonucleotides or TNA in the 3' terminal positions 16-19 or 15-19 (5'>3'), a non-nucleotide moiety covalently attached at the 3' terminus and a cap moiety such as an inverted abasic moiety covalently attached at the 5' terminus; and optionally includes a 2'-OMe sugar modified ribonucleotide at position 1 of the antisense strand or a 2'5' ribonucleotide at position 1 of the antisense strand.

In one embodiment the double stranded nucleic acid molecule comprises an antisense strand and a sense strand selected from pairs of oligonucleotides set forth in set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the antisense strand includes at least one 2'-OMe sugar modified pyrimidine ribonucleotide, a 2'-5' ribonucleotide in position 7, and a nucleotide or C3Pi-C3OH non-nucleotide moiety covalently attached at the 3' terminus; and the sense strand includes at least one 2'-OMe sugar modified pyrimidine ribonucleotide, a TNA or 2'5' ribonucleotide at position 9, a C3OH or C3Pi non-nucleotide moiety covalently attached at the 3' terminus and a cap moiety such as an inverted abasic moiety covalently attached at the 5' terminus.

In one embodiment the double stranded nucleic acid molecule comprises an antisense strand and a sense strand selected from pairs of oligonucleotides set forth in set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes at least one 2'-OMe sugar modified pyrimidine ribonucleotide; a nucleotide or non-nucleotide moiety covalently attached at the 3' terminus; and a cap moiety covalently attached at the 5' terminus; and the antisense strand includes at least one 2'-OMe sugar modified ribonucleotide; a TNA or 2'-5' ribonucleotide in at least one of positions 5, 6 or 7; and a nucleotide or non-nucleotide moiety covalently attached at the 3' terminus.

In one embodiment the double stranded nucleic acid molecule comprises an antisense strand and a sense strand selected from pairs of oligonucleotides set forth in set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes at least one 2'-OMe sugar modified pyrimidine ribonucleotide, a nucleotide or non-nucleotide moiety covalently attached at the 3' terminus, and a cap moiety covalently attached at the 5' terminus; and the antisense strand includes at least one 2'-OMe sugar modified ribonucleotide; a TNA or 2'-5' ribonucleotide at position 7; and a nucleotide or non-nucleotide moiety covalently attached at the 3' terminus.

In one embodiment the double stranded nucleic acid molecule comprises an antisense strand and a sense strand selected from pairs of oligonucleotides set forth in set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes at least one 2'-OMe sugar modified pyrimidine ribonucleotide; a C3OH moiety covalently attached at the 3' terminus; and a cap moiety such as an inverted abasic deoxyribonucleotide moiety covalently attached at the 5' terminus; and the antisense strand includes at least one 2'-OMe sugar modified pyrimidine ribonucleotide; a TNA or 2'-5' ribonucleotide at position 7 (5'>3'); and a nucleotide or C3Pi-C3OH non-nucleotide moiety covalently attached at the 3' terminus.

In one embodiment the double stranded nucleic acid molecule comprises an antisense strand and a sense strand selected from pairs of set forth in set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes 2'-5' ribonucleotides in positions at the 3' terminus: a non-nucleotide moiety covalently attached at the 3' terminus and a cap moiety covalently attached at the 5' terminus; and the antisense strand includes at least one 2'-OMe sugar modified ribonucleotide; a TNA or 2'-5' ribonucleotide in at least one of positions 5, 6 or 7 (5'>3') and a nucleotide or non-nucleotide moiety covalently attached at the 3' terminus.

In one embodiment the double stranded nucleic acid molecule comprises an antisense strand and a sense strand selected from pairs of oligonucleotides set forth in set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes 4-5 consecutive TNA or 2'-5' ribonucleotides in positions (5'>3') 15-19 or 16-19, a C3-OH 3' moiety covalently attached at the 3' terminus and a cap moiety such as an inverted abasic deoxyribonucleotide moiety covalently attached at the 5' terminus; and the antisense strand includes at least one 2'-OMe sugar modified pyrimidine ribonucleotide; a TNA or 2'-5' ribonucleotide in position 7 and a nucleotide or C3Pi-C3OH moiety covalently attached at the 3' terminus.

In one embodiment the double stranded nucleic acid molecule comprises an antisense strand and a sense strand selected from pairs of oligonucleotides set forth in set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes at least one 2'-OMe sugar modified pyrimidine ribonucleotide, an optional 2'-5' ribonucleotide in one of position 9 or 10, a non-nucleotide moiety covalently attached at the 3' terminus and a cap moiety covalently attached at the 5' terminus; and the antisense strand includes at least one 2'-OMe sugar modified ribonucleotide, a TNA or 2'5' ribonucleotide in at least one of positions 5, 6, or 7; and a nucleotide or non-nucleotide moiety covalently attached at the 3' terminus.

In one embodiment the double stranded nucleic acid molecule comprises an antisense strand and a sense strand selected from pairs of set forth in set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes at least one 2'-OMe sugar modified pyrimidine ribonucleotide, a 2'-5' ribonucleotide in position 9, a C3OH non-nucleotide moiety covalently attached at the 3' terminus and a cap moiety such as an inverted abasic deoxyribonucleotide moiety covalently attached at the 5' terminus; and the antisense strand includes at least one 2'-OMe sugar modified pyrimidine ribonucleotide, a TNA or 2'5' ribonucleotide in position 6; and a nucleotide or C3Pi-C3OH moiety covalently attached at the 3' terminus.

In one embodiment the double stranded nucleic acid molecule comprises an antisense strand and a sense strand selected from pairs of oligonucleotides set forth in set forth in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra, the sense strand includes at least one 2'-OMe sugar modified pyrimidine ribonucleotide, a C3OH or C3Pi non-nucleotide moiety covalently attached at the 3' terminus and a cap moiety such as an inverted abasic deoxyribonucleotide moiety covalently attached at the 5' terminus; and the antisense strand includes at least one 2'-OMe sugar modified pyrimidine ribonucleotide, a 2'5' ribonucleotide in position 6; and a nucleotide or C3Pi-C3OH moiety covalently attached at the 3' terminus.

In some embodiments the nucleotide moiety covalently attached at the 3' terminus comprises the dinucleotide dTdT.

According to another aspect, the present invention provides a method of generating a double stranded RNA molecule consisting of a sense strand and an antisense strand having oligonucleotide sequences forth in SEQ ID NOS:13-3060 to target TLR2; SEQ ID NOS:5847-8612 to target TLR4; SEQ ID NOS:12145-13924 to target MYD88; SEQ ID NOS:16333-16882 to target TICAM1; or SEQ ID NOS: 18243-19046 to target TIRAP, the method comprising the steps a) synthesizing a sense strand;
b) synthesizing an antisense strand;
c) annealing the sense strand to the antisense strand;
thereby generating a double stranded RNA molecule. In some embodiment the synthesis includes synthesis of a chemically unmodified dsRNA strand. In some embodiments synthesis includes incorporation of modified nucleotides including 2'-OMe sugar modified ribonucleotides or unconventional moieties including 2'5' linked nucleic acid, abasic and inverted abasic moieties and the like.

In some embodiments, neither (N)x nor (N')y are phosphorylated at the 3' and 5' termini. In other embodiments either or both (N)x and (N')y are phosphorylated at the 3' termini.

In another aspect, provided herein are pharmaceutical compositions comprising one or more double stranded molecules as disclosed herein, in an amount effective to inhibit target gene expression, and a pharmaceutically acceptable carrier wherein the target gene is selected from a gene having a mRNA set forth in SEQ ID NOS:1-12.

In another aspect provided is a cell comprising one or more double stranded molecule as disclosed herein in an amount effective to inhibit target gene expression.

In various embodiments the compound comprises an antisense oligonucleotide (N)x and a corresponding sense oligonucleotide, the oligonucleotide pairs set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), or preferably oligonucleotide pairs set forth in Tables 1-5, infra.

In other aspects disclosed are oligonucleotide compounds useful in preventing or treating chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD) in organ transplantation, such as lung transplantation in a subject in need thereof.

In another aspect, provided is a method for the treatment of a subject in need of treatment for a disease or disorder or symptom or condition associated with the disease or disorder, associated with the expression of a target gene comprising administering to the subject an amount of a double stranded molecule as disclosed herein which reduces or inhibits expression of a target gene. In preferred embodiments the double stranded molecule is chemically modified as described herein.

Also provided is a double stranded molecule as described herein for the treatment of a disease or injury selected from chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD) in organ transplantation, such as lung transplantation.

Further provided is a double stranded molecule as described herein for the preparation of a medicament for the treatment of a disease or injury selected from chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD) in organ transplantation, such as lung transplantation.

In other aspects the disclosure relates to methods for treating or preventing the incidence or severity of a post-transplantational (e.g. following lung transplantation) complication selected from, without being limited to, primary graft failure, ischemia-reperfusion injury, reperfusion injury, reperfusion edema, allograft dysfunction, pulmonary reimplantation response and/or primary graft dysfunction (PGD), in a subject in need thereof wherein the complication is associated with expression of a gene selected from a gene set forth in Table A1. Such methods involve administering to a mammal in need of such treatment a prophylactically or therapeutically effective amount of one or more double stranded molecules disclosed herein to inhibit or reduce expression or activity of at least one such gene. In other aspects the disclosure relates to methods for reducing acute or chronic inflammation in a subject in need thereof wherein the inflammation is associated with expression of a gene selected from a gene set forth in Table A1. Such methods involve administering to a mammal in need of such treatment a prophylactically or therapeutically effective amount of one or more double stranded molecules disclosed herein to inhibit or reduce expression or activity of at least one such gene.

In some embodiments posttransplantational complication is present in an organ transplant recipient (such as a lung transplantation recipient) and the target gene is selected from TLR2, TLR4, MYD88, TICAM1 and TIRAP, having mRNA polynucleotide sequences set forth in SEQ ID NOS: 1-12. Sense and antisense oligonucleotide pairs useful in preparing dsRNA for inhibiting expression of TLR2, TLR4, MYD88, TICAM1 and TIRAP are set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP) or preferably oligonucleotide pairs set forth in Tables 1-5, infra.

The methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

This disclosure is intended to cover any and all adaptations or variations of combination of features that are disclosed in the various embodiments herein. Although specific embodiments have been illustrated and described herein, it should be appreciated that the invention encompasses any arrangement of the features of these embodiments to achieve the same purpose. Combinations of the above features, to form embodiments not specifically described herein, will be apparent to those of skill in the art upon reviewing the instant description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

(FIG. 1B) seed-mediated off-target effect of the antisense (guide) strand in various siRNA compounds targeting TLR4 mRNA as measured through average percentage of luciferase activity using the psiCheck system (NC=cells non-treated with siRNA).

FIGS. 2A and 2B are micrographs depicting (FIG. 2A) stability of the TLR4_14_S2784 siRNA compound following incubation of 3 hours, 8 hours or 24 hours in either human plasma, cytosolic extract from HCT 116 cells or BAL fluid; and (FIG. 2B) stability of the TLR4_14_S2785 siRNA compound following incubation of 3 hours, 8 hours or 24 hours in either human plasma, cytosolic extract from HCT 116 cells or BAL fluid. "PBS" relates to each tested siRNA in PBS at time=0 (start of incubation in other media). "Sense" shows the stability of the sense strand (reacted with an antisense probe), "Antisense" shows the stability of the antisense strand (reacted with a sense probe).

DETAILED DESCRIPTION OF THE INVENTION

Figure 1A:
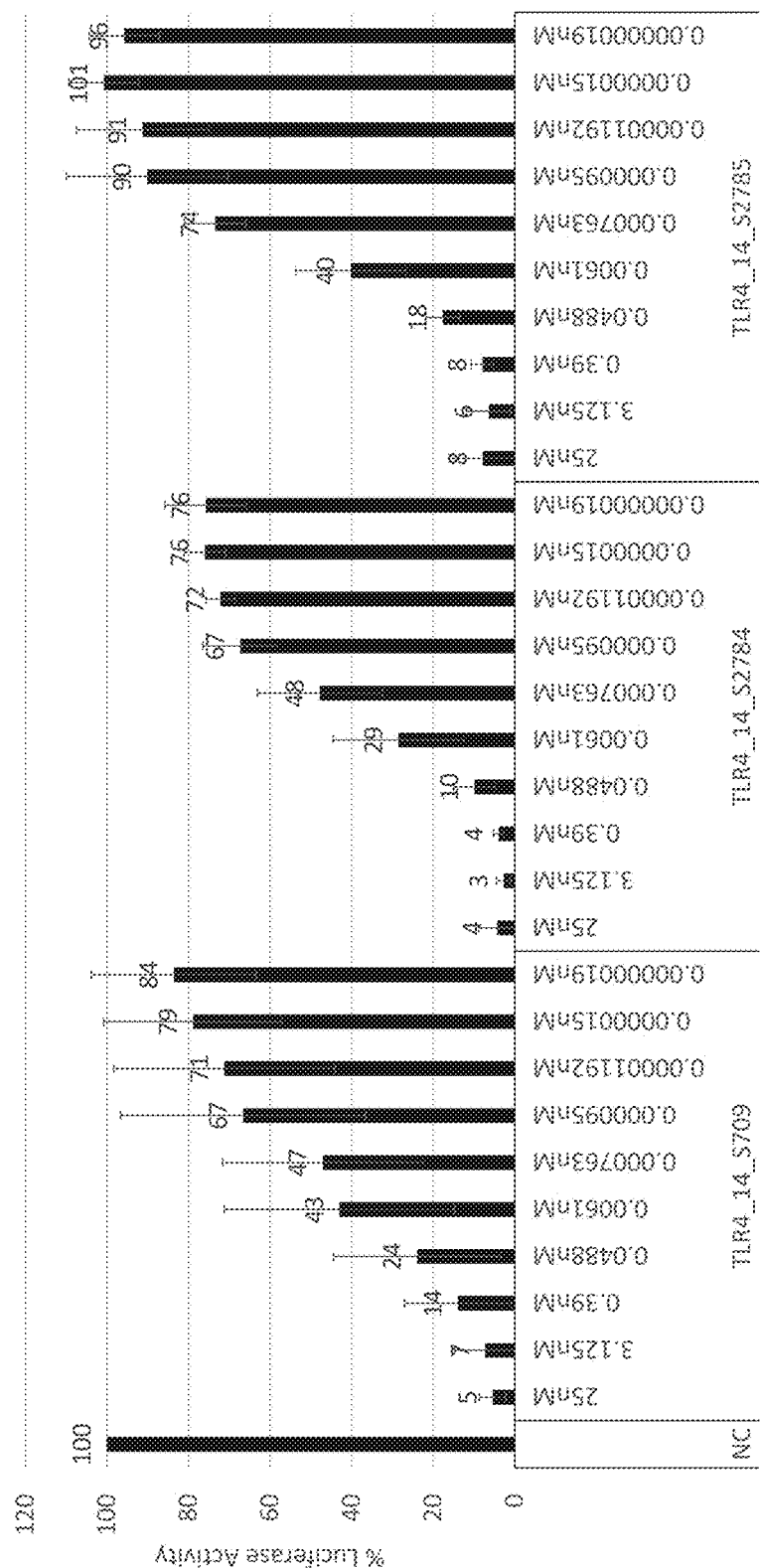
FIGS. 1A and 1B are bar graphs depicting (FIG. 1A) in-vitro knockdown activity of increasing concentrations of various siRNA compounds targeting TLR4 mRNA as measured through average percentage of luciferase activity using the psiCheck system (NC=cells non-treated with siRNA)

The present invention relates in general to compounds which down-regulate expression of certain target genes associated with posttransplantational (e.g. following lung transplantation) complications and their use in treating a subject suffering from diseases or disorders associated with such posttransplantational complications. Inhibition of expression of the one or more of the target genes selected from TLR2, TLR4, MYD88, TICAM1 and TIRAP is now shown to be beneficial in treating a subject suffering from an adverse effect of organ transplantation, for example lung transplantation; more specifically from a posttransplantational (e.g. following lung transplantation) complication selected from, without being limited to, primary graft failure, ischemia-reperfusion injury, reperfusion injury, reperfusion edema, allograft dysfunction, pulmonary reimplantation response and/or primary graft dysfunction (PGD). The present invention relates in particular to small double stranded RNA compounds, such as interfering RNA (siRNA) compounds which inhibit expression of TLR2, TLR4, MYD88, TICAM1 and TIRAP, and to the use of these siRNA compounds in the treatment of certain diseases and disorders. Preferred sense and antisense oligonucleotides useful in the preparation of dsRNA compounds are set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP).

Compounds, compositions and methods for inhibiting target genes having mRNA set forth in any one of SEQ ID NOS:1-12 are discussed herein at length, and any of said compounds and/or compositions are beneficially employed in the treatment of a patient suffering from posttransplantational (e.g. following lung transplantation) complications encountered following transplantation.

Provided herein are compositions and methods for inhibiting expression of a target gene selected from TLR2, TLR4, MYD88, TICAM1 and TIRAP genes in vivo. In general, the method includes administering oligoribonucleotides, such as dsRNA compounds, including small interfering RNAs (i.e., siRNAs) that target mRNA selected from SEQ ID NOS:1 (TLR2 mRNA); SEQ ID NO:2-4 (TLR4 mRNA), SEQ ID NO:5-9 (MYD88 mRNA), SEQ ID NO:10 (TICAM1 mRNA) or SEQ ID NO:11-12 (TIRAP mRNA).

Methods for the delivery of chemically modified dsRNA compounds to a subject are discussed herein at length, and said molecules and/or compositions may be beneficially employed in the treatment of a subject suffering from the diseases and disorders disclosed herein. Treatment may be full or partial and is readily determined by one with skill in the art.

The compounds disclosed herein possess structures and modifications which increase activity, increase stability, minimize toxicity, reduce off target effects and/or reduce immune response when compared to an unmodified dsRNA compound; the novel modifications of the dsRNAs disclosed herein are beneficially applied to double stranded oligonucleotide sequences useful in preventing or attenuating target gene expression, in particular the target genes discussed herein.

Details of the target genes disclosed herein are presented in Table A1, hereinbelow.

TABLE A1

Target genes

| Target gene | SEQ NO, Full name and gi and accession numbers |
|---|---|
| TLR2 | SEQ ID NO: 1 >gi\|68160956\|ref\|NM_003264.3\|*Homo sapiens* Toll-like receptor 2 (TLR2), mRNA |
| TLR4 | SEQ ID NO: 2 >gi\|207028620\|ref\|NM_138554.3\|*Homo sapiens* toll-like receptor 4 (TLR4), transcript variant 1, mRNA |
|  | SEQ ID NO: 3 >gi\|207028451\|ref\|NR_024168.1\|*Homo sapiens* toll-like receptor 4 (TLR4), transcript variant 3, non-coding RNA |
|  | SEQ ID NO: 4 >gi\|207028550\|ref\|NR_024169.1\|*Homo sapiens* toll-like receptor 4 (TLR4), transcript variant 4, non-coding RNA |
| MYD88 | SEQ ID NO: 5 >gi\|197276653\|ref\|NM_002468.4\|*Homo sapiens* myeloid differentiation primary response gene (88) (MYD88), mRNA |
|  | SEQ ID NO: 6 >gi\|289546502\|ref\|NM_001172567.1\|*Homo sapiens* myeloid differentiation primary response gene (88) (MYD88), transcript variant 1, mRNA |

TABLE A1-continued

Target genes

| Target gene | SEQ NO, Full name and gi and accession numbers |
|---|---|
| | SEQ ID NO: 7 >gi|289546580|ref|NM_001172568.1|*Homo sapiens* myeloid differentiation primary response gene (88) (MYD88), transcript variant 3, mRNA |
| | SEQ ID NO: 8 >gi|289546652|ref|NM_001172569.1|*Homo sapiens* myeloid differentiation primary response gene (88) (MYD88), transcript variant 4, mRNA |
| | SEQ ID NO: 9 >gi|289546499|ref|NM_001172566.1|*Homo sapiens* myeloid differentiation primary response gene (88) (MYD88), transcript variant 5, mRNA |
| TICAM1 | SEQ ID NO: 10 >gi|197209874|ref|NM_182919.2|*Homo sapiens* toll-like receptor adaptor molecule 1 (TICAM1, TRIF), mRNA |
| TIRAP | SEQ ID NO: 11 >gi|89111123|ref|NM_148910.2|*Homo sapiens* toll-interleukin 1 receptor (TIR) domain containing adaptor protein (TIRAP), transcript variant 2, mRNA |
| | SEQ ID NO: 12 >gi|89111121|ref|NM_001039661.1|*Homo sapiens* toll-interleukin 1 receptor (TIR) domain containing adaptor protein (TIRAP), transcript variant 3, mRNA |

Table A1 provides the gi (GeneInfo identifier) and accession numbers for exemplary polynucleotide sequences of human mRNA to which the oligonucleotide inhibitors as disclosed herein are directed.

Inhibition of any one of the mRNA polynucleotides set forth in Table A1 is useful in preventing, treating and/or attenuating acute or chronic inflammation, neuropathic pain, posttransplantational complication in organ transplant, (for example lung transplant) patients, such as for example primary graft failure, ischemia-reperfusion injury, reperfusion injury, reperfusion edema, allograft dysfunction, pulmonary reimplantation response and/or primary graft dysfunction (PGD).

In various embodiments, disclosed are chemically modified dsRNA molecules, including small interfering RNAs (siRNAs), and the use of the dsRNAs in the prevention and treatment of various posttransplantational complications in organ transplant, for example lung transplant, patients. Diseases and conditions to be treated are directed to chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD).

Lists of preferred sense and antisense oligonucleotides useful in synthesizing dsRNA compounds are provided in SEQ ID NOS:13-5846 (targeting TLR2), SEQ ID NOS: 5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP). The 18- and 19-mer sense oligonucleotides and corresponding antisense oligonucleotides useful in the synthesis of dsRNA compounds are prioritized based on their score according to a proprietary algorithm as the best sequences for targeting the human gene expression. Molecules, compositions and methods, which inhibit target genes are discussed herein at length, and any of said molecules and/or compositions are beneficially employed in the treatment of a patient suffering from any of said posttransplantational complications.

Structural Design

In one aspect, provided herein are double stranded nucleic acid molecules comprising a sense strand and an antisense strand, wherein at least one strand comprises 1, 2, 3, 4, or 5 non-nucleotide moieties covalently attached at the 3' terminal end; wherein the non-nucleotide moiety is selected from an alkyl (hydrocarbon) moiety or a derivative thereof and a phosphate based moiety. In certain preferred embodiment the non-nucleotide moiety includes an alkyl moiety or an alkyl derivative moiety. In some embodiments the at least one strand is the antisense stand. In preferred embodiments the antisense strand comprises two non-nucleotide moieties covalently attached at the 3' terminal end, including C3-C3; C3-C3-Pi; C3-C3-Ps; idAb-idAb moieties as defined hereinbelow.

In various embodiments provided herein is a double stranded nucleic acid molecule, wherein:
(a) the nucleic acid molecule includes a sense strand and an antisense strand;
(b) each strand of the nucleic acid molecule is independently 17 to 40 nucleotides in length;
(c) a 17 to 40 nucleotide sequence of the antisense strand is complementary to a sequence of a mRNA selected from a mRNA encoding TLR2 (e.g., SEQ ID NO: 1), a mRNA encoding TLR4 (e.g., SEQ ID NOs: 2-4); a mRNA encoding MYD88 (e.g. SEQ ID NO:5-9; a mRNA encoding TICAM1 (e.g. SEQ ID NO:10) or a mRNA encoding TIRAP (e.g. SEQ ID NO:11-12); and
(d) a 17 to 40 nucleotide sequence of the sense strand is complementary to the antisense strand and includes a 17 to 40 nucleotide sequence of a mRNA selected from a mRNA encoding TLR2 (e.g., SEQ ID NO: 1), a mRNA encoding TLR4 (e.g., SEQ ID NOs: 2-4); a mRNA encoding MYD88 (e.g. SEQ ID NO:5-9; a mRNA encoding TICAM1 (e.g. SEQ ID NO:10) or a mRNA encoding TIRAP (e.g. SEQ ID NO:11-12)

In some embodiments, provided are double stranded nucleic acid molecules having the structure (A1):

(A1)
5' $(N)_x$-Z 3' (antisense strand)

3' Z'-$(N')_y$-z" 5' (sense strand)

wherein each of N and N' is a nucleotide which may be unmodified or modified, or an unconventional moiety;
wherein each of (N)x and (N')y is an oligonucleotide in which each consecutive N or N' is joined to the next N or N' by a covalent bond;
wherein at least one of Z or Z' is present and comprises a non-nucleotide moiety covalently attached at the 3' terminus of the strand in which it is present;

wherein z" may be present or absent, but if present is a capping moiety covalently attached at the 5' terminus of (N')y;

wherein each of x and y is independently an integer between 18 and 40;

wherein the sequence of (N')y has complementarity to the sequence of (N)x; and wherein the sequence of (N)x has complementarity to a consecutive sequence in a target RNA set forth in any one of SEQ ID NOS:1-12.

In some embodiments the covalent bond joining each consecutive N or N' is a phosphodiester bond.

In some embodiments x=y=18 to 25 or 19 to 27, for example 18, 19, 20, 21, 22, 23, 24, 25, 26, 27. In some embodiments x=y and each of x and y is 19, 20, 21, 22 or 23. In various embodiments x=y=19.

In some embodiments x=y=19 and one of Z or Z' is present and consists of two non-nucleotide moieties.

In some embodiments x=y=19 and Z' is present and consists of two non-nucleotide moieties.

In preferred embodiments x=y=19 and Z is present and consists two non-nucleotide moieties.

In preferred embodiments x=y=19 and Z is present and consists of two non-nucleotide moieties; and Z' is present and consists of one non-nucleotide moiety.

In additional embodiments x=y=19 and Z and Z' are present and each independently comprises two non-nucleotide moieties.

In some embodiments the double stranded nucleic acid molecules comprise a DNA moiety or a mismatch to the target at position 1 of the antisense strand (5' terminus). Such a structure is described herein. According to one embodiment provided are double stranded nucleic acid molecules having a structure (A2) set forth below:

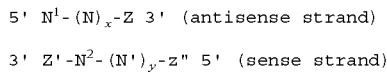

(A2)

5'  $N^1$-$(N)_x$-Z  3' (antisense strand)

3'  Z'-$N^2$-$(N')_y$-z"  5' (sense strand)

wherein each of $N^2$, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y has complementarity to the sequence of (N)x and (N)x has complementarity to a consecutive sequence in a target RNA set forth in SEQ ID NOS:1-12;

wherein $N^1$ is covalently bound to (N)x and is mismatched to the target RNA or is a complementary DNA moiety to the target RNA;

wherein $N^1$ is a moiety selected from the group consisting of natural or modified uridine, deoxyribouridine, ribothymidine, deoxyribothymidine, adenosine or deoxyadenosine;

wherein z" may be present or absent, but if present is a capping moiety covalently attached at the 5' terminus of $N^2$-(N')y; and wherein at least one of Z or Z' is present and comprises a non-nucleotide moiety covalently attached at the 3' terminus of the strand in which it is present.

In some embodiments x=y=17 to 24 or 18 to 23. In preferred embodiments x=y–18.

In some embodiments x=y=18 and Z' is present and consists of two non-nucleotide moieties.

In preferred embodiments x=y=18 and Z is present and consists two non-nucleotide moieties.

In preferred embodiments x=y=18 and Z is present and consists of two non-nucleotide moieties; and Z' is present and consists of one non-nucleotide moiety.

In additional embodiments x=y=18 and Z and Z' are present and each independently comprises two non-nucleotide moieties.

In some embodiments the sequence of (N')y is fully complementary to the sequence of (N)x. In various embodiments sequence of $N^2$-(N')y is complementary to the sequence of $N^1$-(N)x. In some embodiments (N)x comprises an antisense that is fully complementary to about 17 to about 39 consecutive nucleotides in a target RNA. In other embodiments (N)x comprises an antisense that is substantially complementary to about 17 to about 39 consecutive nucleotides in a target RNA.

In some embodiments $N^1$ and $N^2$ form a Watson-Crick base pair. In some embodiments $N^1$ and $N^2$ form a non-Watson-Crick base pair. In some embodiments a base pair is formed between a ribonucleotide and a deoxyribonucleotide.

In some embodiments x=y=18, x=y=19 or x=y=20. In preferred embodiments x=y=18. When x=18 in $N^1$-(N)x, $N^1$ refers to. position 1 and positions 2-19 are included in $(N)_{18}$ When y=18 in $N^2$-(N')y, $N^2$ refers to position 19 and positions 1-18 are included in $(N')_{18}$.

In some embodiments $N^1$ is covalently bound to (N)x and is mismatched to the target RNA. In various embodiments $N^1$ is covalently bound to (N)x and is a DNA moiety complementary to the target RNA.

In some embodiments a uridine in position 1 of the antisense strand is substituted with an $N^1$ selected from adenosine, deoxyadenosine, deoxyuridine (dU), ribothymidine or deoxythymidine. In various embodiments $N^1$ selected from adenosine, deoxyadenosine or deoxyuridine.

In some embodiments guanosine in position 1 of the antisense strand is substituted with an $N^1$ selected from adenosine, deoxyadenosine, uridine, deoxyuridine, ribothymidine or deoxythymidine. In various embodiments $N^1$ is selected from adenosine, deoxyadenosine, uridine or deoxyuridine.

In some embodiments cytidine in position 1 of the antisense strand is substituted with an $N^1$ selected from adenosine, deoxyadenosine, uridine, deoxyuridine, ribothymidine or deoxythymidine. In various embodiments $N^1$ is selected from adenosine, deoxyadenosine, uridine or deoxyuridine.

In some embodiments adenosine in position 1 of the antisense strand is substituted with an $N^1$ selected from deoxyadenosine, deoxyuridine, ribothymidine or deoxythymidine. In various embodiments $N^1$ selected from deoxyadenosine or deoxyuridine.

In some embodiments $N^1$ and $N^2$ form a base pair between uridine or deoxyuridine, and adenosine or deoxyadenosine. In other embodiments $N^1$ and $N^2$ form a base pair between deoxyuridine and adenosine.

In some embodiments the double stranded nucleic acid molecule is a double stranded RNA, such as an siRNA, siNA or a miRNA. The double stranded nucleic acid molecules as provided herein are also referred to as "duplexes".

In certain preferred embodiments x=y=18. In some embodiments $N^1$ and $N^2$ form a Watson-Crick base pair. In other embodiments $N^1$ and $N^2$ form a non-Watson-Crick base pair. In certain embodiments $N^1$ is selected from the group consisting of riboadenosine, modified riboadenosine, deoxyriboadenosine, modified deoxyriboadenosine. In other embodiments N$^1$ is selected from the group consisting of ribouridine, deoxyribouridine, modified ribouridine, and modified deoxyribouridine.

In certain embodiments position 1 in the antisense strand (5' terminus) comprises deoxyribouridine (dU) or adenosine. In some embodiments N$^1$ is selected from the group consisting of riboadenosine, modified riboadenosine, deoxyriboadenosine, modified deoxyriboadenosine and N$^2$ is selected from the group consisting of ribouridine, deoxyribouridine, modified ribouridine, and modified deoxyribouridine. In certain embodiments N$^1$ is selected from the group consisting of riboadenosine and modified riboadenosine and N$^2$ is selected from the group consisting of ribouridine and modified ribouridine.

In certain embodiments N$^1$ is selected from the group consisting of ribouridine, deoxyribouridine, modified ribouridine, and modified deoxyribouridine and N$^2$ is selected from the group consisting of riboadenosine, modified riboadenosine, deoxyriboadenosine, modified deoxyriboadenosine. In certain embodiments N$^1$ is selected from the group consisting of ribouridine and deoxyribouridine and N$^2$ is selected from the group consisting of riboadenosine and modified riboadenosine. In certain embodiments N$^1$ is ribouridine and N$^2$ is riboadenosine. In certain embodiments N$^1$ is deoxyribouridine and N$^2$ is riboadenosine.

In some embodiments of Structure (A2), N$^1$ includes 2'-OMe sugar-modified ribouracil or 2'-OMe sugar-modified riboadenosine. N$^1$ includes 2' fluoro and 2' amino sugar-modified ribouracil or 2' fluoro and 2' amino sugar-modified riboadenosine. In certain embodiments of structure (A2), N$^2$ includes a 2'-OMe sugar modified ribonucleotide or deoxyribonucleotide.

In some embodiments of Structure (A2), N$^1$ includes 2'-OMe sugar-modified ribouracil or 2'-OMe sugar-modified ribocytosine. In certain embodiments of structure (A2), N$^2$ includes a 2'-OMe sugar modified ribonucleotide.

The following table, Table A2 provides non-limiting examples of N$^1$ and corresponding N$^2$.

| Target nucleotide | 5' terminal nucleotide of AS with full match to target | N$^1$ (5' terminal position of AS) | N$^2$ (3' terminal position of SEN) |
|---|---|---|---|
| A | U | rA, dA | rU, dU, rT, dT |
| A | U | dU, rT, dT | rA, dA |
| C | G | rA, dA | rU, dU, rT, dT |
| C | G | rU, dU, rT, dT | rA, dA |
| G | C | rA, dA | rU, dU, rT, dT |
| G | C | rU, dU, rT, dT | rA, dA |
| U | A | dA | rU, dU rT, dT |
| U | A | dU rT, dT | rA, dA |

In some embodiments each of N and N' is an unmodified nucleotide. In some embodiments at least one of N or N' includes a chemically modified nucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' includes a 2'-OMe sugar-modified ribonucleotide.

In some embodiments the sequence of (N')y is fully complementary to the sequence of (N)x. In other embodiments the sequence of (N')y is substantially complementary to the sequence of (N)x.

In some embodiments (N)x includes an antisense sequence that is fully complementary to about 17 to about 39 consecutive nucleotides in a target RNA. In other embodiments (N)x includes an antisense that is substantially complementary to about 17 to about 39 consecutive nucleotides in a target RNA.

In some embodiments the nucleic acid molecules disclosed herein are dsRNA molecules, such as siRNA, siNA or miRNA.

In some embodiments of Structures A1 and A2, Z is present and Z' is absent. In other embodiments Z' is present and Z is absent. In additional embodiments both Z and Z' are present. In some embodiments Z and Z' are present and are identical. In further embodiments Z and Z' are present and are different. In some embodiments Z and Z' are independently 2, 3, 4 or 5 non-nucleotide moieties or a combination of 2, 3, 4, or 5 non-nucleotide moieties and nucleotides. In some embodiments each of Z and or Z' consist of two (2) non-nucleotide moieties covalently attached to the 3' terminus of the dsRNA strand via a phosphodiester bond.

A non-nucleotide moiety is selected from the group consisting of an abasic moiety, an inverted abasic moiety, an alkyl moiety or derivative thereof, and an inorganic phosphate. In some embodiments a non-nucleotide moiety is an alkyl moiety or derivative thereof. In some embodiments the alkyl moiety comprises a terminal functional group selected from the group consisting of an alcohol, a terminal amine, a terminal phosphate and a terminal phosphorothioate moiety.

In some embodiments Z is present and comprises one or more non-nucleotide moieties selected from the group consisting of an abasic moiety, an inverted abasic moiety, hydrocarbon moiety or derivative thereof, and an inorganic phosphate. In some embodiments Z is present and consists of two alkyl moieties or derivatives thereof.

In additional embodiments Z' is present and comprises one or more non-nucleotide moieties selected from the group consisting of an abasic moiety, an inverted abasic moiety, a hydrocarbon moiety, and an inorganic phosphate. In some embodiments Z' is present and comprises one or more alkyl moieties or derivatives thereof.

In some embodiments Z is present and consists of two alkyl moieties or derivatives thereof and Z' is present and consists of a single alkyl moiety or derivative thereof.

In some embodiments each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example 5'>3' dAb-dAb or rAb-rAb or dAb-rAb or rAb-dAb. Each moiety is covalently conjugated to an adjacent moiety via a covalent bond, preferably a phospho-based bond. In some embodiments the phospho-based bond is a phosphorothioate, a phosphonoacetate or a phosphodiester bond.

In some embodiments each of Z and/or Z' independently includes a C2, C3, C4, C5 or C6 alkyl moiety, optionally a C3 [propane, —(CH2)$_3$-] moiety or a derivative thereof e.g. propanol (C3-OH), propanediol, or phosphodiester derivative of propanediol ("C3Pi"). In preferred embodiments each of Z and/or Z' includes two hydrocarbon moieties and in some examples is C3-C3. Each C3 is covalently conjugated to an adjacent C3 via a covalent bond, preferably a phospho-based bond. In some embodiments the phospho-based bond is a phosphorothioate, a phosphonoacetate or a phosphodiester bond.

In some embodiments each of Z and Z' is independently selected from propanol, propyl phosphate, propyl phosphorothioate, combinations thereof or multiples thereof.

Non-limiting exemplary non-nucleotide moieties are set forth in the diagram below:

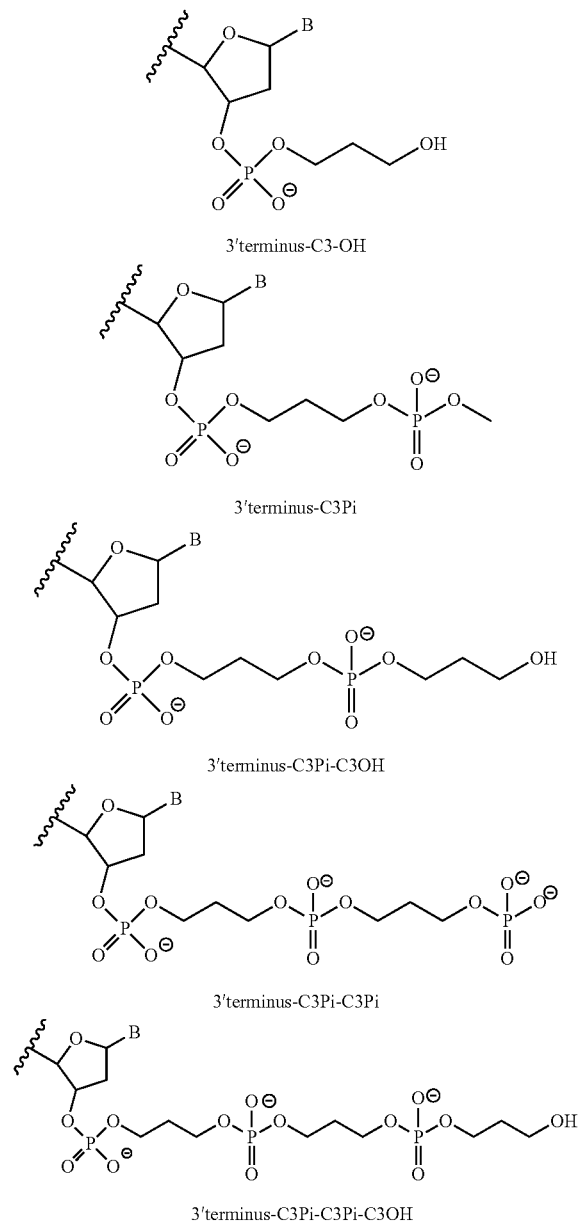

3'terminus-C3-OH

3'terminus-C3Pi

3'terminus-C3Pi-C3OH

3'terminus-C3Pi-C3Pi

3'terminus-C3Pi-C3Pi-C3OH

In some embodiments of Structure A1 and Structure A2 at least one of Z or Z' is present and comprises at least two non-nucleotide moieties covalently attached to the strand in which it is present. In some embodiments each of Z and Z' independently includes a C3 alkyl, C3 alcohol or C3 ester moiety. In some embodiments Z' is absent and Z is present and includes a non-nucleotide C3 moiety. In some embodiments Z is absent and Z' is present and includes a non-nucleotide C3 moiety.

In some embodiments of Structures A1 and A2, each of N and N' is an unmodified nucleotide. In some embodiments at least one of N or N' includes a chemically modified nucleotide or an unconventional moiety. In some embodiments the unconventional moiety is selected from a mirror nucleotide, an abasic ribose moiety and an abasic deoxyribose moiety.

In some embodiments the unconventional moiety is a mirror nucleotide, preferably an L-DNA moiety. In some embodiments at least one of N or N' includes a 2'-OMe sugar-modified ribonucleotide.

In some embodiments the sequence of (N')y is fully complementary to the sequence of (N)x. In other embodiments the sequence of (N')y is substantially complementary to the sequence of (N)x.

In other embodiments the compound of Structure A1 or Structure A2 includes at least one ribonucleotide modified in the sugar residue. In some embodiments the compound includes a modification at the 2' position of the sugar residue. In some embodiments the modification in the 2' position includes the presence of an amino, a fluoro, an alkoxy or an alkyl moiety. In certain embodiments the 2' modification includes an alkoxy moiety, In preferred embodiments the alkoxy moiety is a methoxy moiety (also known as 2'-O-methyl; 2'-OMe; 2'-OCH3). In some embodiments the nucleic acid compound includes 2'-OMe sugar modified alternating ribonucleotides in one or both of the antisense and the sense strands. In other embodiments the compound includes 2'-OMe sugar modified ribonucleotides in the antisense strand, (N)x or $N^1$-(N)x, only. In certain embodiments the middle ribonucleotide of the antisense strand; e.g. ribonucleotide in position 10 in a 19-mer strand is unmodified. In various embodiments the nucleic acid compound includes at least 5 alternating 2'-OMe sugar modified and unmodified ribonucleotides. In additional embodiments the compound of Structure A1 or Structure A2 includes modified ribonucleotides in alternating positions wherein each ribonucleotide at the 5' and 3' termini of (N)x or $N^1$-(N)x are in their sugar residues, and each ribonucleotide at the 5' and 3' termini of (N')y or $N^2$-(N)y are unmodified in their sugar residues.

In some embodiments the double stranded molecule includes one or more of the following modifications
  N in at least one of positions 5, 6, 7, 8, or 9 from the 5' terminus of the antisense strand is selected from a 2'5' nucleotide or a mirror nucleotide;
  N' in at least one of positions 9 or 10 from the 5' terminus of the sense strand is selected from a 2'5' nucleotide and a pseudoUridine; and
  N' in 4, 5, or 6 consecutive positions at the 3' terminus positions of (N')y comprises a 2'5' nucleotide.

In some embodiments the double stranded molecule includes a combination of the following modifications
  the antisense strand includes a 2'5' nucleotide or a mirror nucleotide in at least one of positions 5, 6, 7, 8, or 9 from the 5' terminus; and
  the sense strand includes at least one of a 2'5' nucleotide and a pseudoUridine in positions 9 or 10 from the 5' terminus.

In some embodiments the double stranded molecule includes a combination of the following modifications
  the antisense strand includes a 2'5' nucleotide or a mirror nucleotide in at least one of positions 5, 6, 7, 8, or 9 from the 5' terminus; and
  the sense strand includes 4, 5, or 6 consecutive 2'5' nucleotides at the 3' penultimate or 3' terminal positions.

In some embodiments, the sense strand [(N)x or $N^1$-(N)x] includes 1, 2, 3, 4, 5, 6, 7, 8, or 9 2'-OMe sugar modified ribonucleotides. In some embodiments, the antisense strand includes 2'-OMe modified ribonucleotides at positions 2, 4, 6, 8, 11, 13, 15, 17 and 19. In other embodiments antisense strand includes 2'-OMe modified ribonucleotides at positions 1, 3, 5, 7, 9, 11, 13, 15, 17 and 19. In other embodiments the antisense strand includes 2'-OMe modified ribonucleotides at positions 3, 5, 7, 9, 11, 13, 15, 17 and 19. In some embodiments the antisense strand includes one or more 2'-OMe sugar modified pyrimidines. In some embodiments all the pyrimidine nucleotides in the antisense strand are 2'-OMe sugar modified. In some embodiments the sense strand includes 2'-OMe sugar modified pyrimidines.

In some embodiments of Structure A1 and Structure A2, the sense strand and the antisense strand are independently phosphorylated or unphosphorylated at the 3' terminus and at the 5' terminus. In some embodiments of Structure A1 and Structure A2, the sense strand and the antisense strand are unphosphorylated at the 3' and 5' termini. In other embodiments the sense strand and the antisense strand are phosphorylated at the 3' termini.

In some embodiments of Structure A1 and Structure A2 (N)y includes at least one unconventional moiety selected from a mirror nucleotide, a 2'5' nucleotide and a TNA. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA. In certain embodiments the sense strand comprises an unconventional moiety in position 9 or 10 (from the 5' terminus). In preferred embodiments the sense strand includes an unconventional moiety in position 9 (from the 5' terminus). In some embodiments the sense strand is 19 nucleotides in length and comprises 4, 5, or 6 consecutive unconventional moieties in positions 15, (from the 5' terminus). In some embodiments the sense strand includes 4 consecutive 2'5' ribonucleotides in positions 15, 16, 17, and 18. In some embodiments the sense strand includes 5 consecutive 2'5' ribonucleotides in positions 15, 16, 17, 18 and 19. In various embodiments the sense strand further comprises Z'. In some embodiments Z' includes a C3OH moiety or a C3Pi moiety.

In some embodiments of Structure A1 (N')y includes at least one L-DNA moiety. In some embodiments x=y=19 and (N')y, consists of unmodified ribonucleotides at positions 1-17 and 19 and one L-DNA at the 3' penultimate position (position 18). In other embodiments x=y=19 and (N')y consists of unmodified ribonucleotides at positions 1-16 and 19 and two consecutive L-DNA at the 3' penultimate position (positions 17 and 18). In various embodiments the unconventional moiety is a nucleotide joined to an adjacent nucleotide by a 2'-5' internucleotide phosphate linkage. According to various embodiments (N')y includes 2, 3, 4, 5, or 6 consecutive ribonucleotides at the 3' terminus linked by 2'-5' internucleotide linkages. In one embodiment, four consecutive nucleotides at the 3' terminus of (N')y are joined by three 2'-5' phosphodiester bonds, wherein one or more of the 2'-5' nucleotides which form the 2'-5' phosphodiester bonds further includes a 3'-O-methyl (3'OMe) sugar modification. Preferably the 3' terminal nucleotide of (N')y includes a 2'-OMe sugar modification. In certain embodiments x=y=19 and (N')y includes two or more consecutive nucleotides at positions 15, 16, 17, 18 and 19 include a nucleotide joined to an adjacent nucleotide by a 2'-5' internucleotide bond (2'-5' nucleotide). In various embodiments the nucleotide forming the 2'-5' internucleotide bond includes a 3' deoxyribose nucleotide or a 3' methoxy nucleotide (3' H or 3'OMe in place of a 3' OH). In some embodiments x=y=19 and (N')y includes 2'-5' nucleotides at positions 15, 16 and 17 such that adjacent nucleotides are linked by a 2'-5' internucleotide bond between positions 15-16, 16-17 and 17-18; or at positions, 15, 16, 17, 18, and 19 such that adjacent nucleotides are linked by a 2'-5' internucleotide bond between positions 15-16, 16-17, 17-18 and 18-19 and a 3'OH is available at the 3' terminal nucleotide or at positions 16, 17 and 18 such that adjacent nucleotides are linked by a 2'-5' internucleotide bond between positions 16-17, 17-18 and 18-19. In some embodiments x=y=19 and (N')y includes 2'-5' nucleotides at positions 16 and 17 or at positions 17 and 18 or at positions 15 and 17 such that adjacent nucleotides are linked by a 2'-5' internucleotide bond between positions 16-17 and 17-18 or between positions 17-18 and 18-19 or between positions 15-16 and 17-18, respectively. In other embodiments the pyrimidine ribonucleotides (rU, rC) in (N')y are substituted with nucleotides joined to the adjacent nucleotide by a 2'-5' internucleotide bond. In some embodiments x=y=19 and (N')y comprises five consecutive nucleotides at the 3' terminus joined by four 2'-5' linkages, specifically the linkages between the nucleotides position 15-16, 16-17, 17-18 and 18-19.

In some embodiments x=y=19 and (N')y comprises five consecutive nucleotides at the 3' terminus joined by four 2'-5' linkages and optionally further includes Z' and z' independently selected from an inverted abasic moiety and a C3 alkyl [C3; 1,3-propanediol mono(dihydrogen phosphate)] cap. In some embodiments the C3 alkyl cap is covalently linked to the 3' or 5' terminal nucleotide. In some embodiments the 3' C3 terminal cap further comprises a 3' phosphate. In some embodiments the 3' C3 terminal cap further comprises a 3' terminal hydroxyl group.

In some embodiments x=y=19 and (N')y comprises an L-DNA position 18; and (N')y optionally further includes Z' and z' independently selected from an inverted abasic moiety and a C3 alkyl [C3; 1,3-propanediol mono(dihydrogen phosphate)] cap.

In some embodiments (N')y comprises a 3' terminal phosphate (i.e. phosphorylated at the 3' terminus). In some embodiments (N')y comprises a 3' terminal hydroxyl.

In some embodiments x=y=19 and (N)x includes 2'-OMe sugar modified ribonucleotides at positions 1, 3, 5, 7, 9, 11, 13, 15, 17, 19 or at positions 2, 4, 6, 8, 11, 13, 15, 17, 19. In some embodiments x=y=19 and (N)x includes 2'-OMe sugar modified pyrimidines. In some embodiments all pyrimidines in (N)x include the 2'-OMe sugar modification.

In some embodiments of structure A2 x=y=18 and $N^2$ is a riboadenosine moiety. In some embodiments x=y=18, and $N^2$-(N')y comprises five consecutive nucleotides at the 3' terminus joined by four 2'-5' linkages, specifically the linkages between the nucleotides position 15-16, 16-17, 17-18 and 18-19. In some embodiments the linkages include phosphodiester bonds. In some embodiments x=y=18 and $N^2$-(N')y comprises five consecutive nucleotides at the 3' terminus joined by four 2'-5' linkages and optionally further includes Z' and z' independently selected from an inverted abasic moiety and a C3 alkyl [C3; 1,3-propanediol mono (dihydrogen phosphate)] cap. In some embodiments x=y=18 and $N^2$-(N')y comprises an L-DNA position 18; and (N')y optionally further includes Z' and z' independently selected from an inverted abasic moiety and a C3 alkyl [C3; 1,3-propanediol mono(dihydrogen phosphate)] cap. In some embodiments $N^2$-(N')y comprises a 3' terminal phosphate. In some embodiments $N^2$-(N')y comprises a 3' terminal hydroxyl. In some embodiments x=y=18 and $N^1$-(N)x includes 2'-OMe sugar modified ribonucleotides in positions 1, 3, 5, 7, 9, 11, 13, 15, 17, 19 or in positions 1, 3, 5, 9, 11, 13, 15, 17, 19, or in positions 3, 5, 9, 11, 13, 15, 17, or in positions 2, 4, 6, 8, 11, 13, 15, 17, 19. In some embodiments x=y=18 and $N^1$-(N)x includes 2'-OMe sugar modified ribonucleotides at positions 11, 13, 15, 17 and 19 (from 5' terminus). In some embodiments x=y=18 and N1-(N)x includes 2'-OMe sugar modified ribonucleotides in positions 1, 3, 5, 7, 9, 11, 13, 15, 17, 19 or in positions 3, 5, 7, 9, 11, 13, 15, 17, 19. In some embodiments x=y=18 and $N^1$-(N)x includes 2'-OMe sugar modified ribonucleotides in positions 2, 4, 6, 8, 11, 13, 15, 17, 19.

In some embodiments x=y=18 and $N^1$-(N)x includes 2'-OMe sugar modified pyrimidines. In some embodiments all pyrimidines in (N)x include the 2'-OMe sugar modification. In some embodiments the antisense strand further comprises an L-DNA or a 2'-5' nucleotide in position 5, 6 or 7 (5'>3'). In other embodiments the antisense strand further comprises a ribonucleotide, which generates a 2'5' internucleotide linkage in between the ribonucleotides in positions 5-6 or 6-7 (5'>3').

In additional embodiments $N^{1'}$-(N)x further includes Z wherein Z comprises a non-nucleotide overhang. In some embodiments the non-nucleotide overhang is C3-C3 [1,3-propanediol mono(dihydrogen phosphate)]2.

In some embodiments of Structure A2, (N)y includes at least one L-DNA moiety. In some embodiments x=y=18 and (N')y consists of unmodified ribonucleotides at positions 1-16 and 18 and one L-DNA at the 3' penultimate position (position 17). In other embodiments x=y=18 and (N')y consists of unmodified ribonucleotides at position 1-15 and 18 and two consecutive L-DNA at the 3' penultimate position (positions 16 and 17). In various embodiments the unconventional moiety is a nucleotide joined to an adjacent nucleotide by a 2'-5' internucleotide phosphate linkage. According to various embodiments (N')y includes 2, 3, 4, 5, or 6 consecutive ribonucleotides at the 3' terminus linked by 2'-5' internucleotide linkages. In one embodiment, four consecutive nucleotides at the 3' terminus of (N')y are joined by three 2'-5' phosphodiester bonds, wherein one or more of the 2'-5' nucleotides which form the 2'-5' phosphodiester bonds further includes a 3'-O-methyl (3'OMe) sugar modification. Preferably the 3' terminal nucleotide of (N')y includes a 2'-OMe sugar modification. In certain embodiments x=y=18 and in (N')y two or more consecutive nucleotides at positions 14, 15, 16, 17, and 18 include a nucleotide joined to an adjacent nucleotide by a 2'-5' internucleotide bond. In various embodiments the nucleotide forming the 2'-5' internucleotide bond includes a 3' deoxyribose nucleotide or a 3' methoxy nucleotide. In some embodiments x=y=18 and (N')y includes nucleotides joined to the adjacent nucleotide by a 2'-5' internucleotide bond between positions 15-16, 16-17 and 17-18 or between positions 16-17 and 17-18. In some embodiments x=y=18 and (N')y includes nucleotides joined to the adjacent nucleotide by a 2'-5' internucleotide bond between positions 14-15, 15-16, 16-17, and 17-18 or between positions 15-16, 16-17, and 17-18 or between positions 16-17 and 17-18 or between positions 17-18 or between positions 15-16 and 17-18. In other embodiments the pyrimidine ribonucleotides (rU, rC) in (N')y are substituted with nucleotides joined to the adjacent nucleotide by a 2'-5' internucleotide bond.

In some embodiments of Structure A1 and Structure A2 each N consists of an unmodified ribonucleotide. In some embodiments of Structure A1 and Structure A2 each N' consists of an unmodified nucleotide. In preferred embodiments, at least one of N and N' is a modified ribonucleotide or an unconventional moiety.

In other embodiments the molecule of Structure A1 or Structure A2 includes at least one ribonucleotide modified in the sugar residue. In some embodiments the compound includes a modification at the 2' position of the sugar residue. In some embodiments the modification at the 2' position includes the presence of an amino, a fluoro, an alkoxy or an alkyl moiety. In certain embodiments the 2' modification includes an alkoxy moiety, In preferred embodiments the alkoxy moiety is a methoxy moiety (also known as 2'-O-methyl; 2'-OMe; 2'-OCH3). In some embodiments the nucleic acid compound includes 2'-OMe sugar modified alternating ribonucleotides in one or both of the antisense and the sense strands. In other embodiments the compound includes 2'-OMe sugar modified ribonucleotides in the antisense strand, (N)x or N1-(N)x, only. In certain embodiments the middle ribonucleotide of the antisense strand; e.g. ribonucleotide in position 10 in a 19-mer strand is unmodified. In various embodiments the nucleic acid compound includes at least 5 alternating 2'-OMe sugar modified and unmodified ribonucleotides.

In additional embodiments the compound of Structure A1 or Structure A2 includes modified ribonucleotides in alternating positions wherein each ribonucleotide at the 5' and 3' termini of (N)x or N1-(N)x are modified in their sugar residues, and each ribonucleotide at the 5' and 3' termini of (N')y or $N^2$-(N)y are unmodified in their sugar residues.

In some embodiments, (N)x or $N^1$-(N)x includes 2'-OMe modified ribonucleotides at positions 2, 4, 6, 8, 11, 13, 15, 17 and 19. In other embodiments (N)x (N)x or $N^1$-(N)x includes 2'-OMe modified ribonucleotides at positions 1, 3, 5, 7, 9, 11, 13, 15, 17 and 19. In some embodiments (N)x or $N^1$-(N)x includes 2'-OMe modified pyrimidines. In some embodiments all the pyrimidine nucleotides in (N)x or $N^1$-(N)x are 2'-OMe modified. In some embodiments (N')y or $N^2$-(N')y includes 2'-OMe modified pyrimidines. In additional embodiments the compound of Structure A1 or Structure A2 includes modified ribonucleotides in alternating positions wherein each ribonucleotide at the 5' and 3' termini of (N)x or $N^1$-(N)x are modified in their sugar residues, and each ribonucleotide at the 5' and 3' termini of (N')y or $N^2$-(N)y are unmodified in their sugar residues.

The nucleic acid molecules disclosed herein may have a blunt end on one end, for example when Z and z" are absent or wherein Z' is absent. The nucleic acid molecule may be modified with modified nucleotides or unconventional moieties that may be located at any position along either the sense or antisense strand. The nucleic acid molecule may include about 1, 2, 3, 4, 5, 6, 7, 8, 9, 10, 11, 12, 13, 14, or 15 modified nucleotides. The nucleic acid molecule may include about 1, 2, 3, 4, 5, 6, 7, or 8 unconventional moieties. The nucleic acid molecule may include a group of about 1, 2, 3, 4, 5, 6, 7, or 8, preferably 1, 2, 3 or 4 contiguous modified nucleotides or unconventional moieties. Modified nucleic acids may be present in the sense strand only, the antisense strand only, or in both the sense strand and the antisense strand. In some embodiments the modified nucleotide comprises a 2' sugar modified nucleotide, including 2'O-methyl modified nucleotide, 2'deoxyfluoro modified nucleotide, 2'-amino modified nucleotide. In some embodiments the unconventional moiety comprises a mirror nucleotide (i.e. L-DNA or L-RNA) or a nucleotide able to form a 2'-5' linkage (2'5' nucleotide).

As used herein, the term "duplex region" refers to the region in the double stranded molecule in which two complementary or substantially complementary oligonucleotides form base pairs with one another, typically by Watson-Crick base pairing or by any other manner that allows for a duplex formation. For example, an oligonucleotide strand having 19 nucleotide units can base pair with a complementary oligonucleotide of 19 nucleotide units, or can base pair with 15, 16 17 or 18 bases on each strand such that the "duplex region" consists of 15, 16 17 or 18 base pairs. The remaining base pairs may, for example, exist as 5' and 3' overhangs. Further, within the duplex region, 100% complementarity is not required; substantial complementarity is allowable within a duplex region. The overhang region may consist of nucleotide or non-nucleotide moieties. As disclosed herein at least one overhang region consists of one or more non-nucleotide moieties.

Generic non-limiting nucleic acid molecule patterns are shown below where N'=sense strand nucleotide in the duplex region; z"=5'-capping moiety covalently attached at the 5' terminus of the sense strand; C3=3 carbon non-nucleotide moiety; N=antisense strand nucleotide in the duplex region; idB=inverted abasic deoxyribonucleotide non-nucleotide moiety. Each N, N', is independently modified or unmodified or an unconventional moiety. The sense and antisense strands are each independently 18-40 nucleotides in length. The examples provided below have a duplex region of 19 nucleotides; however, nucleic acid molecules disclosed herein can have a duplex region anywhere between 18 and 40 nucleotides and where each strand is independently between 18 and 40 nucleotides in length. In each duplex the antisense strand (N)x is shown on top. The preferred 19-mer sense sequences and antisense sequences useful in generating dsRNA according to Structure A1 are set forth in SEQ ID NOS:13-3060 (targeting TLR2), SEQ ID NOS:5847-8612 (targeting TLR4), SEQ ID NOS:12145-13924 (targeting MYD88), SEQ ID NOS:16333-16882 (targeting TICAM1) and SEQ ID NOS:18243-19046 (targeting TIRAP). The preferred 18-mer sense sequences and antisense sequences useful in generating dsRNA according to Structure A2 are set forth in SEQ ID NOS: 3061-5846 (targeting TLR2), SEQ ID NOS: 8613-12144 (targeting TLR4), SEQ ID NOS: 13925-16332 (targeting MYD88), SEQ ID NOS:16883-18242 (targeting TICAM1) and SEQ ID NOS: 19047-20606 (targeting TIRAP). Certain preferred oligonucleotide pairs useful in generating dsNA are set forth in Tables 1-5.

In some embodiments a double stranded nucleic acid molecule has the following structure, wherein each N or N' comprises an unmodified or modified ribonucleotide, or an unconventional moiety:

```
5' N N N N N N N N N N N N N N N N N N N-C3Pi-C3Pi
3' N'N'N'N'N'N'N'N'N'N'N'N'N'N'N'N'N'N'N'
or

5' N N N N N N N N N N N N N N N N N N N-C3Pi-C3Pi
3' N'N'N'N'N'N'N'N'N'N'N'N'N'N'N'N'N'N'N'-z"
or

5' N N N N N N N N N N N N N N N N N N N-C3Pi-C3Pi
3' PiC3-PiC3-N'N'N'N'N'N'N'N'N'N'N'N'N'N'N'N'N'N'N'
or

5' N N N N N N N N N N N N N N N N N N N-C3Pi-C3Pi
3' PiC3-PiC3-N'N'N'N'N'N'N'N'N'N'N'N'N'N'N'N'N'N'N'-z"
or

5' N N N N N N N N N N N N N N N N N N N-C3Pi-C3Pi
3' PiC3-N'N'N'N'N'N'N'N'N'N'N'N'N'N'N'N'N'N'N'
or

5' N N N N N N N N N N N N N N N N N N N-C3Pi-C3Pi
3' PiC3-N'N'N'N'N'N'N'N'N'N'N'N'N'N'N'N'N'N'N'-z"
or

5' N N N N N N N N N N N N N N N N N N N-C3Pi-C3Pi
3' HOC3-N'N'N'N'N'N'N'N'N'N'N'N'N'N'N'N'N'N'N'
or

5' N N N N N N N N N N N N N N N N N N N-C3Pi-C3Pi
3' HOC3-N'N'N'N'N'N'N'N'N'N'N'N'N'N'N'N'N'N'N'-z"
or

5' N N N N N N N N N N N N N N N N N N N-aB-aB
3' N'N'N'N'N'N'N'N'N'N'N'N'N'N'N'N'N'N'N'
or

5' N N N N N N N N N N N N N N N N N N N-aB-aB
3' N'N'N'N'N'N'N'N'N'N'N'N'N'N'N'N'N'N'N'-z"
or

5' N N N N N N N N N N N N N N N N N N N-idB-idB
3' aB-aB-N'N'N'N'N'N'N'N'N'N'N'N'N'N'N'N'N'N'N'
or

5' N N N N N N N N N N N N N N N N N N N-aB-aB
3' aB-aB-N'N'N'N'N'N'N'N'N'N'N'N'N'N'N'N'N'N'N'-z"
or

5' N N N N N N N N N N N N N N N N N N N-C3Pi-C3Pi
3' PiC3-N'N'N'N'N'N'N'N'N'N'N'N'N'N'N'N'N'N'N
or

5' N N N N N N N N N N N N N N N N N N N-C3Pi-C3Pi
3' aB-aB-N'N'N'N'N'N'N'N'N'N'N'N'N'N'N'N'N'N'N'
or
```

-continued

```
5' N N N N N N N N N N N N N N N N N N N-C3Pi-C3OH
3' N'N'N'N'N'N'N'N'N'N'N'N'N'N'N'N'N'N'N
or

5' N N N N N N N N N N N N N N N N N N N-C3Pi-C3OH
3' N'N'N'N'N'N'N'N'N'N'N'N'N'N'N'N'N'N'N'-z"
or

5' N N N N N N N N N N N N N N N N N N N-C3Pi-C3OH
3' PiC3-PiC3-N'N'N'N'N'N'N'N'N'N'N'N'N'N'N'N'N'N'N'
or

5' N N N N N N N N N N N N N N N N N N N-C3Pi-C3OH
3' PiC3-PiC3-N'N'N'N'N'N'N'N'N'N'N'N'N'N'N'N'N'N'N'-z"
or

5' N N N N N N N N N N N N N N N N N N N-C3Pi-C3OH
3' PiC3-N'N'N'N'N'N'N'N'N'N'N'N'N'N'N'N'N'N'N'
or

5' N N N N N N N N N N N N N N N N N N N-C3Pi-C3OH
3' PiC3-N'N'N'N'N'N'N'N'N'N'N'N'N'N'N'N'N'N'N'-z"
or

5' N N N N N N N N N N N N N N N N N N N-C3Pi-C3OH
3' HOC3-N'N'N'N'N'N'N'N'N'N'N'N'N'N'N'N'N'N'N'
or

5' N N N N N N N N N N N N N N N N N N N-C3Pi-C3OH
3' HOC3-N'N'N'N'N'N'N'N'N'N'N'N'N'N'N'N'N'N'N'-z"
or

5' N N N N N N N N N N N N N N N N N N N-C3Pi-C3Ps
3' N'N'N'N'N'N'N'N'N'N'N'N'N'N'N'N'N'N'N
or

5' N N N N N N N N N N N N N N N N N N N-C3Pi-C3Ps
3' N'N'N'N'N'N'N'N'N'N'N'N'N'N'N'N'N'N'N'-z"
or

5' N N N N N N N N N N N N N N N N N N N-C3Pi-C3Ps
3' OHC3-PiC3-N'N'N'N'N'N'N'N'N'N'N'N'N'N'N'N'N'N'N'
or

5' N N N N N N N N N N N N N N N N N N N-C3Pi-C3Ps
3' OHC3-PiC3-N'N'N'N'N'N'N'N'N'N'N'N'N'N'N'N'N'N'N'-z"
```

In some preferred embodiment nucleic acid molecules disclosed herein have the following structure

```
5' N N N N N N N N N N N N N N N N N N N-C3Pi-C3OH
3' HOC3-N'N'N'N'N'N'N'N'N'N'N'N'N'N'N'N'N'N'N'-z"
or

5' N N N N N N N N N N N N N N N N N N N-C3Pi-C3OH
3' iPC3-N'N'N'N'N'N'N'N'N'N'N'N'N'N'N'N'N'N'N'-z"
``` wherein of N and N' is independently a ribonucleotide which may be unmodified or modified, or is an unconventional moiety;

wherein each N is linked to the adjacent N by a covalent bond;

wherein each N' is linked to the adjacent N' by a covalent bond; and wherein z" is a capping moiety covalently attached to the 5' terminus of the sense strand.

The term "aB" refers to an abasic moiety which can be riboabasic moiety or a deoxyriboabasic moiety, or an inverted riboabasic moiety or an inverted deoxyriboabasic moiety.

In some embodiments the nucleic acid molecules disclosed herein comprise Z. In other embodiments the nucleic acid molecules disclosed herein comprise Z'. In additional embodiments both Z and Z' are present. In some embodiments Z and Z' are both present and identical. In further embodiments both Z and Z' are present and are different. In some embodiments Z and Z' independently comprise 1 or 2 non-nucleotide moieties. In some embodiments Z and Z' independently comprise 2 non-nucleotide moieties.

In some embodiments Z is present and comprises one or more non-nucleotide moieties selected from an abasic moiety an inverted abasic moiety, an alkyl moiety or derivative thereof, and an inorganic phosphate moiety.

In additional embodiments Z' is present and comprises one or more non-nucleotide moieties selected from an abasic moiety an inverted abasic moiety, an alkyl moiety or derivative thereof or an inorganic phosphate moiety.

In additional embodiments Z and/or Z' are present and independently comprise a combination of one or more nucleotide and one or more non-nucleotide moiety selected from the moieties disclosed herein.

In some embodiments each of Z and Z' includes an abasic moiety, optionally deoxyriboabasic (referred to herein as "dAb") or riboabasic (referred to herein as "rAb") nucleotides. In some embodiments each of Z and/or Z' is dAb-dAb or rAb-rAb.

In some embodiments each of Z and/or Z' independently includes an alkyl moiety, optionally a phosphodiester derivative of propanediol ((CH2)3-Pi, referred to herein also as "C3Pi") modified moiety. In some embodiments Z and/or Z' are C3Pi-C3Pi. In a specific embodiment x=y=19 and Z comprises two propanediol derivatives, C3-C3 (i.e. —C3-Pi-C3-Pi). In various embodiments the C3 moiety is covalently linked to the 3' terminus of the sense or antisense strand via a phosphodiester bond.

In additional embodiments Z and/or Z' comprise a combination of one or more abasic moieties and unmodified nucleotides or a combination of one or more hydrocarbon moieties and unmodified nucleotides or a combination of one or more abasic and hydrocarbon moieties. In such embodiments, Z and/or Z' are optionally C3-rAb or C3-dAb.

In further embodiments relating to structure A1 or A2, the nucleic acid molecules further comprises 2'-OMe sugar modified ribonucleotides at positions 2, 4, 6, 8, 11, 13, 15, 17 and 19 of the antisense strand. In additional embodiments the compound also comprises an L-DNA nucleotide at position 18 of the sense strand. In additional embodiments the compound comprises a nucleotide joined to an adjacent nucleotide by a 2'-5' internucleotide phosphate bond. In additional embodiments x=y=19 and the nucleotides at positions 15-19 or 16-19 or 17-19 in (N')y are joined to adjacent nucleotides by 2'-5' internucleotide phosphate bonds. In some embodiments x=y=19 and the nucleotides at positions 15-19 or 16-19 or 17-19 or 15-18 or 16-18 in (N')y are joined to the adjacent nucleotides by 2'-5' internucleotide phosphate bonds.

According to certain embodiments provided herein are dsRNA compounds, such as siRNA compounds further comprising one or more modified nucleotide, wherein the modified nucleotide possesses a modification in the sugar moiety, in the base moiety or in the internucleotide linkage moiety.

In some embodiments (N)x comprises modified and unmodified ribonucleotides, each modified ribonucleotide a 2'-OMe sugar modified ribonucleotide, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide.

In some embodiments at least one of (N)$_x$ and (N')$_y$ comprises at least one mirror nucleotide. In some embodiments in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond, or any other unconventional moiety disclosed herein.

In some embodiments an unconventional moiety is an L-DNA mirror nucleotide; in additional embodiments at least one unconventional moiety is present at positions 15, 16, 17, or 18 in (N')y. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments the L-DNA moiety is present at position 17, position 18 or positions 17 and 18.

In some embodiments (N)x comprises nine alternating modified ribonucleotides. In other embodiments (N)x comprises nine alternating modified ribonucleotides further comprising a 2' modified nucleotide at position 2. In some embodiments (N)x comprises 2'-OMe modified ribonucleotides at the odd numbered positions 1, 3, 5, 7, 9, 11, 13, 15, 17, 19. In other embodiments (N)x further comprises a 2'-OMe sugar modified ribonucleotide at one or both of positions 2 and 18. In yet other embodiments (N)x comprises 2'-OMe sugar modified ribonucleotides at positions 2, 4, 6, 8, 11, 13, 15, 17, 19. In some embodiments at least one pyrimidine ribonucleotide in (N)x comprises a 2'-OMe sugar modification. In some embodiments all pyrimidine ribonucleotides in (N)x comprises a 2'-OMe sugar modification. In some embodiments 2, 3, 4, 5, 6, 7, 8, 9, 1'0, 11, 12, 13, 14, or 15 pyrimidine ribonucleotides in N(x) comprise a 2'-OMe sugar modification In various embodiments z" is present and is selected from an abasic ribose moiety, a deoxyribose moiety; an inverted abasic ribose moiety, a deoxyribose moiety; C6-amino-Pi; a mirror nucleotide.

In one embodiment of the nucleic acid molecules (N')y comprises at least two nucleotides at either or both the 5' and 3' termini of (N')y are joined by a 2'-5' phosphodiester bond. In certain embodiments x=y=19; in (N)x the nucleotides alternate between modified ribonucleotides and unmodified ribonucleotides, each modified ribonucleotide being a 2'-OMe sugar modified ribonucleotide located at the middle of (N)x being unmodified; and three nucleotides at the 3' terminus of (N')y are joined by two 2'-5' phosphodiester bonds. In other embodiments, x=y=19; in (N)x the nucleotides alternate between modified ribonucleotides and unmodified ribonucleotides, each modified ribonucleotide a 2'-OMe sugar modified ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N)y may be a 2'-OMe sugar modified ribonucleotide. In another embodiment, in (N)x the nucleotides alternate between 2'-OMe sugar modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-Me sugar modifications.

In certain embodiments of Structure (A1), x=y=19 and in (N')y the nucleotide in at least one position comprises a mirror nucleotide, a deoxyribonucleotide and a nucleotide joined to an adjacent nucleotide by a 2'-5' internucleotide bond.

In certain embodiments of Structure (A1), x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. Other embodiments of Structure (A1) are envisaged in wherein x=y=21 or wherein x=y=23; in these embodiments the modifications for (N')y discussed above instead of being on positions 15, 16, 17, 18 are on positions 17, 18, 19, 20 for 21 mer and on positions 19, 20, 21, 22 for 23 mer; similarly the modifications at one or both of positions 17 and 18 are on one or both of positions 19 or 20 for the 21 mer and one or both of positions 21 and 22 for the 23 mer. All modifications in the 19 mer are similarly adjusted for the 21 and 23 mers.

According to various embodiments of Structure A1 or A2 in 2, 3, 4, 5, 6, 7, 8, 9, 10, 11, 12, 13 or 14 consecutive ribonucleotides at the 3' terminus in (N')y or N2-(N')y are linked by 2'-5' internucleotide linkages In one embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'-O-methyl sugar modification. In certain embodiments of Structure (A1), x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16, 17, 18, 16-17, 17-18, or 16-18 in (N')y are joined by a 2'-5' internucleotide bond.

In certain embodiments (N')y comprises an L-DNA at position 2 and 2'-5' internucleotide bonds at positions 16, 17, 18, 16-17, 17-18, or 16-18. In certain embodiments (N')y comprises 2'-5' internucleotide bonds at positions 16, 17, 18, 16-17, 17-18, or 16-18 and a 5' terminal cap nucleotide.

In one embodiment of the nucleic acid molecules, the 3' terminal nucleotide or two or three consecutive nucleotides at the 3' terminus of (N')y are L-deoxyribonucleotides.

In other embodiments the nucleic acid molecules, in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one embodiment, three, four or five consecutive nucleotides at the 5' terminus of (N')y comprise the 2'-OMe modification. In another embodiment, three consecutive nucleotides at the 3' terminus of (N')y comprise the 2'-OMe sugar modification.

In some embodiments of Structure A1 or A2 in (N')y or N2-(N')y or more, consecutive ribonucleotides at either terminus or 2-8 modified nucleotides at each of the 5' and 3' termini are independently bicyclic nucleotide. In various embodiments the bicyclic nucleotide is a locked nucleic acid (LNA). A 2'-O, 4'-C-ethylene-bridged nucleic acid (ENA) is a species of LNA.

In various embodiments (N')y or N2-(N')y comprises modified nucleotides at the 5' terminus or at both the 3' and 5' termini.

In some embodiments of Structure A1 or A2 at least two nucleotides at either or both the 5' and 3' termini of (N')y are joined by P-ethoxy backbone modifications. In certain embodiments x=y=19 or x=y=23; in (N)x the nucleotides alternate between modified ribonucleotides and unmodified ribonucleotides, each modified ribonucleotide being a 2'-OMe sugar modified ribonucleotide and the ribonucleotide located at the middle position of (N)x being unmodified; and four consecutive nucleotides at the 3' terminus or at the 5' terminus of (N')y are joined by three P-ethoxy backbone modifications. In another embodiment, three consecutive nucleotides at the 3' terminus or at the 5' terminus of (N')y are joined by two P-ethoxy backbone modifications.

In some embodiments of Structure A1 or A2 in (N')y or N2-(N')y 2, 3, 4, 5, 6, 7 or 8, consecutive ribonucleotides at each of the 5' and 3' termini are independently mirror nucleotides, nucleotides joined by 2'-5' phosphodiester bond, 2'-OMe sugar modified nucleotides or bicyclic nucleotide. In one embodiment, the modification at the 5' and 3' termini of (N')y is identical. In one embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being a 2'-OMe sugar modified ribonucleotide and the ribonucleotide located at the middle of (N)x being unmodified, or the ribonucleotides in (N)x being unmodified In another embodiment of Structure A1 provided herein are compounds wherein x=y=19; in (N)x the nucleotides alternate between modified ribonucleotides and unmodified ribonucleotides, each modified ribonucleotide being modified to a 2'-OMe sugar modified ribonucleotide and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Pi, C3Pi-C3OH; C3Pi-rAb; C3Pi-dAb; dAb-dAb and rAb-rAb.

In another embodiment five consecutive nucleotides at the 5' terminus of (N')y or N2-(N')y comprise the 2'-O-methyl sugar modification and two consecutive nucleotides at the 3' terminus of (N')y are L-DNA.

According to other embodiments in N')y or N2-(N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some embodiments in N')y or N2-(N')y, 1 or 2 consecutive nucleotides at each of the 5' and 3' termini are PACE nucleotides. Examples of PACE nucleotides and analogs are disclosed in U.S. Pat. Nos. 6,693,187 and 7,067,641 both incorporated by reference.

In one embodiment of Structure (A1), x=y=19; (N)x comprises unmodified ribonucleotides in which two consecutive nucleotides linked by one 2'-5' internucleotide linkage at the 3' terminus; (N')y comprises unmodified ribonucleotides in which two consecutive nucleotides linked by one 2'-5' internucleotide linkage at the 5' terminus; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Ps; C3Pi-C3OH; C3Pi-C3Pi; C3Pi-rAb; C3Pi-dAb; dAb-dAb and rAb-rAb, each C3, rAb, dAb covalently linked to the adjacent C3Pi, rAb, dAb via a phospho-based bond. In some embodiments the phospho-based bond is a phosphodiester bond or a phosphorothiophosphate bond.

In some embodiments, x=y=19; (N)x comprises unmodified ribonucleotides in which three consecutive nucleotides at the 3' terminus are joined together by two 2'-5' phosphodiester bonds; (N')y comprises unmodified ribonucleotides in which four consecutive nucleotides at the 5' terminus are joined together by three 2'-5' phosphodiester bonds; and. Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Ps; C3Pi-C3OH; C3Pi-C3Pi; C3Pi-rAb; C3Pi-dAb; dAb-dAb and rAb-rAb wherein each C3Pi, rAb, dAb covalently linked to the adjacent C3Pi, rAb, dAb via a phospho-based bond. In some embodiments the phospho-based bond is a phosphodiester bond or a phosphorothiophosphate bond.

According to one embodiment of Structure A1 or A2 four consecutive nucleotides at the 5' terminus of (N')y or (N')y-N2, respectively are joined by three 2'-5' phosphodiester bonds; three consecutive nucleotides at the 3' terminus of (N')x are joined by two 2'-5' phosphodiester bonds; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Ps; C3Pi-C3OH; C3Pi-C3Pi; C3Pi-rAb; C3Pi-dAb; C3-dAb; dAb-dAb and rAb-rAb. Three nucleotides at the 5' terminus of (N')y and two nucleotides at the 3' terminus of (N')x may also comprise 3'-O-Me sugar modifications.

In one embodiment of Structure A1 or A2, five consecutive nucleotides at the 5' terminus of (N')y or (N')y-N2, respectively comprise the 2'-O-Me sugar modification and five consecutive nucleotides at the 3' terminus of (N')x comprise the 2'-O-Me sugar modification. In another embodiment ten consecutive nucleotides at the 5' terminus of (N')y comprise the 2'-O-Me sugar modification and five consecutive nucleotides at the 3' terminus of (N')x comprise the 2'-O-Me sugar modification. In another embodiment thirteen consecutive nucleotides at the 5' terminus of (N')y comprise the 2'-O-Me sugar modification; five consecutive nucleotides at the 3' terminus of (N')x comprise the 2'-O-Me sugar modification; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected C3Pi-C3Ps; C3Pi-C3OH; C3Pi-C3Pi; C3Pi-rAb; C3Pi-dAb; dAb-dAb and rAb-rAb.

In specific embodiments five consecutive nucleotides at the 5' terminus of (N')y or (N')y-N2, respectively comprise the 2'-O-Me sugar modification and two consecutive nucleotides at the 3' terminus of (N')y are L-DNA. In addition, the compound may further comprise five consecutive 2'-O-methyl modified nucleotides at the 3' terminus of (N')x and Z and/or Z' may independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide.

In some embodiments Z is selected from C3Pi-C3Ps; C3Pi-C3OH; C3Pi-C3Pi; C3Pi-rAb; C3Pi-dAb; dAb-dAb and rAb-rAb.

In various embodiments of Structure A1 or A2 the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In some embodiments N'(y) comprises 2, 3, 4, 5, 6, 7, or 8 nucleotides joined to an adjacent nucleotide by a 2'-5' internucleotide bond at the 3' terminus. In some embodiments N'(y) comprises 2, 3, 4, 5, 6, 7, or 8 nucleotides joined to an adjacent nucleotide by a 2'-5' internucleotide bond at the 3' penultimate position. In some embodiments x=y=19 and N'(y) comprises 2, 3, 4, or 5 nucleotides joined to an adjacent nucleotide by a 2'-5' internucleotide bond at the 3' terminus. In some embodiments x=y=19 and N'(y) comprises 5 nucleotides joined to an adjacent nucleotide by a 2'-5' internucleotide bond at the 3' terminus i.e. in position 15, 16, 17, 18 and 19 (5'>3'). In some embodiments (N)x comprises 2'-OMe sugar modified ribonucleotides. In some embodiments (N)x comprises 2'-OMe sugar modified pyrimidine ribonucleotides. In some embodiments (N)x comprises 2'-OMe sugar modified ribonucleotides alternating with unmodified ribonucleotides. In some embodiments x=y=19 and (N)x comprises 2'-OMe sugar modified ribonucleotides in position (5'>3') 3, 5 and 11, 13, 15, 17, and 19. In some embodiments (N)x further comprises a mirror nucleotide or a 2'5' nucleotide in positions 6 or 7.

In some embodiments the sequence of (N)x has complementarity to the sequence of (N')y; and the sequence of (N')y has identity to a sequence within an mRNA encoded by a target gene.

In some preferred embodiment nucleic acid molecules disclosed herein have the following structure

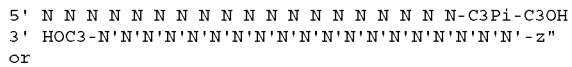

or

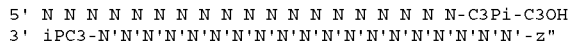

wherein of N and N' is independently a ribonucleotide which may be unmodified or modified, or is an unconventional moiety;

wherein each N is linked to the adjacent N by a covalent bond;

wherein each N' is linked to the adjacent N' by a covalent bond;

wherein 1 to 10 of N are 2'-O Me sugar modified ribonucleotides;

wherein N at position 5, 6, 7, 8 or 9 (5'>3') is a 2'5 nucleotide or a mirror nucleotide;

wherein N' at positions 15-19 (5'>3') are 2'5' ribonucleotides;

wherein z" is a capping moiety covalently attached to the 5' terminus of the sense strand.

In some preferred embodiment nucleic acid molecules disclosed herein have the following structure

```
5' N N N N N N N N N N N N N N N N N N N-C3Pi-C3OH
3' HOC3-N'N'N'N'N'N'N'N'N'N'N'N'N'N'N'N'N'N'N'-z"
or

5' N N N N N N N N N N N N N N N N N N N-C3Pi-C3OH
3'iPC3-N'N'N'N'N'N'N'N'N'N'N'N'N'N'N'N'N'N'N'-z"
``` wherein of N and N' is independently a ribonucleotide which may be unmodified or modified, or is an unconventional moiety;

wherein each N is linked to the adjacent N by a covalent bond;

wherein each N' is linked to the adjacent N' by a covalent bond;

wherein 1 to 10 of N are 2'-O Me sugar modified ribonucleotides;

wherein N at position 5, 6, 7, 8 or 9 (5'>3') is a 2'5 nucleotide or a mirror nucleotide;

wherein N' comprises one or more 2'-O Me sugar modified pyrimidine ribonucleotides;

wherein N at position 9 or 10 (5'>3') is a 2'5nucleotide; and wherein z" is a capping moiety covalently attached to the 5' terminus of the sense strand.

In some embodiments of Structures (A1-A2), either the sense strand or the antisense strand or both the sense strand and the antisense strand comprise an inorganic phosphate moieties at the 3' termini.

In some embodiments of the double stranded nucleic acid molecules, N at the 3' terminus is a modified ribonucleotide and (N)x comprises at least 8 modified ribonucleotides. In some embodiments the modified ribonucleotides comprise 2'-OMe sugar modified ribonucleotides. In other embodiments at least 5 of the at least 8 modified ribonucleotides are alternating beginning at the 3' end.

In some embodiments of the double stranded nucleic acid molecules z" is present and is selected from an abasic ribose moiety, a deoxyribose moiety; an inverted abasic ribose moiety, a deoxyribose moiety; C6-amino-Pi; a mirror nucleotide.

In some embodiments of the double stranded nucleic acid molecules in (N')y at least one additional unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond. In some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 2' termini position using cleavable or non-cleavable phosphate groups.

In certain embodiments for all of the above-mentioned structures, Z is present. In other embodiments Z' is present. In additional embodiments both Z and Z' are present. In some embodiments Z and Z' are both present and identical. In further embodiments both Z and Z' are present and are different. In some embodiments Z and Z' are independently 1, 2, 3, 4 or 5 non-nucleotide moieties, or a combination of a non-nucleotide moiety and a nucleotide.

In some embodiments Z is present and comprises one or more non-nucleotide moiety selected from an abasic moiety, an inverted abasic moiety, a hydrocarbon moiety such as (CH$_2$)3, and an inorganic phosphate moiety.

In additional embodiments Z' is present and comprises one or more non-nucleotide moiety selected from an abasic moiety, an inverted abasic moiety, a hydrocarbon moiety such as (CH$_2$)3, and an inorganic phosphate moiety.

In some embodiments each of Z and/or Z' comprises one or two non-nucleotide moieties and further comprises a nucleotide.

In some embodiments Z and/or Z' comprise abasic moieties, optionally deoxyribo-abasic (referred to herein as "dAb") or riboabasic (referred to herein as "rAb") moieties. In some embodiments each of Z and/or Z' is dAb-dAb or rAb-rAb.

In some embodiments Z and/or Z' comprise one or more hydrocarbon moieties, optionally (CH$_2$)3-Pi (referred to herein as "C3Pi"). In some embodiments Z and/or Z' is C3Pi-C3Ps; C3Pi-C3OH; or C3Pi-C3Pi.

In additional embodiments Z and/or Z' comprise a combination of abasic moieties and unmodified nucleotides or a combination of hydrocarbon modified moieties and unmodified nucleotides or a combination of abasic moieties and hydrocarbon modified moieties. In such embodiments, Z and/or Z' are optionally C3Pi-rAb. In a particular embodiment only Z is present and is C3Pi-C3Ps; C3Pi-C3OH; C3Pi-C3Pi.

In the embodiments of the above-mentioned Structures, the compound comprises at least one 3' overhang (Z and or Z') comprising at least one non-nucleotide moiety. Z and Z' independently comprises one non-nucleotide moiety and one or more covalently linked modified or non-modified nucleotides or unconventional moiety, for example inverted dT or dA; dT, LNA, mirror nucleotide and the like. The siRNA in which Z and/or Z' is present has improved activity and/or stability and/or off-target activity and or reduced immune response when compared to an siRNA in which Z and/or Z' are absent or in which Z and/or Z' is dTdT.

In certain embodiments for all the above-mentioned Structures, the compound comprises one or more phosphonocarboxylate and/or phosphinocarboxylate nucleotides (PACE nucleotides). In some embodiments the PACE nucleotides are deoxyribonucleotides and the phosphinocarboxylate nucleotides are phosphinoacetate nucleotides. Examples of PACE nucleotides and analogs are disclosed in U.S. Pat. Nos. 6,693,187 and 7,067,641, both incorporated herein by reference.

In certain embodiments for all the above-mentioned Structures, the compound comprises one or more locked nucleic acids (LNA) also defined as bridged nucleic acids or bicyclic nucleotides. Exemplary locked nucleic acids include 2'-O, 4'-C-ethylene nucleosides (ENA) or 2'-O, 4'-C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allart, et al., 1998. Nucleosides & Nucleotides 17:1523-1526; Herdewijn et al., 1999. Nucleosides & Nucleotides 18:1371-1376; Fisher et al., 2007, NAR 35(4):1064-1074; all incorporated herein by reference).

The present invention explicitly excludes double stranded compounds in which each of N and/or N' is a deoxyribonucleotide (dA, dC, dG, dT). In certain embodiments (N)x and (N')y may comprise independently 1, 2, 3, 4, 5, 6, 7, 8, 9 or 10 deoxyribonucleotides. In certain embodiments provided herein a compound wherein each of N is an unmodified ribonucleotide and the 3' terminal nucleotide or 2, 3, 4, 5, 6, 7, 8, 9, or 10, consecutive nucleotides at the 3' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide. In some embodiments the 5' terminal nucleotide of N or 2 or 3 consecutive of N and 1, 2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain embodiments a covalent bond is a phosphodiester bond. Covalent bond encompasses non-phosphorous-containing internucleoside linkages, such as those disclosed in WO 2004/041924 inter alia. Unless otherwise indicated, in embodiments of the structures discussed herein the covalent bond between each consecutive N or N' is a phosphodiester bond.

In some embodiments the oligonucleotide sequence of (N)x is fully complementary to the oligonucleotide sequence of (N')y. In other embodiments (N)x and (N')y are substantially complementary. In certain embodiments (N)x is fully complementary to a consecutive sequence in a target mRNA. In other embodiments (N)x is substantially complementary to consecutive sequence in a target mRNA.

Definitions

For convenience certain terms employed in the specification, examples and claims are described herein.

It is to be noted that, as used herein, the singular forms "a", "an" and "the" include plural forms unless the content clearly dictates otherwise.

An "inhibitor" is a compound, which is capable of reducing (partially or fully) the expression of a gene or the activity of the product of such gene to an extent sufficient to achieve a desired biological or physiological effect. The term "inhibitor" as used herein refers to a double stranded nucleic acid inhibitor.

A "dsRNA inhibitor" or dsNA inhibitor refers to a double stranded nucleic acid compound or molecule which is capable of reducing the expression of a gene or the activity of the product of such gene to an extent sufficient to achieve a desired biological or physiological effect. The term "siRNA inhibitor" as used herein refers to one or more of a siRNA, shRNA, synthetic shRNA; miRNA. As used herein, the term "inhibit", "down-regulate", or "reduce" with respect to gene expression means that the expression of a target gene, or level of RNA molecules or equivalent RNA molecules encoding one or more proteins or protein subunits (e.g., mRNA), or activity of one or more proteins or protein subunits, is reduced below that observed in the absence of an inhibitor (such as a nucleic acid molecule, e.g., a dsNA, for example having structural features as described herein); for example the expression may be reduced to 90%, 80%, 70%, 60%, 50%, 40%, 30%, 20%, 10%, 5% or less than that observed in the absence of an inhibitor.

As used herein, the term "inhibition" of a target gene means inhibition of the gene expression (transcription or translation) or polypeptide activity of a target gene wherein the target gene is mammalian gene selected from the group consisting of TLR2, TLR4, MYD88, TICAM1 and TIRAP, or variants thereof. The polynucleotide sequence of the target mRNA sequence, or the target gene having a mRNA sequence refer to the mRNA sequence or any homologous sequences thereof preferably having at least 70% identity, more preferably 80% identity, even more preferably 90% or 95% identity to the mRNA of TLR2, TLR4, MYD88, TICAM1 and TIRAP. Therefore, polynucleotide sequences derived from the mammalian gene selected from the group consisting of TLR2, TLR4, MYD88, TICAM1 and TIRAP RNA and mRNA which have undergone mutations, alterations or modifications as described herein are encompassed in the present invention. The terms "mRNA polynucleotide sequence", "mRNA sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application mRNA sequences are set forth as representing the target of their corresponding genes. The terms "mRNA polynucleotide sequence" and mRNA are used interchangeably.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and/or the linkages between nucleotides in the oligonucleotide. An oligonucleotide disclosed herein encompass molecules comprising deoxyribonucleotides, ribonucleotides, modified deoxyribonucleotides, modified ribonucleotides and combinations thereof. As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

Provided herein are methods and compositions for inhibiting expression of a target gene in vivo. In general, the method includes administering oligoribonucleotides, such as double stranded RNAs, in particular small interfering RNAs (i.e., siRNAs) or a nucleic acid material that generates siRNA in a cell, to target a mammalian mRNA in an amount sufficient to down-regulate expression of a target gene by an RNA interference mechanism. In particular, the method is useful for inhibiting expression of the gene for treatment of a subject suffering from a disease related to expression of that gene. As disclosed herein the dsRNA molecules or inhibitors of the target gene are used as drugs to treat various pathologies.

"siRNA compound" and "nucleic acid molecule" may be used interchangeably herein.

"Nucleotide" is meant to encompass a compound consisting of a nucleoside (a sugar, usually ribose or deoxyribose, and a purine or pyrimidine base) and a phospho linker; such as a deoxyribonucleotide and a ribonucleotide, which may be natural or synthetic, and be modified or unmodified. Modifications include changes and substitutions to the sugar moiety, the base moiety and/or the internucleotide linkages.

A "phosphate based" moiety includes inorganic phosphate (Pi) and phosphorothioate (Ps).

All analogs of, or modifications to, a nucleotide/oligonucleotide may be employed with the molecules disclosed herein, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

What is sometimes referred to as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide. Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate. In general, an inverted abasic moiety is covalently attached to a 3' terminal nucleotide via a 3'-3' linkage; an inverted abasic moiety is covalently attached to a 5' terminal nucleotide via a 5'-5' linkage; an inverted abasic moiety is generally covalently attached to an inverted abasic moiety via a 5'-3' linkage.

The term "capping moiety" (z") as used herein includes a moiety which can be covalently linked to the 5' terminus of (N')y and includes abasic ribose moiety, abasic deoxyribose moiety, modified abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain capping moieties are abasic ribose or abasic deoxyribose moieties; inverted abasic ribose or inverted abasic deoxyribose moieties; C6-amino-Pi; a mirror nucleotide including L-DNA and L-RNA. The compounds disclosed herein may be synthesized using one or more inverted nucleotides, for example inverted thymidine or inverted adenine (for example see Takei, et al., 2002. JBC 277(26): 23800-06.

Chemical modifications also include unlocked nucleic acids, or UNAs, which are non-nucleotide, acyclic analogues, in which the C2'-C3' bond is not present (although UNAs are not truly nucleotides, they are expressly included in the scope of "modified" nucleotides or modified nucleic acids as contemplated herein). In particular embodiments, nucleic acid molecules with an overhang may be modified to have UNAs at the overhang positions (i.e., 2 nucleotide overhand). In other embodiments, UNAs are included at the 3'- or 5'-ends. A UNA may be located anywhere along a nucleic acid strand, i.e. at position 5, 6, 7, 8, or 9. Nucleic acid molecules may contain one or more than UNA. Exemplary UNAs are disclosed in Nucleic Acids Symposium Series No. 52 p. 133-134 (2008).

The term "non-nucleotide moiety" refers to a moiety that is not a nucleotide, i.e. does not include all of the components of a nucleotide: a sugar. a base and a linker.

The term "unconventional moiety" as used herein refers to the non-nucleotide moieties including an abasic moiety, an inverted abasic moiety, an alkyl moiety or alcohol, and an inorganic phosphate and further includes a deoxyribonucleotide, a modified deoxyribonucleotide, a mirror nucleotide (L-DNA or L-RNA), a non-base pairing nucleotide analog and a nucleotide joined to an adjacent nucleotide by a 2'-5' internucleotide phosphate bond (also known as 2'5' nucleotide); bridged nucleic acids including LNA and ethylene bridged nucleic acids, linkage modified (e.g. PACE) and base modified nucleotides as well as additional moieties explicitly disclosed herein as unconventional moieties.

When used in reference to the overhangs, an "alkyl moiety" or a "hydrocarbon moiety" refers to a C2, C3, C4, C5 or C6 straight chain or branched alkyl moiety, including for example C2 (ethyl), C3 (propyl). When used in reference to the overhangs, a "derivative" of an alkyl or a hydrocarbon moiety refers to a C2, C3, C4, C5 or C6 straight chain or branched alkyl moiety comprising a functional group which may be selected from among, inter alia, alcohols, phosphodiester, phosphorothioate, phosphonoacetate, amines, carboxylic acids, esters, amides and aldehydes.

When used in reference to modification of the ribose or deoxyribose moiety, "alkyl" is intended to include linear, branched, or cyclic saturated hydrocarbon structures and combinations thereof "Lower alkyl", when used in reference to modification of the ribose or deoxyribose moiety, refers specifically to alkyl groups of from 1 to 6 carbon atoms. Examples of lower alkyl groups include methyl, ethyl, propyl, isopropyl, butyl, s- and t-butyl and the like. Preferred alkyl groups are those of C20 or below. Cycloalkyl is a subset of alkyl and includes cyclic saturated hydrocarbon groups of from 3 to 8 carbon atoms. Examples of cycloalkyl groups include c-propyl, c-butyl, c-pentyl, norbornyl, adamantyl and the like "Terminal functional group" includes halogen, alcohol, amine, carboxylic, ester, amide, aldehyde, ketone, ether groups.

As used herein, a "mirror" nucleotide (also referred to as a spiegelmer) is a nucleotide analog with reverse chirality to the naturally occurring or commonly employed nucleotide, i.e., a mirror image of the naturally occurring or commonly employed nucleotide. The mirror nucleotide is a ribonucleotide (L-RNA) or a deoxyribonucleotide (L-DNA) and may further comprise at least one sugar or base modification and/or a backbone modification, such as a phosphorothioate or phosphonate moiety. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine- 3'-phosphate (mirror rA); L-ribocytidine-3'-phosphate (mirror rC); L-riboguanosine-3'-phosphate (mirror rG); L-ribouracil-3'-phosphate (mirror dU).

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Unconventional moieties include bridged nucleic acids including LNA (2'-O,4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

In some embodiments the unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

The nucleotides are selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. dsRNA compounds comprising one or more abasic pseudonucleotides are encompassed herein. A nucleotide monomer comprising a modified base, including abasic pseudonucleotide monomers, may be substituted for one or more ribonucleotides of the oligonucleotide. An abasic pseudonucleotide monomer may be included at the one or more of the terminal positions or as a 5' terminal cap. A 5' terminal cap may also be selected from an inverted abasic pseudonucleotide analog, an L-DNA nucleotide, and a C6-imine phosphate.

In addition, analogues of polynucleotides are prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA) comprises a polyamide backbone which is similar to that found in peptides. PNA analogs have been shown to be resistant to enzymatic degradation and to have extended lives in vivo and in vitro.

Possible modifications to the sugar residue are manifold and include 2'-O alkyl, 2'-halo (e.g. 2' deoxy fluoro), locked nucleic acid (LNA), glycol nucleic acid (GNA), threose nucleic acid (TNA), arabinoside; altritol (ANA) and other 6-membered sugars including morpholinos, and cyclohexinyls. Possible modifications on the 2' moiety of the sugar residue include amino, fluoro, methoxy alkoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1. One or more deoxyribonucleotides are also tolerated in the compounds disclosed herein. In some embodiments (N') comprises 1, 2, 3, 4, 5, 6, 7, 8, 9 or 10 DNA moieties.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1):439-447) and in International Patent Publication No. WO 2004/083430. Six-membered ring nucleotide analogs are disclosed in Allart, et al (Nucleosides & Nucleotides, 1998, 17:1523-1526, and Perez-Perez, et al., 1996, Bioorg. and Medicinal Chem Letters 6:1457-1460) Oligonucleotides comprising 6-membered ring nucleotide analogs including hexitol and altritol nucleotide monomers are disclosed in International patent application publication No. WO 2006/047842.

Backbone modifications, also known as internucleotide linkage modifications, such as ethyl (resulting in a phosphoethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetate derivatives. Certain structures include dsRNA compounds having one or a plurality of 2'-5' internucleotide linkages (bridges or backbone).

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules disclosed herein may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

As used herein, a gap in a nucleic acid refers to the absence of one or more internal nucleotides in one strand, while a nick in a nucleic acid refers to the absence of an internucleotide linkage between two adjacent nucleotides in one strand. Any of the molecules disclosed herein may contain one or more gaps and/or one or more nicks.

Nucleic acid molecules include those with blunt ends, i.e., ends that do not include any overhanging nucleotides. A nucleic acid molecule can include one or more blunt ends. The blunt ended nucleic acid molecule has a number of base pairs equal to the number of nucleotides present in each strand of the nucleic acid molecule. The nucleic acid molecule can include one blunt end, for example where the 5'-end of the antisense strand and the 3'-end of the sense strand do not have any overhanging nucleotides. Nucleic acid molecule may include one blunt end, for example where the 3'-end of the antisense strand and the 5'-end of the sense strand do not have any overhanging nucleotides. A nucleic acid molecule may include two blunt ends, for example where the 3'-end of the antisense strand and the 5'-end of the sense strand as well as the 5'-end of the antisense strand and 3'-end of the sense strand do not have any overhanging nucleotides. Other nucleotides present in a blunt ended nucleic acid molecule can include, for example, mismatches, bulges, loops, or wobble base pairs to modulate the activity of the nucleic acid molecule, e.g. to mediate RNA interference.

In certain embodiments of the nucleic acid molecules (e.g., dsNA molecules) provided herein, at least one end of the molecule has an overhang of at least one nucleotide (for example 1 to 8 nucleotides covalently attached to a terminus of the oligonucleotide). For example, one or both strands of a double stranded nucleic acid molecule disclosed herein may have an overhang at the 5'-end or at the 3'-end or both. An overhang may be present at either or both the sense strand and antisense strand of the nucleic acid molecule. The length of the overhang may be as little as one nucleotide and as long as 1 to 8 or more nucleotides (e.g., 1, 2, 3, 4, 5, 6, 7 or 8 nucleotides; in some preferred embodiments an overhang is 2, 3, 4, 5, 6, 7 or 8 nucleotides; for example an overhang may be 2 nucleotides. The nucleotide(s) forming the overhang may be include deoxyribonucleotide(s), ribonucleotide(s), natural and non-natural nucleobases or any nucleotide modified in the sugar, base or phosphate group, such as disclosed herein. A double stranded nucleic acid molecule may have both 5'- and 3'-overhangs. The overhangs at the 5'- and 3'-end may be of different lengths. A overhang may include at least one nucleic acid modification which may be deoxyribonucleotide. One or more deoxyribonucleotides may be at the 5'-terminus. The 3'-end of the respective counter-strand of the nucleic acid molecule may not have an overhang, more preferably not a deoxyribonucleotide overhang. The one or more deoxyribonucleotide may be at the 3'-terminus. The 5'-end of the respective counter-strand of the dsRNA may not have an overhang, more preferably not a deoxyribonucleotide overhang. The overhang in either the 5'- or the 3'-end of a strand may be 1 to 8 (e.g., about 1, 2, 3, 4, 5, 6, 7 or 8) unpaired nucleotides, preferably, the overhang is 2-3 unpaired nucleotides; more preferably 2 unpaired nucleotides. Nucleic acid molecules may include duplex nucleic acid molecules with overhanging ends of about 1 to about 20 (e.g., about 1, 2, 3, 4, 5, 6, 7, 8, 9, 10, 11, 12, 13, 1, 15, 16, 17, 18, 19 or 20); preferably 1-8 (e.g., about 1, 2, 3, 4, 5, 6, 7 or 8) nucleotides, for example, about 21-nucleotide duplexes with about 19 base pairs and 3'-terminal mononucleotide, dinucleotide, or trinucleotide overhangs. Nucleic acid molecules provided herein may include duplex nucleic acid molecules with blunt ends, where both ends are blunt, or alternatively, where one of the ends is blunt. Nucleic acid molecules disclosed herein can include one or more blunt ends, i.e. where a blunt end does not have any overhanging nucleotides. In one embodiment, the blunt ended nucleic acid molecule has a number of base pairs equal to the number of nucleotides present in each strand of the nucleic acid molecule. The nucleic acid molecule may include one blunt end, for example where the 5'-end of the antisense strand and the 3'-end of the sense strand do not have any overhanging nucleotides. The nucleic acid molecule may include one blunt end, for example where the 3'-end of the antisense strand and the 5'-end of the sense strand do not have any overhanging nucleotides. A nucleic acid molecule may include two blunt ends, for example where the 3'-end of the antisense strand and the 5'-end of the sense strand as well as the 5'-end of the antisense strand and 3'-end of the sense strand do not have any overhanging nucleotides. In certain preferred embodiments the nucleic acid compounds are blunt ended. Other nucleotides present in a blunt ended dsNA molecule can include, for example, mismatches, bulges, loops, or wobble base pairs to modulate the activity of the nucleic acid molecule to mediate RNA interference.

In many embodiments one or more, or all, of the overhang nucleotides of a nucleic acid molecule (e.g., a dsNA molecule) as described herein includes are modified such as described herein; for example one or more, or all, of the nucleotides may be 2'-deoxynucleotides.

Amount, Location and Patterns of Modifications of Nucleic Acid Compounds

[Nucleic acid molecules (e.g., dsNA molecules) disclosed herein may include modified nucleotides as a percentage of the total number of nucleotides present in the nucleic acid molecule. As such, a nucleic acid molecule may include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given nucleic acid molecule will depend on the total number of nucleotides present in the nucleic acid. If the nucleic acid molecule is single stranded, the percent modification can be based upon the total number of nucleotides present in the single stranded nucleic acid molecule. Likewise, if the nucleic acid molecule is double stranded, the percent modification can be based upon the total number of nucleotides present in the sense strand, antisense strand, or both the sense and antisense strands.

[Nucleic acid molecules disclosed herein may include unmodified RNA as a percentage of the total nucleotides in the nucleic acid molecule. As such, a nucleic acid molecule may include about 5% to about 100% unmodified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% of total nucleotides present in a nucleic acid molecule).

A nucleic acid molecule (e.g., an dsNA molecule) may include a sense strand that includes about 1 to about 5, specifically about 1, 2, 3, 4, or 5 phosphorothioate internucleotide linkages, and/or one or more (e.g., about 1, 2, 3, 4, 5, or more) 2'-deoxy, 2'-O-methyl, 2'-deoxy-2'-fluoro, and/or one or more (e.g., about 1, 2, 3, 4, 5, or more) universal base modified nucleotides, and optionally a terminal cap molecule at the 3-end, the 5'-end, or both of the 3'- and 5'-ends of the sense strand; and wherein the antisense strand includes about 1 to about 5 or more, specifically about 1, 2, 3, 4, 5, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. A nucleic acid molecule may include about 1, 2, 3, 4, 5, 6, 7, 8, 9, 10, or more, pyrimidine nucleotides of the sense and/or antisense nucleic acid strand are chemically-modified with 2'-deoxy, 2'-O-methyl and/or 2'-deoxy-2'-fluoro nucleotides, with or without about 1 to about 5 or more, for example about 1, 2, 3, 4, 5, or more phosphorothioate internucleotide linkages and/or a terminal cap molecule at the 3'-end, the 5'-end, or both of the 3'- and 5'-ends, being present in the same or different strand.

A nucleic acid molecule may include about 1 to about 5 or more (specifically about 1, 2, 3, 4, 5 or more) phosphorothioate internucleotide linkages in each strand of the nucleic acid molecule.

A nucleic acid molecule may include 2'-5' internucleotide linkages, for example at the 3'-end, the 5'-end, or both of the 3'-end and 5'-end of one or both nucleic acid sequence strands. In addition, the 2'-5' internucleotide linkage(s) can be present at various other positions within one or both nucleic acid sequence strands, for example, about 1, 2, 3, 4, 5, 6, 7, 8, 9, 10, or more including every internucleotide linkage of a pyrimidine nucleotide in one or both strands of the siNA molecule can include a 2'-5' internucleotide linkage, or about 1, 2, 3, 4, 5, 6, 7, 8, 9, 10, or more including every internucleotide linkage of a purine nucleotide in one or both strands of the siNA molecule can include a 2'-5' internucleotide linkage.

A chemically-modified short interfering nucleic acid (dsNA) molecule may include an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides).

A chemically-modified short interfering nucleic acid (dsNA) molecule may include an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

A chemically-modified short interfering nucleic acid (dsNA) molecule capable of mediating RNA interference (RNAi) against TLR2 and/or TLR4 inside a cell or reconstituted in vitro system may include a sense region, wherein one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), and an antisense region, wherein one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). The sense region and/or the antisense region can have a terminal cap modification, such as any modification, that is optionally present at the 3'-end, the 5'-end, or both of the 3'-end and the 5'-end of the sense and/or antisense sequence. The sense and/or antisense region can optionally further include a 3'-terminal nucleotide overhang having about 1 to about 4 (e.g., about 1, 2, 3, or 4) 2'-deoxyribonucleotides. The overhang nucleotides can further include one or more (e.g., about 1, 2, 3, 4 or more) phosphorothioate, phosphonoacetate, and/or thiophosphonoacetate internucleotide linkages. The purine nucleotides in the sense region may alternatively be 2'-O-methyl purine nucleotides (e.g., wherein all purine nucleotides are 2'-O-methyl purine nucleotides or alternately a plurality of purine nucleotides are 2'-O-methyl purine nucleotides) and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). One or more purine nucleotides in the sense region may alternatively be purine ribonucleotides (e.g., wherein all purine nucleotides are purine ribonucleotides or alternately a plurality of purine nucleotides are purine ribonucleotides) and any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). One or more purine nucleotides in the sense region and/or present in the antisense region may alternatively be selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides).

Double Stranded Oligonucleotides

The selection and synthesis of dsRNAs, such as siRNA corresponding to known genes has been widely reported; see for example Ui-Tei et al., J Biomed Biotechnol. 2006; 65052; Chalk et al., BBRC. 2004, 319(1):264-74; Sioud & Leirdal, Met. Mol Biol. 2004, 252:457-69; Levenkova et al., Bioinform. 2004, 20(3):430-2; Ui-Tei et al., NAR. 2004, 32(3):936-48. For examples of the use and production of modified dsRNA see for example Braasch et al., Biochem. 2003, 42(26):7967-75; Chiu et al., RNA. 2003, 9(9):1034-48; PCT Publication Nos. WO 2004/015107 and WO 02/44321 and U.S. Pat. Nos. 5,898,031 and 6,107,094.

Provided herein are double-stranded oligonucleotides (e.g. dsRNAs, including siRNAs), which down-regulate the expression of a desired gene. The dsRNA disclosed herein are duplex oligoribonucleotides in which the sense strand is derived from the mRNA sequence of the desired gene, and the antisense strand is at least substantially complementary to the sense strand. In general, some deviation from the target mRNA sequence is tolerated without compromising the siRNA activity (see e.g. Czauderna et al., NAR. 2003, 31(11):2705-2716). The dsRNA disclosed herein inhibit gene expression on a post-transcriptional level with or without destroying the mRNA. Without being bound by theory, dsRNA may be siRNA which targets the mRNA for specific cleavage and degradation and/or may inhibit translation from the targeted message.

In other embodiments at least one of the two strands may have an overhang of at least one nucleotide at the 5'-terminus; the overhang may consist of at least one deoxyribonucleotide. The length of RNA duplex is from about 16 to about 40 ribonucleotides, preferably 19 ribonucleotides.

Further, the length of each strand may independently have a length selected from the group consisting of about 16 to about 40 bases, preferably 18 to 23 bases and more preferably 19 ribonucleotides.

In certain embodiments the complementarity between said first strand and the target nucleic acid is perfect. In some embodiments, the strands are substantially complementary, i.e. having one, two or up to five mismatches between said first strand and the target mRNA or between the first and the second strands. Substantially complementary refers to complementarity of greater than about 70%, and less than 100% to another sequence. For example in a duplex region consisting of 19 base pairs one mismatch results in 94.7% complementarity, two mismatches results in about 89.5% complementarity, 3 mismatches results in about 84.2% complementarity, 4 mismatches results in about 79% complementarity and 5 mismatches results in about 74% complementarity, rendering the duplex region substantially complementary. Accordingly, substantially identical refers to identity of greater than about 70%, to another sequence.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the dsRNA may be linked to the 3'-terminus of the second strand, or the 3'-terminus of the first strand may be linked to the 5'-terminus of the second strand, said linkage being via a nucleic acid linker typically having a length between 2-100 nucleobases, preferably about 2 to about 30 nucleobases.

In some embodiments, the compounds include alternating ribonucleotides modified in at least one of the antisense and the sense strands of the compound, for 19 mer and 23 mer oligomers the ribonucleotides at the 5' and 3' termini of the antisense strand are modified in their sugar residues, and the ribonucleotides at the 5' and 3' termini of the sense strand are unmodified in their sugar residues. For 21 mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, in some embodiments the middle nucleotide of the antisense strand is unmodified.

According to one embodiment, the antisense and the sense strands of the oligonucleotide/siRNA are phosphorylated only at the 3'-terminus and not at the 5'-terminus. According to another embodiment, the antisense and the sense strands are non-phosphorylated. According to yet another embodiment, the 5' most ribonucleotide in the sense strand is modified to abolish any possibility of in vivo 5'-phosphorylation.

The dsRNA sequences disclosed herein are prepared having any of the modifications/structures disclosed herein. The combination of sequence plus structure is novel and is useful used in the treatment of the conditions disclosed herein.

"Target" or "Target gene" refers to the TLR2, TLR4, MYD88, TICAM1 and TIRAP RNA and mRNA polynucleotide sequences set forth in SEQ ID NO: 1-12, or any homologous sequence thereof preferably having at least 70% identity, more preferable 80% identity, even more preferably 90% or 95% identity. This encompasses any sequences derived from SEQ ID NO: 1-12 which have undergone mutations, alterations, polymorphisms or modifications as described herein.

Provided herein are novel unmodified and chemically modified oligonucleotides and oligoribonucleotide compounds that possess therapeutic properties. In particular, provided herein are chemically modified dsRNA compounds. The dsRNAs disclosed herein possess novel structures and novel modifications which have one or more of the following advantages: increased activity or reduced toxicity or reduced off-target effect or reduced immune response or increased stability; the novel modifications of the dsRNAs are beneficially applied to double stranded RNA useful in down regulating, inhibiting or attenuating TLR2, TLR4, MYD88, TICAM1 and TIRAP gene expression and to the use of the novel siRNAs in the treatment of various medical conditions. Particular conditions to be treated include, without being limited to, preventing, treating and attenuating posttransplantational complication in organ transplant, for example lung transplant patients, such as for example primary graft failure, ischemia-reperfusion injury, reperfusion injury, reperfusion edema, allograft dysfunction, pulmonary reimplantation response and/or primary graft dysfunction (PGD).

The compounds disclosed herein possess structures and modifications which impart one or more of increased activity, increased stability, reduced toxicity, reduced off target effect, and/or reduced immune response. The double stranded structures disclosed herein are beneficially applied to double stranded RNA useful in preventing or attenuating expression of TLR2, TLR4, MYD88, TICAM1 and TIRAP gene.

Also disclosed herein is the use of the chemically modified dsRNAs in preventing, treating and/or attenuating posttransplantational complication in organ transplant, such as lung transplant, patients, such as for example primary graft failure, ischemia-reperfusion injury, reperfusion injury, reperfusion edema, allograft dysfunction, pulmonary reimplantation response and/or primary graft dysfunction (PGD). Sense and antisense oligonucleotides useful in the synthesis of dsRNA as disclosed herein are provided in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP).

SEQ ID NOS:13-3060 provide oligonucleotides useful in generating dsRNA compounds according to Structure (A1) to target TLR2; SEQ ID NOS:3061-5846 provide oligonucleotides useful in generating dsRNA compounds according to Structure (A2) to target TLR2. Certain preferred oligonucleotide pairs useful in generating double stranded nucleic acid molecules for down-regulating expression of TLR2 are set forth in Table 1, hereinbelow.

SEQ ID NOS:5847-8612 provide oligonucleotides useful in generating dsRNA compounds according to Structure (A1) to target TLR4; SEQ ID NOS:8613-12144 provide oligonucleotides useful in generating dsRNA compounds according to Structure (A2) to target TLR4.

SEQ ID NOS:12145-13924 provide oligonucleotides useful in generating dsRNA compounds according to Structure (A1) to target MYD88; SEQ ID NOS:13925-16332 provide oligonucleotides useful in generating dsRNA compounds according to Structure (A2) to target MYD88. A preferred oligonucleotide pair useful in generating double stranded nucleic acid molecule for down-regulating expression of MYD88 is set forth in Table 3, hereinbelow.

SEQ ID NOS:16333-16882 provide oligonucleotides useful in generating dsRNA compounds according to Structure (A1) to target TICAM1; SEQ ID NOS:16333-18242 provide oligonucleotides useful in generating dsRNA compounds according to Structure (A2) to target TICAM1. Certain preferred oligonucleotide pairs useful in generating double stranded nucleic acid molecules for down-regulating expression of TICAM1 are set forth in Table 4, hereinbelow.

SEQ ID NOS:18243-19010 provide oligonucleotides useful in generating dsRNA compounds according to Structure (A1) to target TIRAP; SEQ ID NOS:19011-20606 provide oligonucleotides useful in generating dsRNA compounds according to Structure (A2) to target TIRAP. Certain preferred oligonucleotide pairs useful in generating double stranded nucleic acid molecules for down-regulating expression of TIRAP are set forth in Table 5, hereinbelow.

Additional 21- or 23-mer dsRNA sequences are generated by 5' and/or 3' extension of the 19-mer oligonucleotide sequences disclosed herein. Such extension is preferably complementary to the corresponding mRNA sequence.

Methods, molecules and compositions disclosed herein which inhibit the TLR2, TLR4, MYD88, TICAM1 and TIRAP gene are discussed herein at length, and any of said molecules and/or compositions are beneficially employed in the treatment of a subject suffering from one or more of said conditions.

Throughout the specification, nucleotide positions are numbered from 1 to 19 and are counted from the 5' end of the antisense strand or the sense strand. For example, position 1 on (N)x refers to the 5' terminal nucleotide on the antisense oligonucleotide strand and position 1 on (N')y refers to the 5' terminal nucleotide on the sense oligonucleotide strand. In the double stranded nucleic acid molecules according to Structure A2, N1 represents position 1 (5' terminal nucleotide) in the antisense strand and N2 represents the 3' terminal nucleotide in the sense strand.

An additional molecule disclosed herein is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule disclosed herein is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar. Such structures are disclosed in PCT patent publication WO 2007/091269, assigned to the assignee of the present invention and incorporated herein in its entirety by reference.

Said triple-stranded oligonucleotide may be an oligoribonucleotide having the general structure:

```
5' Oligo1 (sense) LINKER A Oligo2 (sense) 3'
3' Oligo1 (antisense) LINKER B Oligo3 (sense) 5'
3' Oligo3 (antisense) LINKER C Oligo2 (antisense) 5'
Or
5' Oligo1 (sense) LINKER A Oligo2 (antisense) 3'
3' Oligo1 (antisense) LINKER B Oligo3 (sense) 5'
3' Oligo3 (antisense) LINKER C Oligo2 (sense) 5'
or
5' Oligo1 (sense) LINKER A Oligo3 (antisense) 3'
3' Oligo1 (antisense) LINKER B Oligo2 (sense) 5'
5' Oligo3 (sense) LINKER C Oligo2 (antisense) 3'
``` wherein one or more of linker A, linker B or linker C is present; any combination of two or more oligonucleotides and one or more of linkers A-C is possible, so long as the polarity of the strands and the general structure of the molecule remains. Further, if two or more of linkers A-C are present, they may be identical or different.

Thus, a triple-armed structure is formed, wherein each arm comprises a sense strand and complementary antisense strand (i.e. Oligo1 antisense base pairs to Oligo1 sense etc.). The triple armed structure may be triple stranded, whereby each arm possesses base pairing.

Further, the above triple stranded structure may have a gap instead of a linker in one or more of the strands. Such a molecule with one gap is technically quadruple stranded and not triple stranded; inserting additional gaps or nicks will lead to the molecule having additional strands. Preliminary results obtained by the inventors of the present invention indicate that said gapped molecules are more active in inhibiting the TLR2, TLR4, MYD88, TICAM1 and TIRAP target gene than the similar but non-gapped molecules.

In some embodiments, neither antisense nor sense strands of the novel dsRNA compounds disclosed herein are phosphorylated at the 3' and 5' termini. In other embodiments either or both the sense and the antisense strands are phosphorylated at the 3' termini. In yet another embodiment, either or both the sense and the antisense strands are phosphorylated at the 3' termini using non-cleavable phosphate groups. In yet another embodiment, either or both the sense and the antisense strands are phosphorylated at the terminal 5' termini position using cleavable or non-cleavable phosphate groups. In yet another embodiment, either or both the sense and the antisense strands are phosphorylated at the terminal 2' termini position using cleavable or non-cleavable phosphate groups. In some embodiments the dsRNA compounds are blunt ended and are non-phosphorylated at the termini; however, comparative experiments have shown that dsRNA compounds phosphorylated at one or both of the 3'-termini have similar activity in vivo compared to the non-phosphorylated compounds.

Any dsRNA sequence disclosed herein can be prepared having any of the modifications/Structures disclosed herein. The combination of sequence plus structure is novel and can be used in the treatment of the conditions disclosed herein.

Unless otherwise indicated, in preferred embodiments of the structures discussed herein the covalent bond between each consecutive N and N' is a phosphodiester bond.

For all of the structures above, in some embodiments the oligonucleotide sequence of antisense strand is fully complementary to the oligonucleotide sequence of sense. In other embodiments the sense and the antisense strands are substantially complementary. In certain embodiments the antisense strand is fully complementary to about 18 to about 40 consecutive ribonucleotides a target mRNA set forth in any one of SEQ ID NOS:1-12.

In other embodiments the antisense strand is substantially complementary to about 18 to about 40 consecutive ribonucleotides a target mRNA set forth in any one of SEQ ID NOS:1-12.

In some embodiments, disclosed herein is an expression vector comprising an antisense oligonucleotide disclosed in any one of SEQ ID NOS: 13-20606. In some embodiments the expression vector further comprises a sense oligonucleotide having complementarity to the antisense oligonucleotide. In various embodiments are further provided a cell comprising an expression vector comprising a sense and an antisense oligonucleotide disclosed in any one of SEQ ID NOS: 13-20606 or 20602-20684. Further disclosed herein is a siRNA expressed in a cell comprising an expression vector comprising a sense and an antisense oligonucleotide disclosed in any one of SEQ ID NOS: 13-20606, or 20602-20684, a pharmaceutical composition comprising same and use thereof for treatment of any one of the disorders disclosed herein.

In other embodiments, disclosed herein is a first expression vector comprising an antisense oligonucleotide disclosed in any one of SEQ ID NOS: 13-20606 and a second expression vector comprising a sense oligonucleotide having complementarity to the antisense oligonucleotide comprised in the first expression vector. In various embodiments disclosed herein is a cell comprising a first expression vector comprising an antisense oligonucleotide disclosed in any one of SEQ ID NOS: 13-20606 and a second expression vector comprising a sense oligonucleotide having complementarity to the antisense oligonucleotide comprised in the first expression vector. Further disclosed herein is a dsRNA expressed in a cell comprising such first and second expression vector, a pharmaceutical composition comprising same and use thereof for treatment of any one of the diseases and disorders disclosed herein.

RNA Interference

RNA interference (RNAi) is a phenomenon involving double-stranded (ds) RNA-dependent gene specific post-transcriptional silencing. RNAi refers to the process of sequence-specific post-transcriptional gene silencing in mammals mediated by small interfering RNAs (siRNAs) (Fire et al, Nature 1998. 391, 806) or microRNAs (miRNA; Ambros, Nature 2004 431:7006, 350-55; and Bartel, Cell. 2004. 116(2):281-97). RNAi has been described in numerous publications, including Gil et al. Apoptosis, 2000. 5:107-114, Elbashir et al. Nature 2001, 411:494-498 and Caplen et al. PNAS USA 2001, 98:9742-9747. A siRNA is a double-stranded RNA molecule which inhibits, either partially or fully, the expression of a gene/mRNA of its endogenous or cellular counterpart, or of an exogenous gene such as a viral nucleic acid. The mechanism of RNA interference is detailed infra.

Studies have revealed that siRNA is effective in vivo in mammals, including humans. For reviews of therapeutic applications of siRNAs see for example Barik (Mol. Med 2005, 83: 764-773), Chakraborty (Current Drug Targets 2007 8(3):469-82); Durcan (Mol. Pharma. 2008. 5(4):559-566); Kim and Rossi (BioTechniques 2008. 44:613-616); Grimm and Kay, (JCI, 2007. 117(12):3633-41).

A number of PCT applications have been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

RNA interference (RNAi) is based on the ability of dsRNA species to enter a cytoplasmic protein complex, where it is then targeted to the complementary cellular RNA and specifically degrade it. The RNA interference response features an endonuclease complex containing a dsRNA, commonly referred to as an RNA-induced silencing complex (RISC), which mediates cleavage of single-stranded RNA having a sequence complementary to the antisense strand of the dsRNA duplex. Cleavage of the target RNA may take place in the middle of the region complementary to the antisense strand of the dsRNA duplex (Elbashir et al., Genes Dev., 2001, 15(2):188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., Nature, 2001, 409(6818):363-6; Lee et al., Nature, 2003, 425(6956):415-9). The RISC protein complex recognizes these fragments and complementary mRNA. The whole process is culminated by endonuclease cleavage of target mRNA (McManus & Sharp, Nature Rev Genet, 2002, 3(10): 737-47; Paddison & Hannon, Curr Opin Mol Ther. 2003, 5(3):217-24). (For additional information on these terms and proposed mechanisms, see for example Bernstein et al., RNA 2001, 7(11):1509-21; Nishikura, Cell 2001, 107(4): 415-8 and PCT publication WO 01/36646).

The selection and synthesis of dsRNA corresponding to known genes has been widely reported; see for example Ui-Tei et al., J Biomed Biotechnol. 2006; 2006: 65052; Chalk et al., BBRC. 2004, 319(1): 264-74; Sioud & Leirdal, Met. Mol Biol.; 2004, 252:457-69; Levenkova et al., Bioinform. 2004, 20(3):430-2; Ui-Tei et al., Nuc. Acid Res. 2004, 32(3):936-48. For examples of the use of, and production of, modified dsRNA see Braasch et al., Biochem., 2003, 42(26):7967-75; Chiu et al., RNA, 2003, 9(9):1034-48; PCT publications WO 2004/015107 (Atugen); WO 02/44321 (Tuschl et al), and U.S. Pat. Nos. 5,898,031 and 6,107,094.

dsRNA Synthesis

Using proprietary algorithms and the known sequence of the target genes disclosed herein, the sequences of many potential dsRNAs are generated. dsRNA molecules according to the above specifications are prepared essentially as described herein.

The dsRNA compounds disclosed herein are synthesized by any of the methods that are well known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Ann. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et al., in IRL Press 1989 edited by Oliver R. W. A.; Kap. 7: 183-208.

Other synthetic procedures are known in the art, e.g. the procedures described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides disclosed herein can be synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded RNAs are separated from the single-stranded oligonucleotides that were not annealed (e.g. because of the excess of one of them) by HPLC. In relation to the dsRNAs or dsRNA fragments disclosed herein, two or more such sequences can be synthesized and linked together for use herein.

The compounds disclosed herein can also be synthesized via tandem synthesis methodology, as described for example in US Patent Publication No. US 2004/0019001, wherein both dsRNA strands are synthesized as a single contiguous oligonucleotide fragment or strand separated by a cleavable linker which is subsequently cleaved to provide separate RNA fragments or strands that hybridize and permit purification of the RNA duplex. The linker is selected from a polynucleotide linker or a non-nucleotide linker.

Pharmaceutical Compositions

While it is possible for the compounds disclosed herein to be administered as the raw chemical, it is preferable to present them as a pharmaceutical composition. Accordingly disclosed herein is a pharmaceutical composition comprising one or more of the chemically modified dsRNA compounds disclosed herein; and a pharmaceutically acceptable excipient or carrier. In some embodiments the pharmaceutical composition comprises two or more novel dsRNA compounds as disclosed herein.

Further disclosed herein is a pharmaceutical composition comprising at least one double stranded RNA molecule covalently or non-covalently bound to one or more compounds disclosed herein in an amount effective to inhibit the TLR2, TLR4, MYD88, TICAM1 and TIRAP genes; and a pharmaceutically acceptable carrier. In some embodiments the dsRNA compounds are processed intracellularly by endogenous cellular complexes/enzymes to produce one or more molecules as disclosed herein.

Further disclosed herein is a pharmaceutical composition comprising a pharmaceutically acceptable carrier and one or more of the chemically modified dsRNA compounds disclosed herein in an amount effective to inhibit expression in a cell of a target gene, the compound comprising a sequence which is substantially complementary to the sequence of target mRNA, set forth in SEQ ID NOS:1-12. Preferred oligonucleotide sequences useful in generating double-stranded nucleic acid molecules for therapeutic use are set forth in SEQ ID NOS:13-5846 (targeting TLR2), SEQ ID NOS:5847-12144 (targeting TLR4), SEQ ID NOS:12145-16332 (targeting MYD88), SEQ ID NOS:16333-18242 (targeting TICAM1) and SEQ ID NOS:18243-20606 (targeting TIRAP), and preferably SEQ ID NOS:20607-20684.

In some embodiments, the dsRNA compounds disclosed herein are the main active component in a pharmaceutical composition. In other embodiments the dsRNA compounds disclosed herein are one of the active components of a pharmaceutical composition containing two or more dsRNAs, said pharmaceutical composition further being comprised of one or more additional dsRNA molecule which targets the genes disclosed herein. In other embodiments the dsRNA compounds disclosed herein are one of the active components of a pharmaceutical composition containing two or more dsRNAs, said pharmaceutical composition further being comprised of one or more additional dsRNA molecule which targets one or more additional gene. In some embodiments, simultaneous inhibition of the target gene by two or more dsRNA compounds as disclosed herein provides additive or synergistic effect for treatment of the diseases disclosed herein. In some embodiments, simultaneous inhibition of for example TLR2 gene and TLR4 provides additive or synergistic effect for treatment of the diseases disclosed herein.

In some embodiments, the dsRNA compounds disclosed herein are linked or bound (covalently or non-covalently) to an antibody or aptamer against cell surface internalizable molecules expressed on the target cells, in order to achieve enhanced targeting for treatment of the conditions disclosed herein. In one specific embodiment, anti-Fas antibody (preferably a neutralizing antibody) is combined (covalently or non-covalently) with a double stranded RNA molecule, such as an siRNA as disclosed herein. In various embodiments, an aptamer which acts like a ligand/antibody is combined (covalently or non-covalently) with a double stranded RNA molecule, such as an siRNA as disclosed herein.

Delivery

The chemically modified double stranded RNA molecule is administered as the compound per se (e.g. as naked siRNA) or as pharmaceutically acceptable salt and is administered alone or as an active ingredient in combination with one or more pharmaceutically acceptable carrier, solvent, diluent, excipient, adjuvant and vehicle. In some embodiments, the dsRNA molecules as disclosed herein are delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

Delivery systems aimed specifically at the enhanced and improved delivery of dsRNA into mammalian cells have been developed (see, for example, Shen et al FEBS Let. 539: 111-114 (2003), Xia et al., Nat. Biotech. 20: 1006-1010 (2002), Reich et al., Mol. Vision 9: 210-216 (2003), Sorensen et al., J. Mol. Biol. 327: 761-766 (2003), Lewis et al., Nat. Gen. 32: 107-108 (2002) and Simeoni et al., NAR 31, 11: 2717-2724 (2003)). siRNA has recently been successfully used for inhibition of gene expression in primates (see for example, Tolentino et al., Retina 2004. 24(1):132-138).

Pharmaceutically acceptable carriers, solvents, diluents, excipients, adjuvants and vehicles generally refer to inert, non-toxic solid or liquid fillers, diluents or encapsulating material not reacting with the active siRNA compounds disclosed herein. For example, the siRNA compounds disclosed herein may be formulated with polyethylenimine (PEI), with PEI derivatives, e.g. oleic and stearic acid modified derivatives of branched PEI, with chitosan or with poly(lactic-co-glycolic acid) (PLGA). Formulating the compositions in e.g. liposomes, micro- or nano-spheres and nanoparticles, may enhance stability and benefit absorption.

Additionally, the compositions may include an artificial oxygen carrier, such as perfluorocarbons (PFCs) e.g. perfluorooctyl bromide (perflubron), since different respiratory treatment modalities (e.g., liquid ventilation or aerosolized PFCs) have been shown to decrease pulmonary inflammatory responses in addition to improving lung compliance in animal models of lung injury and in clinical trials (Lehmler H J. 2008. Expert Review of Respiratory Medicine, vol. 2, No. 2: 273-289).

Examples of delivery systems as disclosed herein include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many such delivery systems, and modules are well known to those skilled in the art. In specific embodiments, formulations for inhalation are selected.

Accordingly, in some embodiments the siRNA molecules disclosed herein are delivered in liposome formulations and lipofectin formulations and the like and are prepared by methods well known to those skilled in the art. Such methods are described, for example, in U.S. Pat. Nos. 5,593,972, 5,589,466, and 5,580,859, which are herein incorporated by reference.

Additional formulations for improved delivery of the compounds as disclosed herein can include conjugation of siRNA molecules to a targeting molecule. The conjugate is usually formed through a covalent attachment of the targeting molecule to the sense strand of the siRNA, so as not to disrupt silencing activity. Potential targeting molecules useful herein include proteins, peptides and aptamers, as well as natural compounds, such as e.g. cholesterol. For targeting antibodies, conjugation to a protamine fusion protein has been used (see for example: Song et al., Antibody mediated in vivo delivery of small interfering RNAs via cell-surface receptors, Nat Biotechnol. 2005. 23(6):709-17).

The naked siRNA or the pharmaceutical compositions comprising the chemically modified siRNA as disclosed herein are administered and dosed in accordance with good medical practice, taking into account the clinical condition of the individual patient, the disease to be treated, the site and method of administration, scheduling of administration, patient age, sex, body weight and other factors known to medical practitioners.

A "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The siRNA disclosed herein can be administered in a single dose or in multiple doses.

In general, the active dose of a dsRNA compound for humans is in the range of from 1 ng/kg to about 20-100 mg/kg body weight per dose, preferably about 0.01 mg to about 2-10 mg/kg body weight per dose, in a regimen of a single dose or a series of doses given at short (e.g. 1-5 minute) intervals, administered within several minutes to several hours after perfusion.

The chemically modified dsRNA compounds as disclosed herein are administered by any of the conventional routes of administration. The chemically modified dsRNA compounds are administered orally, subcutaneously or parenterally including intravenous, intraarterial, intramuscular, intraperitoneally, intraocular, intracoronary, transtympanic and intranasal administration as well as intrathecal and infusion techniques. Implants of the compounds are also useful.

Liquid forms are prepared for invasive administration, e.g. injection or for topical or local administration. The term injection includes subcutaneous, transdermal, intravenous, intramuscular, intrathecal, intraocular, transtympanic and other parental routes of administration. The liquid compositions include aqueous solutions, with and without organic co-solvents, aqueous or oil suspensions, emulsions with edible oils, as well as similar pharmaceutical vehicles.

In embodiments wherein the subject has undergone lung transplantation, therapeutic compounds and compositions as disclosed herein are preferably administered into a of the subject by inhalation of an aerosol containing these compositions/compounds, by intranasal or intratracheal instillation of said compositions or by inhalation via ventilation machine (e.g. for administration to an unconscious patient). In some embodiments the siRNA compounds as disclosed herein are administered by inhalation into the lung of a subject who has undergone lung transplantation. For further information on pulmonary delivery of pharmaceutical compositions see Weiss et al., Human Gene Therapy 1999. 10:2287-2293; Densmore et al., Molecular therapy 1999. 1:180-188; Gautam et al., Molecular Therapy 2001. 3:551-556; and Shahiwala & Misra, AAPS PharmSciTech 2004. 24; 6(3):E482-6. Additionally, respiratory formulations for siRNA are described in U.S. Patent Application Publication No. 2004/0063654. Respiratory formulations for siRNA are described in US Patent Application Publication No. 2004/0063654. International Patent Publication No. WO 2008/132723 to the assignee of the present invention, and hereby incorporated by reference in its entirety discloses therapeutic delivery of siRNA to the respiratory system.

In some embodiments, the chemically modified dsRNA compounds as disclosed herein are formulated for systemic delivery for example by intravenous administration.

In addition, in certain embodiments the compositions for use in the novel treatments disclosed herein are formed as aerosols, for example for intranasal administration. In certain embodiments the compositions for use in the novel treatments disclosed herein are formed as nasal drops, for example for intranasal instillation.

Methods of Treatment

In one aspect disclosed herein is a method of treating a subject suffering from a posttransplantational complication, injury or condition associated with TLR2, TLR4, MYD88, TICAM1 and TIRAP expression or activity comprising administering to the subject a therapeutically effective amount of an siRNA compound as disclosed herein. In preferred embodiments the subject being treated is a warm-blooded animal and, in particular, mammal including human.

"Treating a subject" refers to administering to the subject a therapeutic substance effective to ameliorate symptoms associated with a condition, a complication or an injury, to lessen the severity or cure the condition, or to prevent the condition from occurring. "Treatment" refers to both therapeutic treatment and prophylactic or preventative measures, wherein the object is to prevent a condition, a complication or an injury or reduce the symptoms thereof. Those in need of treatment include those already experiencing the condition, those prone to having the condition, and those in which the condition is to be prevented. The compounds disclosed herein are administered before, during or subsequent to the onset of the condition. In various embodiments the subject is being treated after organ transplantation (such as lung transplantation) for a condition, a complication or an injury selected from, without being limited to, chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD).

A "therapeutically effective dose" refers to an amount of a pharmaceutical compound or composition which is effective to achieve an improvement in a subject or his physiological systems including, but not limited to, improved survival rate, more rapid recovery, or improvement or elimination of symptoms, and other indicators as are selected as appropriate determining measures by those skilled in the art.

The methods of treating the diseases disclosed herein include administering a TLR2, TLR4, MYD88, TICAM1 and TIRAP dsRNA inhibitor in conjunction or in combination with an additional inhibitor, a substance which improves the pharmacological properties of the active ingredient (e.g. siRNA) as detailed below, or an additional compound known to be effective in the treatment of a subject suffering from or susceptible to any of the hereinabove mentioned conditions, complications and disorders (e.g. immunosuppressants). In another aspect, provided herein is a combination of a therapeutic double stranded RNA molecule together with at least one additional therapeutically active agent. Additionally, the provided is a method of down-regulating the expression of a target gene by at least 40% as compared to a control, comprising contacting a target gene mRNA with one or more of the chemically modified RNA compounds as disclosed herein.

In one embodiment the chemically modified dsRNA compound as disclosed herein inhibits or down-regulates the mammalian TLR2, TLR4, MYD88, TICAM1 and TIRAP gene whereby the inhibition or down-regulation is selected from the group comprising inhibition of down-regulation of gene function, inhibition or down-regulation of polypeptide and inhibition and down-regulation of mRNA expression.

Disclosed herein is a method of inhibiting the expression of the TLR2, TLR4, MYD88, TICAM1 and TIRAP gene by at least 40%, preferably by 50%, 60% or 70%, more preferably by 75%, 80% or 90% as compared to a control comprising contacting an mRNA transcript of the TLR2, TLR4, MYD88, TICAM1 and TIRAP gene with one or more of the dsRNA compounds disclosed herein.

In one embodiment the effect of inhibition by the chemically modified siRNA compound disclosed herein is determined by examining siRNA effect on the mRNA or on the corresponding protein whereby the inhibition is selected from the group consisting of inhibition of function (which is examined by, for example, an enzymatic assay or a binding assay with a known interactor of the native gene/polypeptide, inter alia), inhibition of protein (which is examined by, for example, Western blotting, ELISA or immuno-precipitation, inter alia) and inhibition of target gene mRNA expression (which is examined by, for example, Northern blotting, quantitative RT-PCR, in-situ hybridization or microarray hybridization, inter alia).

In one embodiment the chemically modified double stranded RNA molecule is down-regulating the TLR2, TLR4, MYD88, TICAM1 and TIRAP gene or polypeptide, whereby the down-regulation is selected from the group consisting of down-regulation of function (which is examined by, for example, an enzymatic assay or a binding assay with a known interactor of the native gene/polypeptide, inter alia), down-regulation of protein (which is examined by, for example, Western blotting, ELISA or immuno-precipitation, inter alia) and down-regulation of target gene mRNA expression (which is examined by, for example, Northern blotting, quantitative RT-PCR, in-situ hybridization or microarray hybridization, inter alia).

In additional embodiments there is provided a method of treating a subject after organ transplantation (such as lung transplantation), wherein the subject is suffering from or susceptible to any condition, complication or disorder accompanied by an elevated level of a mammalian TLR2, TLR4, MYD88, TICAM1 and TIRAP gene, the method comprising administering to the subject a chemically modified siRNA compound or composition as disclosed herein in a therapeutically effective dose thereby treating the subject.

Provided herein is the use of a compound which down-regulates the expression of a mammalian gene selected from TLR2, TLR4, MYD88, TICAM1 and TIRAP gene, particularly to novel small interfering RNAs (siRNAs), in the treatment of chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD) in which inhibition of the expression of the mammalian TLR2, TLR4, MYD88, TICAM1 and TIRAP gene is beneficial.

Methods, novel chemically modified dsRNA molecules and pharmaceutical compositions comprising said dsRNA compounds which inhibit a mammalian TLR2, TLR4, MYD88, TICAM1 and TIRAP gene or polypeptide expression are discussed herein at length, and any of said dsRNA molecules and/or pharmaceutical compositions are beneficially employed in the treatment of a subject suffering from or susceptible to any of said conditions. It is to be explicitly understood that known compounds are excluded from the present invention. Novel methods of treatment using known compounds and compositions fall within the scope of the present invention.

The method disclosed herein includes administering a therapeutically effective amount of one or more of the chemically modified dsRNA compounds disclosed herein which down-regulate expression of a TLR2, TLR4, MYD88, TICAM1 and TIRAP gene.

Also disclosed herein is a process of preparing a pharmaceutical composition, which comprises:

providing one or more chemically modified double stranded RNA molecule; and admixing said compound with a pharmaceutically acceptable carrier.

In a preferred embodiment, the dsRNA compound used in the preparation of a pharmaceutical composition is admixed with a carrier in a pharmaceutically effective dose. In one embodiment the chemically modified dsRNA compound as disclosed herein is conjugated to a steroid or to a lipid or to another suitable targeting molecule e.g. to protein, peptide, aptamer, natural compound (e.g. cholesterol, xylose).

Combination Therapy

The methods of treating the diseases disclosed herein include administering a novel chemically modified double stranded RNA molecule in conjunction or in combination with an additional TLR2, TLR4, MYD88, TICAM1 and TIRAP inhibitor, a substance which improves the pharmacological properties of the chemically modified dsRNA compound, or an additional compound known to be effective in the treatment of a subject suffering from or susceptible to a complication or injury post organ transplantation, for example lung transplantation, such as, without being limited to, primary graft failure, ischemia-reperfusion injury, reperfusion injury, reperfusion edema, allograft dysfunction, pulmonary reimplantation response and/or primary graft dysfunction (PGD), chronic or acute aseptic inflammation, or neuropathic pain.

In another aspect, provided herein is a pharmaceutical composition comprising a combination of a therapeutic double stranded RNA molecule together with at least one additional therapeutically active agent. By "in conjunction with" or "in combination with" is meant prior to, simultaneously or subsequent to. Accordingly, the individual components of such a combination are administered either sequentially or simultaneously from the same or separate pharmaceutical formulations.

Combination therapies comprising known treatments for treating a subject prone to a complication or injury post organ transplantation, for example, lung transplantation, such as, without being limited to, primary graft failure, ischemia-reperfusion injury, reperfusion injury, reperfusion edema, allograft dysfunction, pulmonary reimplantation response and/or primary graft dysfunction (PGD), in conjunction with the novel chemically modified dsRNA compounds and therapies described herein are considered part of the current invention. Such known treatments include, without being limited to, pharmacological immunosuppression.

In addition, the dsRNA compounds disclosed herein are used in the preparation of a medicament for use as adjunctive therapy with a second therapeutically active compound (e.g. immunosuppressive agent) to treat such conditions. Appropriate doses of known second therapeutic agent for use in combination with a chemically modified double stranded RNA molecule are readily appreciated by those skilled in the art.

In some embodiments the combinations referred to above are presented for use in the form of a single pharmaceutical formulation.

The administration of a pharmaceutical composition comprising any one of the pharmaceutically active siRNA compounds disclosed herein is carried out by any of the many known routes of administration, including intravenously, intra-arterially, by intranasal or intratracheal instillation or by inhalation as determined by a skilled practitioner. Using specialized formulations, it is possible to administer the compositions intracoronary, via inhalation or via intranasal instillation.

By "in conjunction with" is meant that the additional pharmaceutically effective compound is administered prior to, at the same time as, or subsequent to administration of the pharmaceutical compositions of present invention. The individual components of such a combination referred to above, therefore, are administered either sequentially or simultaneously from the same or separate pharmaceutical formulations. As is the case for the present siRNA compounds, a second therapeutic agent is administered by any as detailed above, for example, but not limited to oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, a chemically modified double stranded RNA molecule disclosed herein and the second therapeutic agent are administered by the same route, either provided in a single composition or as two or more different pharmaceutical compositions. However, in other embodiments, a different route of administration for the novel double stranded RNA molecule disclosed herein and the second therapeutic agent is possible. Persons skilled in the art are aware of the best modes of administration for each therapeutic agent, either alone or in combination.

In another aspects, provided herein is a pharmaceutical composition comprising two or more dsRNA molecules for the treatment of any of the complications and conditions mentioned herein. In some embodiments the two or more dsRNA molecules or formulations comprising said molecules are admixed in the pharmaceutical composition in amounts which generate equal or otherwise beneficial activity. In certain embodiments the two or more dsRNA molecules are covalently or non-covalently bound, or joined together by a nucleic acid linker of a length ranging from 2-100, preferably 2-50 or 2-30 nucleotides. In one embodiment, the two or more dsRNA molecules target mRNA to TLR2, TLR4, MYD88, TICAM1 and TIRAP. In some embodiments at least one of the two or more dsRNA compounds target TLR2, TLR4, MYD88, TICAM1 and TIRAP RNA. In some embodiments at least one of the RNA compounds comprises an antisense sequence substantially identical to an antisense sequence set for the in any one of SEQ ID NOS: 13-20606. In some embodiments the dsRNA sense and antisense oligonucleotides are selected from sense and corresponding (complementary) antisense oligonucleotides set forth in any one of SEQ ID NOS: 13-20606. Preferred sense and antisense oligonucleotide pairs are set forth in Tables 1-5, herein below.

In some embodiments the pharmaceutical compositions disclosed herein further comprise one or more additional dsRNA molecule, which targets one or more additional gene. In some embodiments, simultaneous inhibition of said additional gene(s) provides an additive or synergistic effect for treatment of the complication, injury or disorder disclosed herein.

The treatment regimen disclosed herein is carried out, in terms of administration mode, timing of the administration, and dosage, so that the functional recovery of the patient from the adverse consequences of the conditions disclosed herein is improved.

In some embodiments the pharmaceutical compositions disclosed herein further comprise one or more additional dsRNA molecule, which targets one or more additional gene. In some embodiments, simultaneous inhibition of said additional gene(s) provides an additive or synergistic effect for treatment of the diseases disclosed herein.

The treatment regimen disclosed herein is carried out, in terms of administration mode, timing of the administration, and dosage, so that the functional recovery of the patient from the adverse consequences of the conditions disclosed herein is improved or so as to postpone the onset of a disorder. Effective concentrations of individual nucleic acid molecule in a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

An appropriate dosage for a mammal may be from 0.01 mg to 1 g per kg of body weight (e.g., 0.1 mg, 0.25 mg, 0.5 mg, 0.75 mg, 1 mg, 2.5 mg, 5 mg, 10 mg, 25 mg, 50 mg, 100 mg, 250 mg, 500 mg, 1 mg, 2.5 mg, 5 mg, 10 mg, 25 mg, 50 mg, 100 mg, 250 mg, or 500 mg per kg).

Dosage levels of from about 0.01 mg to about 100 mg per kilogram of body weight per day are useful in the treatment of the above-indicated conditions. The amount of active ingredient that can be combined with a carrier to produce a single dosage form varies depending upon the host treated and the particular mode of administration. Dosage unit forms generally contain between from about 0.1 mg to about 500 mg of an active ingredient. Dosage units may be adjusted for local delivery, for example for intravitreal delivery of for transtympanic delivery.

Kits

In another aspect a kit is provided comprising a therapeutic agent consisting of a double-stranded nucleic acid that targets TLR2; optionally with instructions for use. In some embodiments the double-stranded nucleic acid that targets TLR2 comprises a oligonucleotide having a sequence set forth in SEQ ID NOS:13-5846.

In another aspect a kit is provided comprising a therapeutic agent consisting of a double-stranded nucleic acid that targets TLR4; optionally with instructions for use. In some embodiments the double-stranded nucleic acid that targets TLR4 comprises a oligonucleotide having a sequence set forth in SEQ ID NOS:5847-12144.

In another aspect a kit is provided comprising a therapeutic agent consisting of a double-stranded nucleic acid that targets MYD88; optionally with instructions for use. In some embodiments the double-stranded nucleic acid that targets MYD88 comprises a oligonucleotide having a sequence set forth in SEQ ID NOS:12145-16332.

In another aspect a kit is provided comprising a therapeutic agent consisting of a double-stranded nucleic acid that targets TICAM1; optionally with instructions for use. In some embodiments the double-stranded nucleic acid that targets TICAM1 comprises a oligonucleotide having a sequence set forth in SEQ ID NOS:16333-18242.

In another aspect a kit is provided comprising a therapeutic agent consisting of a double-stranded nucleic acid that targets TIRAP; optionally with instructions for use. In some embodiments the double-stranded nucleic acid that targets TIRAP comprises a oligonucleotide having a sequence set forth in SEQ ID NOS:18243-20606.

In another aspect provided is a kit comprising at least two therapeutic agents wherein the two agents are selected from the group consisting of a TLR2 inhibitor, a TLR4 inhibitor, a MYD88 inhibitor, a TICAM1 inhibitor and a TIRAP inhibitor; optionally with instructions for use.

In some embodiments of the kit each therapeutic agent is independently selected from the group consisting of a short interfering nucleic acid (siNA), a short interfering RNA (siRNA), a double-stranded RNA (dsRNA), a micro-RNA (miRNA) or short hairpin RNA (shRNA) that binds a nucleotide sequence (such as an mRNA sequence) encoding the target gene selected from TLR2, TLR4, MYD88, TICAM1 and TIRAP. In some embodiments each nucleic acid molecule is a double-stranded RNA (dsRNA) or a short interfering RNA (siRNA). In some embodiments each nucleic acid molecule is selected from the group consisting of a dsRNA targeting TLR2, TLR4, MYD88, TICAM1 and TIRAP. In some embodiments the kit provided herein comprises a combined inhibitor by which it is meant a single agent which is capable of inhibiting at least two genes and/or gene products selected from the group consisting of TLR2, TLR4, MYD88, TICAM1 and TIRAP; optionally with instructions for use.

In some embodiments each therapeutic agent of the kit comprises a nucleic acid molecule, wherein:
(a) the nucleic acid molecule includes a sense strand and an antisense strand;
(b) each strand of the nucleic acid molecule is independently 17 to 40 nucleotides in length;
(c) a 17 to 40 nucleotide sequence of the antisense strand is complementary to a sequence of an mRNA selected from an mRNA encoding TLR2, TLR4, MYD88, TICAM1 or TIRAP
(d) a 17 to 40 nucleotide sequence of the sense strand is complementary to the antisense strand and includes a 17 to 40 nucleotide sequence of a mRNA selected from a mRNA encoding TLR2, TLR4, MYD88, TICAM1 or TIRAP.

Indications
Lung Injury, Lung Ischemia Reperfusion Injury
Lung Transplantation

Lung transplantation is a surgical procedure in which a patient's diseased lungs are partially or totally replaced by lungs which come from a donor. Lung transplantation has become a treatment of choice for patients with advanced/end-stage lung diseases. Within last decades, donor management, organ preservation, immunosuppressive regimens and control of infectious complications have been substantially improved and the operative techniques of transplantation procedures have been developed. Nonetheless, primary graft dysfunction (PGD) affects an estimated 10 to 25% of lung transplants and is the leading cause of early post-transplantation morbidity and mortality for lung recipients (Lee J C and Christie J D. 2009. Proc Am Thorac Soc, vol. 6: 39-46). PGD has variably been referred to as primary graft failure, ischemia-reperfusion injury, reperfusion injury, reperfusion edema, allograft dysfunction, and pulmonary reimplantation response. In addition, there is some evidence to suggest a relationship between reperfusion injury, acute rejection, and the subsequent development of chronic graft dysfunction.

Effective oligonucleotide based therapies useful in preventing or treating chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, would be of great therapeutic value.

In various embodiments the chemically modified dsRNA compounds disclosed herein are useful for treating or preventing complications or injury post lung transplantation, such as, without being limited to, chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD).

The term "lung transplantation" is meant to encompass a surgical procedure in which a patient's diseased lungs are partially or totally replaced by lungs which come from a donor. Although a xenotransplant can be contemplated in certain situations, an allotransplant is usually preferable.

Indications for lung transplantation include chronic obstructive pulmonary disease (COPD), pulmonary hypertension, cystic fibrosis, idiopathic pulmonary fibrosis, and Eisenmenger syndrome. Typically, four different surgical techniques are used: single-lung transplantation, bilateral sequential transplantation, combined heart-lung transplantation, and lobar transplantation, with the majority of organs obtained from deceased donors.

The dsRNA compounds disclosed herein are particularly useful in treating a subject experiencing a medical complication of lung transplantation, including, without being limited to, ameliorating, attenuating, treating or preventing any of the following: chronic or acute aseptic inflammation, neuropathic pain, primary graft failure, ischemia-reperfusion injury, reperfusion injury, reperfusion edema, allograft dysfunction, pulmonary reimplantation response and/or primary graft dysfunction (PGD).

In some embodiments the target gene is selected from MYD88, TICAM1, TLR2, TLR4 and TIRAP. In yet other embodiments the sense and antisense oligonucleotide sequences useful in synthesizing siRNA compounds are set forth in set forth in SEQ ID NOS:13-5846 (targeting TLR2), SEQ ID NOS:5847-12144 (targeting TLR4), SEQ ID NOS: 12145-16332 (targeting MYD88), SEQ ID NOS:16333-18242 (targeting TICAM1) and SEQ ID NOS:18243-20606 (targeting TIRAP).

Acute Lung Injury (ALI)/Acute Respiratory Distress Syndrome (ARDS)

Acute respiratory distress syndrome (ARDS), also known as respiratory distress syndrome (RDS) is a serious reaction to various forms of injuries to the lung. This is the most relevant disorder resulting in increased permeability pulmonary edema ARDS is a severe lung disease caused by a variety of direct and indirect insults. It is characterized by inflammation of the lung parenchyma leading to impaired gas exchange with concomitant systemic release of inflammatory mediators which cause inflammation, hypoxemia and frequently result in failure of multiple organs. This condition is life threatening and often lethal, usually requiring mechanical ventilation and admission to an intensive care unit. A less severe form is called acute lung injury (ALI).

In some embodiments the molecules and methods disclosed herein are useful for treating or preventing the incidence or severity of acute lung injury, in particular conditions which result from ischemic/reperfusion injury or oxidative stress. For example, acute respiratory distress syndrome (ARDS) due to coronavirus infection or endotoxins, severe acute respiratory syndrome (SARS), ischemia reperfusion injury associated with lung transplantation and other acute lung injuries.

Inflammatory Conditions

Inflammatory conditions where the present compounds find use are asthmatic conditions, Crohn's disease, ulcerous colitis, reperfusion injury, auto-immune diseases, inflammatory bowel disease (IBD), atherosclerosis, restenosis, coronary heart disease, diabetes, rheumatoidal diseases, dermatological diseases, such as psoriasis and seborrhea, graft rejection, and inflammation of the lungs, heart, kidney, oral cavity, uterus.

Neuropathic Pain

Neuropathic pain is complex, chronic pain state often accompanied by tissue injury or dysfunction. Neuropathic pain may occur due to lesions or diseases affecting the somatosensory system and is characterized by hyperalgesia, spontaneous pain and allodynia. Allodynia is pain in response to a nonnociceptive stimulus or pain due to a stimulus which does not normally provoke a pain response and can be elicited as a hypersensitivity to either thermal or mechanical stimuli that are not normally sensed as pain.

Neuropathic pain may be caused by spinal cord injury (SCI), or injury of peripheral nerves (PNI), dorsal root ganglions or the brain. In humans, chronic pain elicited as burning, stabbing and/or electric-like sensations can develop within months after injury. Another cause of neuropathic pain is diabetes mellitus. Diabetic neuropathy is one of the most common complications of diabetes mellitus and allodynia is one of its symptoms. Additional causes of neuropathic pain include herpes zoster infection, HIV-related neuropathies, limb amputation, nutritional deficiencies, toxins, genetic and immune mediated disorders. Neuropathic pain may appear in cancer patients due to tumors pressing on peripheral nerves or as a side effect of treatment (e.g. chemotherapy with taxanes).

Allodynia and Spinal Cord Injury (SCI)

Chronic pain is one of the more frequent and troublesome sequelae of SCI, often interfering with the effective rehabilitation of the patient. In addition to the chronic pain syndromes seen in the non-SCI population, e.g., migraine and postherpetic neuralgia, patients with SCI may also suffer from pain syndromes unique to SCI. The reported prevalence of chronic SCI pain varies between 25% and 94%, with almost one-third of these patients experiencing severe pain (Bonica J J. Introduction: semantic, epidemiologic, and educational issues. In: Casey K L, ed. Pain and central nervous system disease: the central pain syndromes. New York: Raven Press, 1991:13-29; Siddall P J, et al. Pain 1999; 81:187-97; Gerhart K A, et al. Paraplegia 1992; 30:282-7). Several studies have reported the prevalence of the various types of SCI pain. Musculoskeletal pain was the most common type experienced at 6 mo after injury (40%) (Siddall P J, *Pain* 1999; 81:187-97) and at 5 yr after SCI (59%) (Siddall P J, et al. Pain 2003; 103:249-57). An increase in the prevalence of at-level and below-level neuropathic pain has likewise been observed more than 5 yr after SCI. Variables that influence the development of SCI pain remain unclear. Factors such as the level of the injury, completeness of the injury, cause of injury, and psychosocial factors have been considered (Siddall P J, et al. In: Yezierski R P, Burchiel K J, eds. *Spinal cord injury pain: assessment, mechanisms, management. Progress in Pain Research and Management*. Vol. 23 Seattle: IASP Press, 2002:9-24). Musculoskeletal pain was more common in patients with thoracic level injuries and was reported to be more prevalent in those who had surgical intervention 2 wk after SCI (Sved P, et al. Spinal Cord 1997; 35:526-30). Neuropathic pain that was associated with allodynia was observed to be more common in patients with incomplete spinal cord lesions, in cervical than thoracic cord injuries, and in central cord syndrome (Siddall P J, et al. *Pain* 1999; 81:187-97).

Post-SCI Pain Types

In addition to the four major types of SCI pain under Tier 2, there are other recognized pain conditions, most of which are under Tier 3 in the International Association for the Study of Pain Taxonomy (Siddall P J, et al. International Association for the Study of Pain Newsletter 2000; 3:3-7). These need to be clinically identified so that appropriate treatment may be instituted.

Musculoskeletal Pain

Mechanical Instability of the Spine: This type of pain is brought about by disruption of ligaments/joints or fractures of bone, resulting in instability of the spine. It occurs early after injury and is located in the region of the spine close to the site of SCI. It is related to position, worsened by activity and decreased by rest. Diagnosis is aided by radiographs, computerized tomography or MRI to identify the nature and site of pathology.

Muscle Spasm Pain: Spasticity is defined as a motor disorder characterized by a velocity-dependent increase in the tonic stretch reflexes (muscle tone) with exaggerated tendon reflexes, resulting from hyperexcitability of the stretch reflex. An imbalance in any of the numerous excitatory and inhibitory modulatory synaptic influences on the $\alpha$ motor neuron and muscle results in hyperactivity of the stretch reflex arc. This pain type usually occurs late after SCI, and is often seen in people with incomplete SCI.

At-Level Neuropathic Pain

Segmental deafferentation/Girdle or Border or transitional zone pain: This is a variation of at-level neuropathic pain that occurs within a band of two to four segments above or below the level of SCI. It often occurs on the border of normal sensation and anesthetic skin.

Syringomyelia: Pain due to a syrinx (i.e., an abnormal cyst in the spinal cord) often occurs with a delayed onset, a mean of 6 yr. The damage to the central part of the spinal cord with cervical injuries results in the central cord syndrome characterized by pain and weakness of the arms and relatively strong but spastic leg function. The pain of syringomyelia is sometimes described as a constant burning pain with allodynia.

Below-Level Neuropathic Pain

Central dysaesthesia syndrome/central pain/deafferentation pain: pain diffusely located caudal to the level of SCI, i.e., over the entire body from the shoulders to the feet, typical of below-level neuropathic pain. The pain may be associated with hyperalgesia and may gradually worsen over time. It occurs with spontaneous and/or evoked episodes, and is often worsened by infections, sudden noise, and jarring movements.

Pathophysiology and Mechanisms of SCI Pain

Pain associated with SCI is a consequence of both injury characterized by pathological changes from mechanical trauma and vascular compromise of the cord parenchyma. It is influenced by the nature of the lesion, the neurological structures damaged, and the secondary pathophysiological changes of the surviving tissue. There are at least three proposed basic mechanisms underlying SCI pain: increased neuronal hyperexcitability, reduced inhibition, and neuronal reorganization or plasticity.

Increased Neuronal Hyperexcitability

An initial consequence of SCI after traumatic or ischemic SCI is the brief but dramatic increase of excitatory amino acids, which triggers an injury cascade of secondary pathological changes. The major components of this spinal "central injury cascade" include anatomical, neurochemical, excitotoxic, and inflammatory events that collectively interact to increase the responsiveness of the neurons at the level of injury, resulting in the generation of the clinical symptoms of allodynia and hyperalgesia (Yezierski R P. *Pathophysiology and animal models of spinal cord injury pain*. In: Yezierski R P, Burchiel K J, eds. *Spinal cord injury pain: assessment, mechanisms, management. Progress in pain research and management*. Vol. 23. Seattle: IASP Press, 2002:117-36).

Periodontitis

Periodontitis occurs when inflammation or infection of the gums is left untreated or treatment is delayed. Infection and inflammation spreads from the gingiva to the ligaments and bone that support the teeth, ultimately resulting in tooth loss. Inflammation caused by plaque and tartar accumulating at the base of the teeth traps the plaque in a pocket that forms between the teeth and the gingiva. Continued inflammation eventually causes destruction of the tissues and bone surrounding the tooth.

Synthesis of Modified Compounds

The compounds disclosed herein can be synthesized by any of the methods that are well known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., J. Am. Chem. Soc., 1987, 109:7845; Scaringe et al., NAR, 1990, 18:5433; Wincott et al., NAR 1995. 23:2677-2684; and Wincott et al., Methods Mol. Bio., 1997, 74:59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides disclosed herein can be synthesized separately and joined together post-synthetically, for example, by ligation (Moore et al., Science 1992, 256:9923; International Patent Publication No. WO 93/23569; Shabarova et al., NAR 1991, 19:4247; Bellon et al., Nucleosides & Nucleotides, 1997, 16:951; Bellon et al., Bioconjugate Chem 1997, 8:204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded oligonucleotides are separated from the single-stranded oligonucleotides that were not annealed (e.g. because of the excess of one of them) by HPLC. In relation to the siRNAs or siRNA fragments disclosed herein, two or more such sequences can be synthesized and linked together for use herein.

The compounds as disclosed herein can also be synthesized via tandem synthesis methodology, as described for example in US Patent Publication No. 2004/0019001 (McSwiggen), wherein both dsRNA strands are synthesized as a single contiguous oligonucleotide fragment or strand separated by a cleavable linker which is subsequently cleaved to provide separate RNA fragments or strands that hybridize and permit purification of the RNA duplex. The linker is selected from a polynucleotide linker or a non-nucleotide linker.

The term "Covalent bonding" as used herein refers to chemical bonding that is characterized by the sharing of pairs of electrons between atoms.

The term "noncovalent bonding" as used herein refers to a variety of interactions that are not covalent in nature between molecules or parts of molecules that provide force to hold the molecules or parts of molecules together, usually in a specific orientation or conformation. These noncovalent interactions include: ionic bonds, hydrophobic interactions, hydrogen bonds, Van der Waals forces and dipole-dipole bonds.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out as in standard PCR Protocols: A Guide To Methods And Applications, Academic Press, San Diego, Calif. (1990). In situ PCR in combination with Flow Cytometry (FACS) can be used for detection of cells containing specific DNA and mRNA sequences (Testoni et al., Blood 1996, 87:3822.) Methods of performing qPCR and RT-PCR are well known in the art.

Example 1

Generation of Sequences for Active siRNA Compounds to the Target Genes and Production of the siRNAs Using proprietary algorithms and the known sequence of the genes of disclosed herein, the antisense and corresponding sense sequences of siRNA were generated. In addition to the algorithm, 20-, 21-, 22-, and 23-mer oligomer sequences are generated by 5' and/or 3' extension of the 19-mer sequences. The sequences that have been generated using this method are fully complementary to a segment of corresponding mRNA sequence.

SEQ ID NOS; 13-20606 provide oligonucleotide sequences useful in the preparation of dsRNA compounds as disclosed herein. Each oligonucleotide sequence is presented in 5' to 3' orientation.

For each gene there is a separate list of 19-mer sense and corresponding antisense oligonucleotide sequences, which are prioritized based on their score in the proprietary algorithm as the best sequences for targeting the human gene expression.

The dsRNA compounds disclosed herein are synthesized by any methods described herein, infra.

Tables 1-5 hereinbelow provide sequence pairs useful in generating double stranded nucleic acid molecules.

TABLE 1

Selected oligonucleotides useful in generating double-stranded nucleic acid compounds to target TLR2.

| name | SEQ ID NO: | SENSE 5'>3' | SEQ ID NO | ANTISENSE 5'>3' | Structure |
|---|---|---|---|---|---|
| TLR2_25 | 20607 | GGGUGGAGAACCUUAUGGU | 20614 | ACCAUAAGGUUCUCCACCC | A1 |
| TLR2_28 | 20608 | GGCAAGUGGAUCAUUGACA | 20615 | UGUCAAUGAUCCACUUGCC | A1 |
| TLR2_42 | 20609 | GGGUAAAUCUGAGAGCUGC | 20616 | GCAGCUCUCAGAUUUACCC | A1 |
| TLR2_43 | 20610 | CCAUUGAAAAGAGCCACAA | 20617 | UUGUGGCUCUUUUCAAUGG | A1 |
| TLR2_47 | 20611 | AUAAUGAACACCAAGACCU | 20618 | AGGUCUUGGUGUUCAUUAU | A1 |
| TLR2_31 | 20612 | GGUAAAUCUGAGAGCUGCA | 20619 | UGCAGCUCUCAGAUUUACC | A2 |
| TLR2_34 | 20613 | CUGGACUUCUCCCAUUUCA | 20620 | UGAAAUGGGAGAAGUCCAG | A2 |

TABLE 2

Selected oligonucleotides useful in generating double-stranded nucleic acid compounds to target TLR4.

| name | SEQ ID NO | SENSE 5'>3' | SEQ ID NO | ANTISENSE 5'>3' | Structure |
|---|---|---|---|---|---|
| TLR4_08 | 20621 | AACUUAAUGUGGCUCACAA | 20630 | UUGUGAGCCACAUUAAGUU | A1 |
| TLR4_10 | 20622 | GGCUGGCAAUUCUUUCCAA | 20631 | UUGGAAAGAAUUGCCAGCC | A1 |
| TLR4_11 | 20623 | GAUUUAUCCAGGUGUGAAA | 20632 | UUUCACACCUGGAUAAAUC | A1 |
| TLR4_14 | 20624 | CUCAAUCUCUCUUUAGACA | 20633 | UGUCUAAAGAGAGAUUGAG | A1 |
| TLR4_15 | 20625 | CGCUGGUGUAUCUUUGAAA | 20634 | UUUCAAAGAUACACCAGCG | A1 |
| TLR4_28 | 20626 | AAAAUGGCUGGCAAUUCUA | 20635 | UAGAAUUGCCAGCCAUUUU | A1 |
| TLR4_29 | 20627 | AGCCGCUGGUGUAUCUUUG | 20636 | CAAAGAUACACCAGCGGCU | A1 |
| TLR4_31 | 20628 | AAAUGGCUGGCAAUUCUUA | 20637 | UAAGAAUUGCCAGCCAUUU | A1 |
| TLR4_33 | 20629 | AUGGCUGGCAAUUCUUUCA | 20638 | UGAAAGAAUUGCCAGCCAU | A1 |

TABLE 3

Selected oligonucleotides useful in generating a
double-stranded nucleic acid compound to target MYD88

| name | SEQ ID NO | SENSE 5'>3' | SEQ ID NO | ANTISENSE 5'>3' | Structure |
|---|---|---|---|---|---|
| MYD88_11 | 12178 | GAAUGUGACUUCCAGACCA | 12660 | UGGUCUGGAAGUCACAUUC | A1 |

TABLE 4

Selected oligonucleotides useful in generating
double-stranded nucleic acid compounds to target TICAM1

| name | SEQ ID NO: | SENSE 5'>3' | SEQ ID NO | ANTISENSE 5'>3' | Structure |
|---|---|---|---|---|---|
| TICAM1_15 | 20639 | GGGUGAAGGGUCUUGGUGA | 20650 | UCACCAAGACCCUUCACCC | A2 |
| TICAM1_16 | 20640 | CUGGAAUCAUCAUCGGAAA | 20651 | UUUCCGAUGAUGAUUCCAG | A2 |
| TICAM1_17 | 20641 | GGACGAACACUCCCAGAUA | 20652 | UAUCUGGGAGUGUUCGUCC | A2 |
| TICAM1_18 | 20642 | GGCACUGAACGCAGCCUAA | 20653 | UUAGGCUGCGUUCAGUGCC | A2 |
| TICAM1_19 | 20643 | CCAGCAACUUGGAAAUCAA | 20654 | UUGAUUUCCAAGUUGCUGG | A2 |
| TICAM1_20 | 20644 | AGCCCUUCAUUUAGGACAA | 20655 | UUGUCCUAAAUGAAGGGCU | A1 |
| TICAM1_21 | 20645 | GGGUAUUGCUACGGUCUUA | 20656 | UAAGACCGUAGCAAUACCC | A2 |
| TICAM1_22 | 20646 | CCGGGAGCCCUUCAUUUAA | 20657 | UUAAAUGAAGGGCUCCCGG | A2 |
| TICAM1_23 | 20647 | GGCAGAAUGACCGCGUGUA | 20658 | UACACGCGGUCAUUCUGCC | A2 |
| TICAM1_24 | 20648 | GCGCCUUCGACAUUCUAGA | 20659 | UCUAGAAUGUCGAAGGCGC | A2 |
| TICAM1_25 | 20649 | CCUACUUCUCACCUCCAAA | 20660 | UUUGGAGGUGAGAAGUAGG | A2 |

TABLE 5

Selected oligonucleotides useful in generating
double-stranded nucleic acid compounds to target TIRAP.

| name | SEQ ID NO: | SENSE 5'>3' | SEQ ID NO | ANTISENSE 5'>3' | structure |
|---|---|---|---|---|---|
| TIRAP_16 | 20661 | CUAAGAAGCCUCUAGGCAA | 20673 | UUGCCUAGAGGCUUCUUAG | A1 |
| TIRAP_17 | 20662 | UAAGAAGCCUCUAGGCAAA | 20674 | UUUGCCUAGAGGCUUCUUA | A2 |
| TIRAP_18 | 20663 | GGAGCAAAGACUAUGACGA | 20675 | UCGUCAUAGUCUUUGCUCC | A2 |
| TIRAP_19 | 20664 | GCAAAGACUAUGACGUCUA | 20676 | UAGACGUCAUAGUCUUUGC | A2 |
| TIRAP_20 | 20665 | GGCGCUAUAGUGUCCGAGA | 20677 | UCUCGGACACUAUAGCGCC | A2 |
| TIRAP_21 | 20666 | GCCUCAGCUCAGUCACGUA | 20678 | UACGUGACUGAGCUGAGGC | A2 |
| TIRAP_22 | 20667 | CUAAGAAGCCUCUAGGCAU | 20679 | AUGCCUAGAGGCUUCUUAG | A2 |
| TIRAP_23 | 20668 | GCUUCACAGCCUACCUCAA | 20680 | UUGAGGUAGGCUGUGAAGC | A2 |

TABLE 5-continued

Selected oligonucleotides useful in generating
double-stranded nucleic acid compounds to target TIRAP.

| name | SEQ ID NO: | SENSE 5'>3' | SEQ ID NO | ANTISENSE 5'>3' | structure |
|---|---|---|---|---|---|
| TIRAP_24 | 20669 | UAAGAAGCCUCUAGGCAAU | 20681 | AUUGCCUAGAGGCUUCUUA | A2 |
| TIRAP_25 | 20670 | CAAAGAAGCUGUCAUGCGA | 20682 | UCGCAUGACAGCUUCUUUG | A2 |
| TIRAP_26 | 20671 | GGUGCAAGUACCAGAUGCA | 20683 | UGCAUCUGGUACUUGCACC | A2 |
| TIRAP_27 | 20672 | GCUCCGAUUCAUGUACUAA | 20684 | UUAGUACAUGAAUCGGAGC | A2 |

Table 6 hereinbelow provides a sequence code of the modified nucleotides/unconventional moieties utilized in preparing the dsRNA oligonucleotides according to Structure (A1)

| Name | Batch Number | Sense 5->3 | Antisense 5->3 |
|---|---|---|---|
| MYD88_1_S129 | 138977 | rU; rC; rG; rA; rU; rG; rC; rC; rU; rU; rC; rA; rU; rC; rU; rG; rC; LdT; rA$ | mU; rA; mG; rC; mA; rG; mA; rU; mG; rA; mA; rG; mG; rC; mA; rU; mC; rG; mA$ |
| MYD88_1_S505 | 138978 | rU; rC; rG; rA; rU; rG; rC; rC; rU; rU; rC; rA; rU; rC; rU; rG; rC; LdT; rA$ | rU; mA; rG; mC; rA; mG; rA; mU; rG; rA; mA; rG; mG; rC; mA; rU; mC; rG; mA$ |
| MYD88_11_S129 | 138983 | rG; rA; rA; rU; rG; rU; rG; rA; rC; rU; rU; rC; rC; rA; rG; rA; rC; LdC; rA$ | mU; rG; mG; rU; mC; rU; mG; rG; mA; rA; mG; rU; mC; rA; mC; rA; mU; rU; mC$ |
| MYD88_11_S505 | 138984 | rG; rA; rA; rU; rG; rU; rG; rA; rC; rU; rU; rC; rC; rA; rG; rA; rC; LdC; rA$ | rU; mG; rG; mU; rC; mU; rG; mG; rA; rA; mG; rU; mC; rA; mC; rA; mU; rU; mC$ |
| MYD88_11_S870 | 60241388 | c6Np; rG; mA; rA; mU; rG; mU; rG; mA; rC; mU; rU; mC; rC; mA; rG; mA; rC; mC; rA$ | mU; rG; mG; rU; mC; rU; mG; rG; mA; rA; mG; rU; mC; rA; mC; rA; mU; rU; mC; dT; dT$ |
| MYD88_11_S871 | 60241391 | c6Np; rG; mA; rA; mU; rG; mU; rG; mA; rC; mU; rU; mU; mC; dC; mA; rG; mA; dC; dC; rA$ | mU; rG; rG; dT; mC; dT; mG; rG; mA; rA; mG; dT; mC; rA; mC; rA; mU; dT; mC; dT; dT$ |
| MYD88_11_S872 | 60241394 | c6Np; rG; mA; rA; mU; rG; mU; rG; mA; rC; mU; rU; mC; dC; mA; rG; mA; dC; dC; dA$ | mU; rG; mG; rU; mC; rU; mG; rG; mA; rA; mG; rU; mC; rA; mC; rA; mU; rU; mC; dT; dT$ |
| MYD88_11_S873 | 60241397 | rG; mA; rA; mU; rG; mU; rG; mA; rC; mU; rU; mC; rC; mA; rG; rA; mC; dB; rA$ | mU; rG; mG; rU; mC; rU; mG; rG; mA; rA; mG; rU; mC; rA; mC; rA; mU; rU; mC; dT; dT$ |
| MYD88_11_S874 | 60241400 | rG; mA; rA; mU; rG; mU; rG; mA; rC; mU; rU; mC; rC; mA; rG; rA; mC; dB; rA$ | mU; rG; mG; dT; mC; dT; mG; rG; mA; rA; mG; rU; mC; rA; mC; rA; mU; rU; mC; dT; dT$ |
| MYD88_11_S971 | | c6Np; rG; mA; rA; mU; rG; mU; rG; mA; rC; mU; mU; mC; dC; mA; rG; mA; dC; dC; rA$ | mU; rG; rG; dT; mC; dT; mG; rG; mA; rA; mG; dT; mC; rA; mC; rA; mU; dT; mC; dT; dT$ |
| MYD88_11_S972 | | c6Np; rG; mA; rA; mU; rG; mU; rG; mA; rC; mU; dT; dC; dC; mA; rG; mA; dC; dC; dA$ | mU; rG; rG; mU; mC; mU; rG; rG; mA; rA; rG; mU; mC; rA; mC; rA; mU; mU; mC; dT; dT$ |
| MYD88_11_S973 | | c6Np; rG; rA; rA; dT; rG; dT; rG; rA; dC; dT; dT; dC; dC; rA; rG; rA; dC; dC; rA$ | mU; rG; rG; dT; mC; dT; mG; rG; mA; rA; mG; dT; mC; rA; mC; rA; mU; dT; mC; dT; dT$ |
| MYD88_11_S974 | | c6Np; rG; rA; rA; dT; rG; dT; rG; rA; dC; dT; dT; dC; dC; rA; rG; rA; dC; dC; rA$ | mU; rG; rG; mU; mC; mU; rG; rG; mA; rA; rG; mU; mC; rA; mC; rA; mU; mU; mC; dT; dT$ |

-continued

| Name | Batch Number | Sense 5->3 | Antisense 5->3 |
|---|---|---|---|
| TIRAP_1_S73 | 60258224 | rC; mC; rU; mG; rG; mU; rG; mC; rA; mA; rG; mU; rA; mC; rC; mA; rG; mA; rU$ | mA; rU; mC; rU; mG; rG; mU; rA; mC; rU; mU; rG; mC; rA; mC; rC; mA; rG; mG$ |
| TIRAP_2_S73 | 60258227 | rA; mG; rC; mU; rC; mC; rG; mA; rU; mU; rC; mA; rU; mG; rU; mA; rC; mU; rA$ | mU; rA; mG; rU; mA; rC; mA; rU; mG; rA; mA; rU; mC; rG; mG; rA; mG; rC; mU$ |
| TLR2_1_S710 | 60205154 | rG; rG; rU; rG; rC; rA; rA; rG; rU; rA; rA; rU; rG; rA; rA; rC; rU; rG; rA; rC; rG; rA$ | rU; rC; rC; rA; rG; rU; rU; rC; rU; rA; rC; rU; rU; rG; rC; rC$ |
| TLR2_1_S814_M1 | 140417 | idB; rG; rG; rU; rG; rC; rA; rA; rG; dT; rA; dT; rG; rA; rA; dC; rU; rG; LdG; rU$ | rA; mC; rC; mA; rG; mU; rU; mC; rA; rU; rA; mC; rU; mU; rG; mC; rA; mC; rC$ |
| TLR2_1_S815 | 140418 | idB; rG; rG; dT; rG; dC; rA; rA; rG; dT; mA; dT; rG; rA; rA; dC; mU; LdG; rG; rA$ | mU; mC; rC; rA; rG; mU; mU; mC; rA; rU; rA; mC; mU; mU; rG; mC; rA; mC; rC$ |
| TLR2_15_S73 | 60238659 | rG; mG; rG; mC; rA; mG; rU; mC; rU; mU; rG; mA; rA; mC; rA; mU; rU; mU; rA$ | mU; rA; mA; rA; mU; rG; mU; rU; mC; rA; mA; rG; mA; rC; mU; rG; mC; rC; mC$ |
| TLR2_16_S73 | 60274507-60274508 | rG; mA; rG; mU; rG; mG; rU; mG; rC; mA; rA; mG; rU; mA; rU; mG; rA; mA; rC$ | mG; rU; mU; rC; mA; rU; mA; rC; mU; rU; mG; rC; mA; rC; mC; rA; mC; rU; mC$ |
| TLR2_16_S938 | 60274509-60274510 | rG; mA; rG; mU; rG; mG; rU; mG; rC; mA; rA; mG; rU; mA; rU; mG; rA; mA; rA$ | mU; rU; mU; rC; mA; rU; mA; rC; mU; rU; mG; rC; mA; rC; mC; rA; mC; rU; mC$ |
| TLR2_16_S939 | 60274509-60274508 | rG; mA; rG; mU; rG; mG; rU; mG; rC; mA; rA; mG; rU; mA; rU; mG; rA; mA; rA$ | mG; rU; mU; rC; mA; rU; mA; rC; mU; rU; mG; rC; mA; rC; mC; rA; mC; rU; mC$ |
| TLR2_16_S941 | 60274507-60274510 | rG; mA; rG; mU; rG; mG; rU; mG; rC; mA; rA; mG; rU; mA; rU; mG; rA; mA; rC$ | mU; rU; mU; rC; mA; rU; mA; rC; mU; rU; mG; rC; mA; rC; mC; rA; mC; rU; mC$ |

Table 7 hereinbelow provides a sequence code of the modified nucleotides/unconventional moieties utilized in preparing the dsRNA oligonucleotides according to Structure (A2)

| Name | Batch Numbers | Sense 5->3 | AntiSense 5->3 |
|---|---|---|---|
| MYD88_13_S73 | 60206348 | rG; mG; rA; mG; rA; mU; rG; mA; rU; mC; rC; mG; rG; mC; rA; mA; rC; mU; rA$ | mU; rA; mG; rU; mU; rG; mC; rC; mG; rG; mA; rU; mC; rA; mU; rC; mU; rC; mC$ |
| MYD88_18_S73 | 60238315 | rG; mC; rC; mU; rA; mU; rC; mG; rC; mU; rG; mU; rU; mC; rU; mU; rG; mA; rA$ | mU; rU; mC; rA; mA; rG; mA; rA; mC; rA; mG; rC; mG; rA; mU; rA; mG; rG; mC$ |
| TIRAP_7_S73 | 60227223 | rC; mG; rG; mA; rA; mC; rU; mC; rC; mG; rA; mU; rU; mC; rA; mU; rG; mU; rA$ | mU; rA; mC; rA; mU; rG; mA; rA; mU; rC; mG; rG; mA; rG; mU; rU; mC; rC; mG$ |
| TIRAP_9_S73 | 60227229 | rG; mA; rU; mU; rC; mA; rU; mG; rU; mA; rC; mU; rA; mU; rG; mU; rG; mG; rA$ | mU; rC; mC; rA; mC; rA; mU; rA; mG; rU; mA; rC; mA; rU; mG; rA; mA; rU; mC$ |
| TIRAP_15_S73 | 60238354 | rC; mC; rA; mC; rA; mG; rU; mG; rA; mG; rG; mA; rG; mG; rA; mU; rU; mU; rA$ | mU; rA; mA; rA; mU; rC; mC; rU; mC; rC; mU; rC; mA; rC; mU; rG; mU; rG; mG$ |
| TLR2_3_S73 | 60205160 | rC; mG; rG; mG; rC; mA; rA; mA; rU; mG; rG; mA; rU; mC; rA; mU; rU; mG; rA$ | mU; rC; mA; rA; mU; rG; mA; rU; mC; mC; rA; mU; rU; mU; rG; mC; mC; rC; mG$ |

| Name | Batch Numbers | Sense 5->3 | AntiSense 5->3 |
|---|---|---|---|
| TLR2_3_S818_M1 | 140422 | idB; rC; rG; rG; rG; rC; rA; rA; rA; dT; rG; rG; rA; dT; rC; rA; rU; dT; rG; rU$ | rA; mC; rA; rA; mU; rG; rA; mU; rC; rC; rA; mU; rU; mU; rG; mC; rC; mC; rG$ |
| TLR4_1_S500 | 126174 | rG; mG; rC; mU; rG; mG; rC; mA; rA; mU; rU; mC; rU; mU; rU; mC; rA; mA; rA | mU; rU; mU; rG; mA; rA; mA; rG; mA; rA; mU; rU; mG; rC; mC; rA; mG; rC; mC |
| TLR4_3_S500 | 126176 | rG; mA; rU; mC; rU; mU; rG; mG; rG; mA; rG; mA; rA; mU; rU; mU; rA; mA; rA | mU; rU; mU; rA; mA; rA; mU; rU; mC; rU; mC; rC; mC; rA; mA; rG; mA; rU; mC |
| TLR4_5_S500 | 126178 | rG; mU; rU; mG; rG; mU; rG; mU; rA; mU; rC; mU; rU; mU; rG; mA; rA; mU; rA | mU; rA; mU; rU; mC; rA; mA; rA; mG; rA; mU; rA; mC; rA; mC; rC; mA; rA; mC |

TABLE 8

Code of the modified nucleotides/unconventional moieties

| Code | modification |
|---|---|
| z | prefix "z" refers to a nucleotide or non-nucleotide moiety covalently attached to the 3' or 5' terminus |
| $ | No 3' Phosphate moiety. terminal phosphate. |
| 5'p | phosphate group on the 5' position of the 5'-terminal nucleotide |
| zdT; zdT$ | Deoxy-Thymidine-3'-Phosphate-Deoxy-Thymidine (i.e., dTdT overhang at the 3' terminus with no 3' phosphate) |
| zc3p | On the 5' terminus: A C3-alkyl moiety (also referred to as $(CH_2)_3$—OH or C3—OH) linked to the 5' terminus via a phosphate moiety (not depicted), wherein the OH group is present on the terminal carbon of the C3 moiety. On the 3' terminus: A $(CH_2)_3$-Pi C3-alkyl moiety (also referred to as C3-Pi) linked to the 3' terminus via a phosphate moiety (not depicted), wherein Pi is a 3' terminal phosphate moiety |
| zc3p; zc3p | Two $(CH_2)_3$-Pi C3-alkyl moieties (also referred to as C3Pi-C3Pi or as $(CH_2)_3$Pi-$(CH_2)_3$Pi) linked via a phosphate moiety (Pi), comprising a 3' terminal phosphate moiety (Pi), and linked to the 3' terminus via a phosphate moiety (not depicted) |
| rN2p | ribo-nucleotide-2'-phosphate (e.g., rA2p) - a ribonucleotide forming a 2'-5' phosphodiester bond between the 2' ribose carbon of the ribonucleotide and the 5' ribose carbon of the next ribonucleotide in the 5' > 3' direction |
| c6Np | (5' cap) Amino-C6-Phosphate or Amino modifier C6 (Glen Research) |
| dA | deoxyriboadenosine-3'-phosphate |
| dB | abasic deoxyribose-3'-phosphate |
| dC | deoxyribocytidine-3'-phosphate |
| dG | deoxyriboguanosine-3'-phosphate |
| dT | thymidine-3'-phosphate |
| dT$ | thymidine (no phosphate) |
| iB | inverted deoxy-abasic |
| LdA | L-deoxyriboadenosine-3'-phosphate (mirror image dA) |
| LdA$ | L-deoxyriboadenosine (no phosphate) (mirror image dA) |
| LdC | L-deoxyribocyt0idine-3'-phosphate (mirror image dC) |
| LdC$ | L-deoxyribocytidine (no phosphate) (mirror image dC) |
| LdG | L-deoxyriboguanosine-3'-phosphate (mirror image dG) |
| LdT | L-deoxyribothymidine-3'-phosphate (mirror image dT) |
| LdT$ | L-deoxyribothymidine (no phosphate) (mirror image dT) |
| mA | 2'-O-methyladenosine-3'-phosphate |
| mA$ | 2'-O-methyladenosine (no phosphate) |
| mC | 2'-O-methylcytidine-3'-phosphate |
| mC$ | 2'-O-methylcytidine (no 3'-phosphate) |
| mG | 2'-O-methylguanosine-3'-phosphate |
| mG$ | 2'-O-methylguanosine (no phosphate) |
| mU | 2'-O-methyluridine-3'-phosphate |
| mU$ | 2'-O-methyluridine (no phosphate) |
| rA | riboadenosine-3'-phosphate |
| rA$ | riboadenosine (no phosphate) |
| rC | ribocytidine-3'-phosphate |
| rC$ | ribocytidine (no phosphate) |
| rG | riboguanosine-3'-phosphate |
| rU | ribouridine-3'-phosphate |
| rU$ | ribouridine (no phosphate) |

Example 2

RNAi Activity of Exemplary Double Stranded Oligonucleotide Compounds Activity Single stranded oligonucleotides (sense strand and antisense strand) are synthesized using standard synthesis procedures. DMT-propane-Diol phosphoramidite ChemGenes; CLP-9908) is coupled at a concentration of 0.05M.

Duplexes are generated by annealing complementary single stranded oligonucleotides. In a laminar flow hood, a ~500 µM Stock Solution of single stranded oligonucleotide is prepared by diluting in WFI (water for injection, Norbrook). Actual ssRNA (single stranded) concentrations are determined by diluting each 500 µM ssRNA 1:200 using WFI, and measuring the OD using Nano Drop. The procedure is repeated 3 times and the average concentration is calculated. The Stock Solution was then diluted to a final concentration of 250 µM. Complementary single strands were annealed by heating to 85° C. and allowing to cool to room temperature over at least 45 minutes. Duplexes were tested for complete annealing by testing 5 µl on a 20% polyacrylamide gel and staining. Samples were stored at −80° C.

The double stranded nucleic acid molecules disclosed herein were tested for activity as follows: About 1.5-2×10$^5$ tested cells (HeLa cells and/or 293T cells for siRNA targeting human genes and NRK52 (normal rat kidney proximal tubule cells) cells and/or NMuMG cells (mouse mammary epithelial cell line) for siRNA targeting the rat/mouse gene) were seeded per well in 6 wells plate (70-80% confluent).

About 24 hours later, cells were transfected with modified siRNA compounds using the Lipofectamine™ 2000 reagent (Invitrogen) at final concentrations of from 0.001 nM to about 50 nM. The cells were incubated at 37° C. in a $CO_2$ incubator for 72 h.

As positive control for transfection PTEN-Cy3 labeled modified siRNA compounds are used. GFP siRNA compounds are used as negative control for siRNA activity.

At 72 h after transfection cells are harvested and RNA was extracted from cells. Transfection efficiency is tested by fluorescent microscopy.

The percent of inhibition of gene expression using specific preferred siRNA structures is determined using qPCR analysis of a target gene in cells expressing the endogenous gene.

TABLE 9

Activity of certain preferred TLR2 compounds

| Name | Sense sequence | Antisense sequence | Residual mRNA in Rat1 cells stable expressing human TLR2 20, 5, 0.5, 0.1 nM (repeat) |
|---|---|---|---|
| TLR2_31 | GGUAAAUCUGAGAGCUGCA | UGCAGCUCUCAGAUUUACC | 14, 7, 16 (10, 42, 86) |
| TLR2_42 | GGGUAAAUCUGAGAGCUGC | GCAGCUCUCAGAUUUACCC | 9, 14, 15, 37 (9, 25, 40) |
| TLR2_25 | GGGUGGAGAACCUUAUGGU | ACCAUAAGGUUCUCCACCC | 14, 17, 90, 54 (42, 84, 13, 29) |
| TLR2_28 | GGCAAGUGGAUCAUUGACA | UGUCAAUGAUCCACUUGCC | 24, 21, 30, 39 (12, 48, 64) |
| TLR2_34 | CUGGACUUCUCCCAUUUCA | UGAAAUGGGAGAAGUCCAG | 9, 28, 30, 28 (16, 37, 84) |
| TLR2_43 | CCAUUGAAAAGAGCCACAA | UUGUGGCUCUUUUCAAUGG | 34, 24, 18, 19 (6, 29, 46) |
| TLR2_47 | AUAAUGAACACCAAGACCU | AGGUCUUGGUGUUCAUUAU | 31, 35, 33, 37 (12, 43, 66) |

The IC50 value of the tested RNAi activity is determined by constructing a dose-response curve using the activity results obtained with the various final siRNA concentrations. The dose response curve is constructed by plotting the relative amount of residual target mRNA versus the logarithm of transfected siRNA concentration. The curve is calculated by fitting the best sigmoid curve to the measured data. The method for the sigmoid fit is also known as a 3-point curve fit.

$$Y = Bot + \frac{100 - Bot}{1 + 10^{(LogIC50-X) \times HillSlope}}$$

where Y is the residual target mRNA response, X is the logarithm of transfected siRNA concentration, Bot is the Y value at the bottom plateau, Log IC50 is the X value when Y is halfway between bottom and top plateaus and HillSlope is the steepness of the curve.

The activity of certain preferred TLR4 compounds was examined using the psiCHECK™ system (Promega). All tested siRNAs of Table 10 had the same sequences of Sense (passenger) and Anti-Sense (guide) strands, referred herein together as the TLR4_14 siRNA (having SEQ ID NOS: 20624 and 20633, respectively), with different modification patterns as depicted in Table 10 (Table 8 hereinabove provides a legend for the modifications appearing in Table 10):

TABLE 10

Activity of certain preferred TLR4 compounds

| siRNA name/strand | Sequence (5'>3') | SEQ ID NO. |
|---|---|---|
| TLR4_14_S709 Sense Strand | rC; rU; rC; rA; rA; rU; rC; rU; rC; rU; rC; rU; rU; rU; rA; rG; rA; rC; rA; zdT; zdT$ | SEQ ID NO. 20624 |
| TLR4_14_S709 Anti-Sense Strand | rU; rG; rU; rC; rU; rA; rA; rA; rG; rA; rG; rA; rG; rA; rU; rU; rG; rA; rG; zdT; zdT$ | SEQ ID NO. 20633 |
| TLR4_14_S2784 Sense Strand | zc3p; mC; rU; mC; rA; rA; mU; rC; mU; rC; mU; rC; rU; rU; mU; rA; rG; rA; mC; rA; zc3p | SEQ ID NO. 20624 |
| TLR4_14_S2784 Anti-Sense Strand | 5'p; mU; rG; mU; rC; mU; rA; rA2p; rA; rG; rA; rG; rA; rG; rA; mU; rU; mG; rA; rG; zc3p; zc3p | SEQ ID NO. 20633 |
| TLR4_14_S2785 Sense Strand | zc3p; mC; mU; rC; rA; rA; mU; rC; mU; rC; mU; rC; mU; rU; mU; rA; rG; rA; mC; rA; zc3p | SEQ ID NO. 20624 |
| TLR4_14_S2785 Anti-Sense Strand | 5'p; mU; rG; mU; rC; mU; rA; rA2p; rA; rG; rA; rG; rA; rG; rA; mU; rU; mG; rA; rG; zc3p; zc3p | SEQ ID NO. 20633 |

In order to evaluate the specific on-target activity of the siRNAs of Table 10, a first construct was generated in which one copy of the full target sequence of the antisense (guide) strand of the TLR4_14 siRNA (i.e., a guide strand complementary sequence, GS-CM or AS-CM) was cloned into the multiple cloning site of a psiCHECK™-2-based construct, located in the region coding for the 3'-UTR of *Renilla* luciferase mRNA downstream to the stop codon. In addition, the psiCHECK™-2 vector contains a second reporter gene, Firefly luciferase, transcribed from a different promoter and non-affected by the oligonucleotide under study, useful for normalization of *Renilla* luciferase expression across different transfections. On-target activity results in cleavage and subsequent degradation of the fused mRNA or in translation inhibition of the encoded protein, thus leading to a lower level of detectable *Renilla* luciferase. About $1.3 \times 10^6$ human HeLa cells were inoculated in 10 cm dishes and incubated at $37 \pm 1°$ C., 5% $CO_2$ for 24 hours. Growth medium was replaced one day post inoculation by 8 mL fresh growth medium and cells in each plate were transfected with the psiCHECK™-2 plasmid mentioned above, using the Lipofectamine™2000 reagent (Invitrogen) according to manufacturer's protocol and further incubated for 24 hours. Following incubation, cells were re-plated in a 96-well plate at final concentration of $8 \times 10^3$ cells per well in 80 μL growth medium. 2-3 hours later, cells were transfected with the TLR4_14 siRNAs of Table 10 using the Lipofectamine™2000 reagent (Invitrogen) at various final concentrations. Control cells were not exposed to any siRNA. Cells were then incubated for 48 hours at $37 \pm 1°$ C. and *Renilla* and FireFly Luciferase activities were measured as described below.

The *Renilla* and FireFly Luciferase activities were measured in each of the siRNA transfected samples, using the Dual-Luciferase® Assay kit (Promega, Cat#E1960) according to manufacturer procedure. *Renilla* Luciferase activity value was divided by Firefly Luciferase activity value for each sample (for normalization). *Renilla* luciferase activity is finally expressed as the percentage of the normalized activity value in tested sample relative to the normalized value obtained in cells transfected with the corresponding psiCHECK™-2 plasmid only but with no siRNA. These values represent dose-dependent siRNA on-target knock-down activity and are depicted in FIG. 1A.

Lower percentage of residual *Renilla* Luciferase activity is indicative of higher on-target knock-down activity. As can be seen in FIG. 1A, all tested siRNAs in Table 10 demonstrated knock-down activity.

Figure 1B:
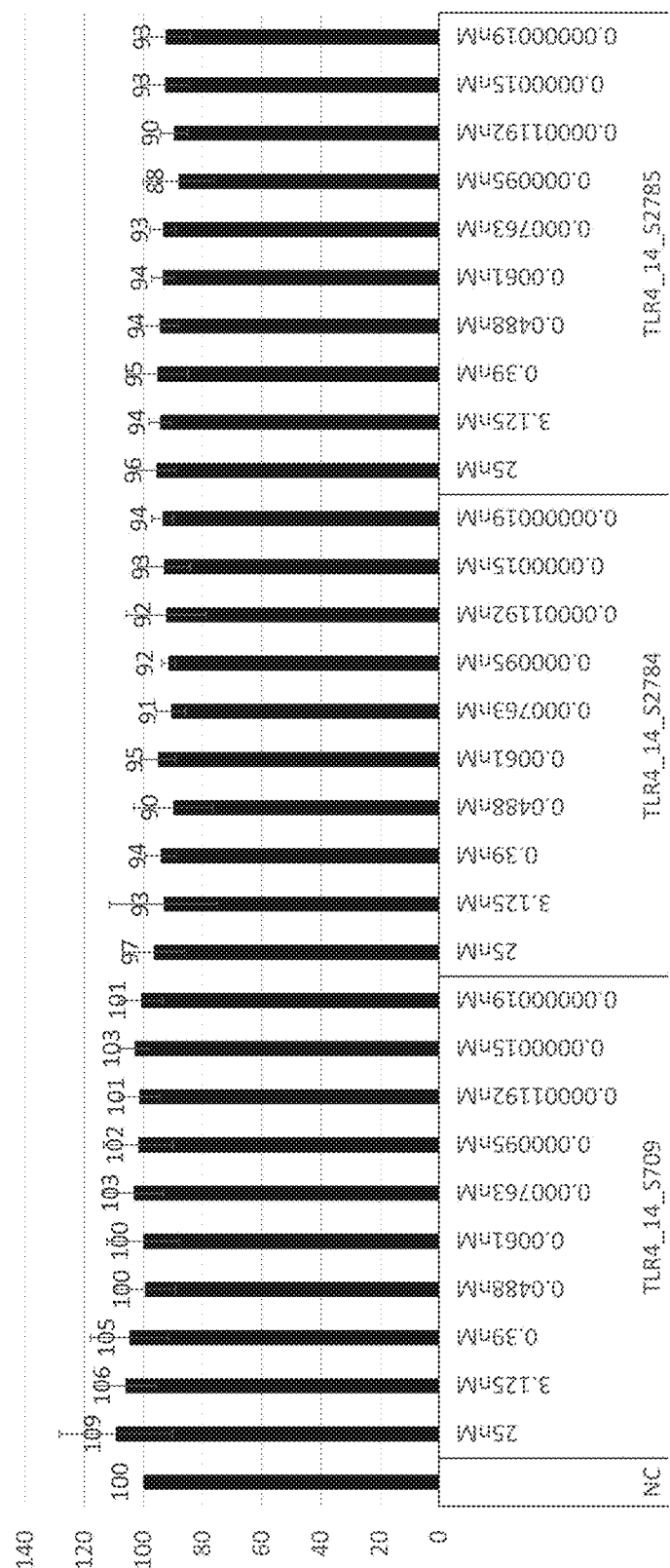

In order to examine the seed-mediated off-target effect of the antisense (guide) strand, a second psiCHECK™-2-based construct was generated having in its multiple cloning site three copies of sequences complementary to the TLR4_14 guide strand seed region (GS-SM or AS-SMx3) cloned at optimal distances between them. The seed region refers to the nucleotides at positions 2-8 (5'>3') of the antisense strand. These constructs were transfected into HeLa cells together with the various tested siRNA constructs and assayed as above. Lower percentage of residual *Renilla* Luciferase activity when this off-target construct is assayed is indicative of higher off-target knock-down activity, so higher percentages in this case are desirable. Dose-dependent off-target activity of the siRNAs of Table 10 are depicted in FIG. 1B. Valued represented in FIGS. 1A and 1B represent an average of 4 experiments.

Serum Stability

The double stranded nucleic acid molecules were tested for duplex stability in human serum or human tissue extract, as follows:

dsRNA molecules at final concentration of 7 uM are incubated at 37° C. in 100% human serum (Sigma Cat# H4522). (siRNA stock 100 uM diluted in human serum 1:14.29 or human tissue extract from various tissue types.). Five μL (5 μL) are added to 15 μL 1.5×TBE-loading buffer at different time points (for example 0, 30 min, 1 h, 3 h, 6 h, 8 h, 10 h, 16 h and 24 h). Samples are immediately frozen in liquid nitrogen and are kept at −20° C.

Each sample is loaded onto a denaturing 20% acrylamide gel, prepared according to methods known in the art. The oligos are visualized with ethidium bromide under UV light.

In general, the dsRNAs having specific sequences that are selected for in vitro testing are specific for human and a second species such as rat or rabbit genes.

Stability to Exonucleases

To study the stabilization effect of 3' non-nucleotide moieties on a nucleic acid molecule the sense strand, the antisense strand and the annealed siRNA duplex are incubated in cytosolic extracts prepared from different cell types. A protocol for testing stability in HCT116 cells is provided below.

Extract: HCT116 cytosolic extract (12 mg/ml).

Extract buffer: 25 mM HEPES pH-7.3 at 37° C.; 8 mM MgCl; 150 mM NaCl with 1 mM DTT was added fresh immediately before use.

Method: 3.5 ml of test siRNA (100 mM), were mixed with 46.5 ml contain 120 mg of HCT116 cytosolic extract. The 46.5 ml consists of 12 ml of HCT116 extract, and 34.5 ml of the extract buffer supplemented with DTT and protease inhibitors cocktail/100 (Calbiochem, setIII-539134). The final concentration of the siRNA in the incubation tube is 7 mM. The sample is incubated at 37° C., and at the indicated time point 5 ml are moved to fresh tube, mixed with 15 ml of 1×TBE-50% Glycerol loading buffer, and snap frozen in Liquid N2. The final concentration of the siRNA in the loading buffer is about 1.75 mM (21 ng siRNA/ml). For analyses by native PAGE and EtBr staining 50 ng are loaded per lane. For Northern analyses 1ng of tested siRNA is loaded per lane. Other cell types include HeLa and hepatic stellate cells (HSC).

The applicants have shown that nucleic acid molecules which include the 3' terminal alkyl; or alkyl derivative overhang exhibit enhanced stability compared to a blunt ended nucleic acid molecules and nucleic acid molecules comprising 3' nucleotide overhangs.

Example 3

Stability of Double Stranded RNA Molecules in Bronchoalveolar Lavage Fluid

Nuclease resistance of the dsRNA compounds disclosed herein is tested in human serum and/or in bronchoalveolar lavage fluid (BALF). For stability testing, a dsRNA compound is diluted in human serum or in bronchoalveolar lavage fluid (BALF) to a required final concentration (e.g. 7 μM). A 5 μL aliquot is transferred to 15 μL of 1.5×TBE-loading buffer, immediately frozen in liquid nitrogen, and transferred to −20° C. This represents "Time Point 0". The remaining dsRNA solution is divided into 5 μL aliquots, which are incubated at 37° C. for 30 min, 1 h, 6 h, 8 h, 10 h, 16 h or 24 h.

Following incubation, dsRNA compound samples are transferred to 15 μL of 1.5×TBE-loading buffer. 5 μL of each dsRNA compound in loading buffer sample is loaded onto denaturing 20% polyacrylamide gel and electrophoresis is performed. The positive control, double-strand migration reference (a non-relevant, 19-base pairs, blunt-ended, double-stranded RNA with similar chemical modifications), and single-strand migration reference (a non-relevant ssRNA with chemical modifications), as well as the Time Point 0 sample are loaded on the same gel and electrophoresed in parallel.

For dsRNA visualization the gel is stained with Ethidium bromide solution (1.0 μg/μL).

Stability of dsRNA compounds disclosed herein is determined by examining the migration pattern of siRNA samples on PAGE following incubation in human serum and/or in bronchoalveolar lavage fluid (BALF or BAL).

As can be seen in FIGS. 2A and 2B, two siRNA compounds targeting human TLR4 (TLR4_14_S2784 and TLR4_14_S2785, respectively, as described in Table 10 herein above) were incubated for 24 hours at 37° C. in human serum, in BAL fluid or in cytosolic extract from HCT 116 cells, essentially as described above. At time points between 0 and 24 hours after incubation initiation, siRNA aliquots were transferred to formamide loading buffer, boiled at 95° C. for 5 min and immediately transferred to ice. The aliquots were then analyzed by 15% denaturing polyacrylamide gel electrophoresis. Next, the RNA was transferred from the gel to a Hybond XL membrane (GE). The RNA strands were cross linked to the membrane by 5 min of ultra-violet (UV) irradiation. For detection of the RNA strands the membrane was subjected to hybridization with a specific complementary radiolabel oligonucleotide probe for either the sense or anti-sense strand. The stability was determined based on gel migration patterns, namely by the presence and intensity of a band indicative of the non-cleaved siRNA and/or the presence and intensity of a band indicative of a product of nuclease degradation of the siRNA. Gel migration patterns of the tested siRNAs as determined from the hybridized membranes are depicted in FIGS. 2A and 2B. As a negative control for degradation, the siRNAs were put in PBS at the beginning of incubation (time=0) and run on the gel. As can be seen, both examined siRNAs appeared to be stable and non-degraded in all the tested conditions for at least 24 hours.

Example 4

Efficacy of Therapeutic Activity of dsRNA Directed to TLR2 (SEQ ID NO1): TLR4 (SEQ ID NO:2-4) MYD88 (SEQ ID NOS:5-9), TICAM1 (SEQ ID NO:10) and TIRAP (SEQ ID NOS:11-12) in Mouse Models of Orthotopic Vascularized Aerated Lung Transplantation Therapeutic efficacy of dsRNA compounds described herein in preventing primary graft dysfunction caused by both prolonged cold ischemia and immune rejection are tested in syngeneic and allogeneic mouse orthotopic models of lung transplantation. The method of orthotopic vascularized aerated left lung transplantation in the mouse utilizes cuff techniques for the anastomosis of pulmonary artery, pulmonary veins and bronchus. This method has been reported in several publications (Okazaki et al., Am J Transplant, 2007; 7:1672-9 and Krupnick et al. Nature Protocols, 2009; vol. 4 No. 1:86-93).

dsRNA test compounds: test compounds are preferably dsRNA having cross species specificity to human and mouse or human and rat mRNA target sequences. The sense and antisense sequences of dsRNA compounds that target TLR2 are set forth in SEQ ID NOS: 13-5846; the sense and antisense sequences of dsRNA compounds that target TLR4 are set forth in SEQ ID NOS: 5847-12144; The sense and antisense sequences of dsRNA compounds that target MYD88 are set forth in SEQ ID NOS: 12145-16332; The sense and antisense sequences of dsRNA compounds that target TICAM1 are set forth in SEQ ID NOS: 16333-18242; The sense and antisense sequences of dsRNA compounds that target TIRAP are set forth in SEQ ID NOS: 18243-20606. Certain preferred oligonucleotide pairs useful in generating double stranded nucleic acid molecules are set forth in Tables 1-5. The sense and/or antisense strands are preferably chemically modified as disclosed, supra.

Dosage and administration: dsRNA compounds are administered at the end of lung transplantation surgery (immediately after anastomosis opening), by intratracheal instillation to the recipient animal. The following doses of individual dsRNA compounds are tested in these animal models: 6 μg/mouse, 12.5 μg/mouse, 25 μg/mouse and 50 μg/mouse. Preferred double stranded nucleic acid molecules are generated using the sequences of the oligonucleotide pairs set forth in Tables 1-5.

Mouse Syngeneic Lung Transplantation (C57Bl/6->C57Bl/6)

Experimental design: Both donor and recipient are C57BL/6 mice. Prior to transplantation, ischemia reperfusion injury is induced by prolonged cold preservation of the lung transplant for 18 hours in cold storage in a low dextrose solution with components similar to solutions used to preserve human lung transplants (18 hours of cold ischemia time (CIT)). This method induces symptoms consistent with primary graft dysfunction 24 hours post-transplantation. Test dsRNA is administered into the trachea. Lung recipients are assessed 24 hours later for lung injury.

Administration: By intratracheal instillation of dsRNA solution to the lungs; 1 dose of a dsRNA compound or of a combination of dsRNA compounds is administered immediately after anastomosis opening on Day 0.

Evaluation: Lung recipients are evaluated at 24 hours post transplantation through assessing lung function, as measured by:
  Gross pathology—appearance of pulmonary edema;
  Pulmonary function—PaO2, oxygenation of arterial blood;
  Intra-airway accumulation of cellular infiltrates; and
  Total amount and differential counts of bronchoalveolar lavage (BAL) cells Results: In this syngeneic model, mouse isografts exposed to prolonged cold ischemia (18 hours CIT) develop impaired oxygenation, pulmonary edema, increased inflammatory cytokine production and intra-graft and intra-airway accumulation of granulocytes as measured 24 hours post-transplantation. By contrast, mouse lung recipients of 1 hour cold preserved grafts (1 hour CIT) show little evidence of lung injury 24 hours post-transplantation.

The test article (composition comprising a combination of TLR2 and TLR4 double stranded nucleic acid molecules; dsRNA specific for TLR2, dsRNA specific for TLR4 or vehicle) was administered immediately after opening of anastomosis and beginning of reperfusion. Preferred double stranded nucleic acid molecules are generated using the sequences of the oligonucleotide pairs set forth in Tables 1-5.

Example 5

Therapeutic Activity of dsRNA Directed to TLR2 (SEQ ID NO1): TLR4 (SEQ ID NO:2-4) MYD88 (SEQ ID NOS:5-9), TICAM1 (SEQ ID NO:10) and TIRAP (SEQ ID NOS:11-12) in the Mouse Allogeneic Lung Transplantation (Balb/C->C57Bl/6)

Experimental design: In this model prolonged cold ischemia prevents lung allograft acceptance mediated by immunosuppression. In this model Balb/c lungs are subjected to 18 hours of cold ischemia time (CIT) and are transplanted into C57Bl/6 recipients that are treated with immunosuppressants: anti-CD40L on post operative day 0 and CTLA4Ig on day 2. In contrast to recipients who received allografts stored for 1 hour, these stored for 18 hours acutely rejected their allografts with marked intragraft accumulation of IFNγ+CD8+ T cells.

Evaluation: Lung recipients were evaluated at 7 days post transplantation through assessing:
  Abundance of intragraft IFNγ+CD8+ T cells (by FACS)
  Histopathological signs of acute graft rejection, A score
  Administration: By intratracheal instillation of dsRNA solution to the lungs; 2 doses of a dsRNA compound or of a combination of dsRNA compounds are administered immediately after anastomosis opening on Day 0 and on Day 1 post Tx.

Example 6

Animal Models of Neuropathic Pain: Therapeutic Activity of dsRNA Directed to TLR2 (SEQ ID NO1): TLR4 (SEQ ID NO:2-4); MYD88 (SEQ ID NOS:5-9), TICAM1 (SEQ ID NO:10) and TIRAP (SEQ ID NOS:11-12), in the Spinal Nerve Ligation Model (Chung) in Rats The Chung rat model (Kim and Chung, 1992. Pain. 1992 September; 50(3):355-63.) duplicates the symptoms of human patients with causalgia, or burning pain due to injury of a peripheral nerve. The Chung procedure produces a long-lasting hyperalgesia to noxious heat and mechanical allodynia of the affected foot. Rats with spinal nerve ligation (SNL) are useful for identifying active dsRNA compounds for use in alleviating neuropathic pain. Preferred dsNA molecules are generated using the sequences of the oligonucleotide pairs set forth in Tables 1-5.

Alleviation Of Neuropathic Pain in Chung Model Rats: The Chung model is performed on male Sprague-Dawley rats weighing 190 to 210 grams to induce an allodynic state. Animals are acclimated for at least 5 days. During acclimation and throughout the entire study duration, animals are housed within a limited access rodent facility and kept in groups with a maximum of 5 rats per cage. Animals are provided ad libitum with a commercial rodent diet and have free access to drinking water. Automatically controlled environmental conditions were monitored daily. Animals are given a unique animal identification tail mark.

During the acclimation period, animals are randomly assigned to experimental groups. Each dosing group is kept in separate cages to avoid cross-contamination which can occur through consumption of fecal matter. 2-3 animals will be housed per cage.

Briefly, the rats are anesthetized with ketamine/xylazine sodium and subsequently, the left L-5 and L-6 spinal nerves is isolated adjacent to the vertebral column and ligated. The muscle is sutured and the skin closed with a clamp. Seven days day postoperative recovery period, the animals are tested for inclusion into the study. Pain is detected when one or more of the criteria below are met:
  Licking of the operated paw, accompanied by gentle biting or pulling nails with the mouth; lifting the operated leg in the air; bearing weight on the side contralateral to the nerve injury; deformities of the hind paw and abnormal walking; weakness of the left hind paw. The animal has to be able to move it leg to ensure that L4 is intact.

Alzet pump: Animals from some groups are implanted subcutaneously with osmotic pumps on the day of surgery. A polyethylene tubing is implanted in the intrathecal space of the spinal cord, ending at level L4 and a cannula was connected to the pump.

Lumbar injections: Animals from some groups are given bolus lumber injections as follows: An intrathecal tube was inserted into the animals IT space at L4-L5 level and the test agents were dosed slowly.

It will be readily apparent to one skilled in the art that substitutions and modifications can be made to the molecules, compositions and methods disclosed herein without departing from the scope and spirit of the invention. Thus, such additional embodiments are within the scope of the disclosure and the following claims. The present disclosures teach one skilled in the art various combinations of oligonucleotides and chemical modifications described herein toward generating therapeutically effective double stranded nucleic acid molecules to down regulate expression of TLR2, TLR4, MYD88, TICAM1 and TIRAP. The therapeutically effective double stranded nucleic acid molecules exhibit one or more of stability in biological fluids, bioavailability, high on target activity, low off target activity. Therefore, the specific embodiments described herein are not limiting and one skilled in the art can readily appreciate that additional specific combinations can be tested without undue experimentation toward identifying therapeutic combinations with improved activity.

The terms "comprising", "having," "including," containing", etc. shall be read expansively and without limitation (e.g., meaning "including, but not limited to,"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

The disclosure has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

Throughout this application various patents and publications are cited. The disclosures of these documents in their entireties are hereby incorporated by reference into this application to more fully describe the state of the art to which this invention pertains.

Although the above examples have illustrated particular ways of carrying out embodiments, in practice persons skilled in the art will appreciate alternative ways of carrying out embodiments, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09796979B2). An electronic copy of the "Sequence Listing" will also be available from the USPTO upon request and payment of the fee set forth in 37 CFR 1.19(b)(3).

The invention claimed is:

1. A double stranded nucleic acid molecule comprising a sense strand and an antisense strand described as the sequence pair set forth as TLR4_14 (SEQ ID NOS: 20624 and 20633, respectively).

2. The double stranded nucleic acid molecule of claim 1 having the following structure:

(A2)

```
5' N1-(N)x-Z 3'    (antisense strand)

3' Z'-N2-(N')y-z" 5' (sense strand)
``` wherein each N2, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 24;

wherein the sequence of (N')y is complementary to the sequence of (N)x and (N)x is complementary to a consecutive sequence in a target RNA set forth in any one of SEQ ID NO:2-4 (TLR4 mRNA);

wherein N1 is an unmodified or modified ribonucleotide covalently bound to (N)x and mismatched to the target RNA;

wherein z" may be present or absent, but if present is a capping moiety covalently attached at the 5' terminus of N2-(N')y;

wherein each of Z and Z' is independently present or absent, but if present is independently 1-5 consecutive nucleotides, consecutive non-nucleotide moieties or a combination thereof covalently attached at the 3' terminus of the strand in which it is present; and wherein the sequence of N1-(N)x is set forth in SEQ ID NO: 20633.

3. The double stranded nucleic acid molecule of claim 2, wherein at least one of N1, N2, N or N' comprises a modified nucleotide or an unconventional moiety.

4. The double stranded nucleic acid molecule of claim 3, wherein N1-(N)x comprises at least one pyrimidine ribonucleotide and wherein at least one of the pyrimidine ribonucleotides in N1-(N)x comprises a 2' sugar modified pyrimidine ribonucleotide.

5. The double stranded nucleic acid molecule of claim 4, wherein the 2' sugar modified ribonucleotide comprises a 2'-OMe sugar modified ribonucleotide.

6. A method for the treatment of a subject in need of treatment for a disease or disorder or symptom or condition associated with the expression of a target gene comprising administering to the subject an amount of a double stranded nucleic acid molecule of claim 1, in an amount effective to down regulate gene expression, wherein the gene encodes a RNA having a polynucleotide sequence as set forth in any one of SEQ ID NO:2-4 (TLR4 mRNA).

7. The method of claim 6, wherein the disease or injury is selected from the group consisting of: chronic or acute aseptic inflammation, neuropathic pain, primary graft failure, ischemia-reperfusion injury, reperfusion injury, reperfusion edema, allograft dysfunction, pulmonary reimplantation response and primary graft dysfunction (PGD) in organ transplantation.

8. The method of claim 7, wherein the disease or injury comprises primary graft dysfunction (PGD) in organ transplantation.

9. The method of claim 8, wherein said organ transplantation comprises lung transplantation.

10. A pharmaceutical composition comprising a double stranded nucleic acid molecule of claim 1 in an amount effective to inhibit gene expression, and a pharmaceutically acceptable carrier wherein the gene encodes a RNA having a polynucleotide sequence set forth in any one of SEQ ID NO:2-4 (TLR4 mRNA).

* * * * *